US011510947B2

(12) United States Patent
Tom et al.

(10) Patent No.: US 11,510,947 B2
(45) Date of Patent: *Nov. 29, 2022

(54) METHODS OF MANUFACTURE OF IMMUNOCOMPATIBLE AMNIOTIC MEMBRANE PRODUCTS

(71) Applicant: Osiris Therapeutics, Inc., Columbia, MD (US)

(72) Inventors: Samson Tom, Baltimore, MD (US); Alla Danilkovitch, Columbia, MD (US); Dana Yoo, Falls Church, VA (US); Timothy Jansen, Baltimore, MD (US); Jin-Qiang Kuang, Woodstock, MD (US); Jennifer Michelle Marconi, Glen Burnie, MD (US)

(73) Assignee: OSIRIS THERAPEUTICS, INC., Columbia, MD (US)

( * ) Notice: Subject to any disclaimer, the term of this patent is extended or adjusted under 35 U.S.C. 154(b) by 432 days.

This patent is subject to a terminal disclaimer.

(21) Appl. No.: 16/736,066

(22) Filed: Jan. 7, 2020

(65) Prior Publication Data
US 2020/0281981 A1    Sep. 10, 2020

Related U.S. Application Data

(63) Continuation of application No. 14/070,035, filed on Nov. 1, 2013, now Pat. No. 10,576,104, which is a
(Continued)

(51) Int. Cl.
*A61K 35/50* (2015.01)
*A01N 1/02* (2006.01)
(Continued)

(52) U.S. Cl.
CPC ............ *A61K 35/28* (2013.01); *A01N 1/0221* (2013.01); *A61K 35/50* (2013.01);
(Continued)

(58) Field of Classification Search
CPC ..................................................... A61K 35/50
See application file for complete search history.

(56) References Cited

U.S. PATENT DOCUMENTS 5,891,617 A    4/1999    Watson et al.
6,152,142 A    11/2000    Tseng
(Continued)

FOREIGN PATENT DOCUMENTS

CA    2790322    8/2011
CA    2790325    8/2011
(Continued)

OTHER PUBLICATIONS

Niknejad et al. "Properties of the amniotic membrane for potential use in tissue engineering" Eur Cell Mater, Apr. 29, 2008;p. 15:88-99 (Year: 2008).*

(Continued)

*Primary Examiner* — Blaine Lankford
*Assistant Examiner* — Lauren K Van Buren
(74) *Attorney, Agent, or Firm* — Norton Rose Fulbright US LLP

(57) ABSTRACT

Provided herein is a placental product comprising an immunocompatible amniotic membrane. Such placental products can be cryopreserved and contain viable therapeutic cells after thawing. The placental product of the present invention is useful in treating a patient with a tissue injury (e.g. wound or burn) by applying the placental product to the injury. Similar application is useful with ligament and tendon repair and for engraftment procedures such as bone engraftment.

14 Claims, 30 Drawing Sheets

Related U.S. Application Data continuation of application No. 13/030,562, filed on Feb. 18, 2011, now abandoned.

(60) Provisional application No. 61/369,562, filed on Jul. 30, 2010, provisional application No. 61/338,464, filed on Feb. 18, 2010, provisional application No. 61/338,489, filed on Feb. 18, 2010.

(51) Int. Cl.
*A61K 38/57* (2006.01)
*A61K 35/28* (2015.01)
*A61K 38/18* (2006.01)
*A61K 38/39* (2006.01)
*C12N 5/073* (2010.01)

(52) U.S. Cl.
CPC ...... *A61K 38/1825* (2013.01); *A61K 38/1841* (2013.01); *A61K 38/39* (2013.01); *A61K 38/57* (2013.01); *C12N 5/0605* (2013.01); *C12N 2500/02* (2013.01); *C12N 2501/115* (2013.01); *C12N 2502/025* (2013.01)

(56) References Cited

U.S. PATENT DOCUMENTS

| | | | |
|---|---|---|---|
| 6,326,019 B1 | 12/2001 | Tseng | |
| 7,928,280 B2 | 4/2011 | Hariri et al. | |
| 8,071,135 B2 | 12/2011 | Liu et al. | |
| 8,460,715 B2 | 6/2013 | Daniel | |
| 8,932,641 B2 | 1/2015 | Nikaido et al. | |
| 9,956,248 B2 | 5/2018 | Tom et al. | |
| 10,272,116 B2 | 4/2019 | Tom et al. | |
| 10,576,104 B2* | 3/2020 | Tom | A61K 38/1841 |
| 2002/0039788 A1 | 4/2002 | Isseroff et al. | |
| 2003/0032179 A1 | 2/2003 | Hariri | |
| 2003/0187515 A1 | 10/2003 | Hariri et al. | |
| 2003/0235563 A1 | 12/2003 | Strom et al. | |
| 2004/0048796 A1 | 3/2004 | Harari et al. | |
| 2006/0003927 A1 | 1/2006 | Champion et al. | |
| 2006/0182724 A1 | 8/2006 | Riordan | |
| 2006/0233765 A1 | 10/2006 | Messina et al. | |
| 2006/0228339 A1 | 10/2006 | Wang | |
| 2007/0015278 A1 | 1/2007 | Li et al. | |
| 2007/0041954 A1 | 2/2007 | Ichim | |
| 2007/0071740 A1 | 3/2007 | Tseng et al. | |
| 2007/0116684 A1 | 5/2007 | Atala et al. | |
| 2007/0134210 A1 | 6/2007 | Heidaran | |
| 2007/0134261 A1 | 6/2007 | Hancock et al. | |
| 2007/0178159 A1 | 8/2007 | Chen et al. | |
| 2007/0231297 A1 | 10/2007 | Smith et al. | |
| 2007/0275362 A1 | 11/2007 | Edinger et al. | |
| 2008/0044848 A1 | 2/2008 | Heidaran | |
| 2008/0046095 A1 | 2/2008 | Daniel | |
| 2008/0069895 A1 | 3/2008 | Liu et al. | |
| 2008/0131522 A1 | 6/2008 | Liu et al. | |
| 2008/0138396 A1 | 6/2008 | Low et al. | |
| 2008/0145344 A1 | 6/2008 | Deshpande et al. | |
| 2008/0152629 A1 | 6/2008 | Edinger et al. | |
| 2008/0175824 A1 | 7/2008 | Heidaran et al. | |
| 2008/0181935 A1 | 7/2008 | Bhatia | |
| 2008/0181967 A1 | 7/2008 | Liu et al. | |
| 2008/0193554 A1 | 8/2008 | Dua et al. | |
| 2008/0213332 A1 | 9/2008 | Slavin et al. | |
| 2008/0226595 A1 | 9/2008 | Edinger et al. | |
| 2008/0299087 A1 | 12/2008 | Tseng et al. | |
| 2009/0104164 A1 | 4/2009 | Zhang et al. | |
| 2009/0169597 A1 | 7/2009 | Brown et al. | |
| 2009/0252710 A1 | 10/2009 | Zhang et al. | |
| 2010/0047351 A1 | 2/2010 | Zeitlin et al. | |
| 2010/0098743 A1 | 4/2010 | Nikaido et al. | |
| 2010/0119496 A1 | 5/2010 | Wilkison et al. | |
| 2010/0260847 A1 | 10/2010 | Hariri | |
| 2011/0206776 A1 | 8/2011 | Tom et al. | |
| 2011/0212063 A1 | 9/2011 | Tom et al. | |
| 2011/0212064 A1 | 9/2011 | Jansen et al. | |
| 2011/0212065 A1 | 9/2011 | Jansen et al. | |
| 2011/0212158 A1 | 9/2011 | Tom et al. | |
| 2011/0251566 A1 | 10/2011 | Zimnitsky et al. | |
| 2011/0256202 A1 | 10/2011 | Tom et al. | |
| 2012/0095455 A1 | 4/2012 | Rodmond et al. | |
| 2014/0037598 A1 | 2/2014 | Jansen et al. | |
| 2014/0127177 A1 | 5/2014 | Tom et al. | |
| 2014/0127317 A1 | 5/2014 | Jansen et al. | |
| 2014/0140966 A1 | 5/2014 | Tom et al. | |
| 2014/0160447 A1 | 6/2014 | Kobayashi et al. | |
| 2014/0294777 A1 | 10/2014 | Tom et al. | |
| 2014/0301986 A1 | 10/2014 | Tom et al. | |
| 2015/0010506 A1 | 1/2015 | Jansen et al. | |
| 2015/0010609 A1 | 1/2015 | Tom et al. | |
| 2015/0010610 A1 | 1/2015 | Tom et al. | |
| 2018/0360886 A1 | 12/2018 | Tom et al. | |
| 2020/0000853 A1 | 1/2020 | Tom et al. | |

FOREIGN PATENT DOCUMENTS

| | | |
|---|---|---|
| CA | 2790333 | 8/2011 |
| CA | 2790336 | 8/2011 |
| CA | 2790340 | 8/2011 |
| CA | 2790436 | 8/2011 |
| CA | 2948129 | 11/2015 |
| CA | 2948126 | 11/2016 |
| CA | 2948133 | 11/2016 |
| EP | 2536825 | 8/2011 |
| EP | 2536826 | 8/2011 |
| EP | 2702871 | 3/2014 |
| EP | 3139934 | 3/2017 |
| EP | 2536417 | 1/2018 |
| EP | 2536827 | 1/2018 |
| EP | 2536824 | 4/2018 |
| EP | 3345998 | 7/2018 |
| EP | 3351622 | 7/2018 |
| EP | 3351624 | 7/2018 |
| EP | 3351625 | 7/2018 |
| JP | 2016-566889 | 6/2017 |
| JP | 2017514876 | 6/2017 |
| JP | 2017514879 | 6/2017 |
| KR | 10-2016-7034113 | 12/2016 |
| KR | 20160147058 | 12/2016 |
| KR | 20170002572 | 1/2017 |
| SG | 11201609253 P | 12/2016 |
| WO | WO 98/37903 | 9/1998 |
| WO | WO 2005/001076 | 1/2005 |
| WO | WO 2005/007835 | 1/2005 |
| WO | WO 2005/021014 | 3/2005 |
| WO | WO 2006/016828 | 2/2006 |
| WO | WO 2006/071794 | 7/2006 |
| WO | WO 2006/094247 | 9/2006 |
| WO | WO 2007/023750 | 3/2007 |
| WO | WO 2007/079183 | 7/2007 |
| WO | WO 2007/079184 | 7/2007 |
| WO | WO 2008/146991 | 12/2008 |
| WO | WO 2008/151846 | 12/2008 |
| WO | WO 2008/156659 | 12/2008 |
| WO | WO 2009/120996 | 10/2009 |
| WO | WO 2009/132186 | 10/2009 |
| WO | WO 2011/074208 | 6/2011 |
| WO | WO 2011/103446 | 8/2011 |
| WO | WO 2011/103451 | 8/2011 |
| WO | WO 2011/103455 | 8/2011 |
| WO | WO 2011/103462 | 8/2011 |
| WO | WO 2011/103470 | 8/2011 |
| WO | WO 2011/103472 | 8/2011 |
| WO | WO 2015/171142 | 11/2015 |
| WO | WO 2015/171143 | 11/2015 |
| WO | WO 2015/171144 | 11/2015 |

OTHER PUBLICATIONS

Niknejad et al. "Properties of the Amniotic Membrane for Potential Use in Tissue Engineering" European Cells and Materials vol. 15, 2008 (pp. 88-99). (Year: 2008).*

(56) References Cited

OTHER PUBLICATIONS

Ketheesan et al., "The effect of cryopreservation on the immunogenicity of allogeneic cardiac valves." Cryobiology. 1996; 33:41-53.
Koob, T.J. et al: "Biological properties of dehydrated human amnion/chorion composite graft: implications for chronic wound healing". International Wound Journal. (2013); 10(5): 493-500.
Parolini et al., Concise review: isolation and characterization of cells from human term placenta: outcome of the first international Workshop on Placenta Derived Stem Cells. Stem Cells. 2008; 26(2):300-11.
Sonicini, M. et al., "Isolation and characterization of mesenchymal cells from human fetal membranes." *J Tissue Eng Regen Med.* 2007, 1:296-305.
Subbota et al., Abstracts 1 Cryobiology. 2006; 53:415.
"Grafix® Cellular Repair Matrix for the Treatment of Burns", Osiris Therapeutics, Inc., Mar. 1, 2012.
Adds et al., "Amniotic membrane grafts, "fresh" or frozen? A clinical and in vitro comparison," Br. J. Ophthalmol., 85 (8):905-907 (2001).
Aggarwal et al, "Human mesenchymal stem cells modulate allogeneic immune cell responses," Blood, 105:1815-1822 (2005).
Akle et al., "Immunogenicity of human amniotic epithelial cells after transplantation into volunteers," Lancet, 2 (8254):1003-1005 (1981).
Allen et al., "Periosteum: biology, regulation, and response to osteoporosis therapies," Bone, 35:1003-1012 (2004).
Allori et al., "Biological basis of bone formation, remodeling, and repair—part II: extracellular matrix," Tissue Eng. Part B Rev., 14(3):275-283 (2008).
Allori et al., "Biological Basis of Bone Formation, Remodeling, and Repair—Part I: Biochemical Signaling Molecules," Tissue Engineering: Part B, 14(3):259-273 (2008).
Asplin et al., "Differential regulation of the fibroblast growth factor (FGF) family by alpha(2)-macroglobulin: evidence for selective modulation of FGF-2-induced angiogenesis," Blood, 97(11):3450-3457 (2001).
Atanassov, W., J. Mazgalova, and R. Todorov, Use of amniotic membranes as biological dressings in contemporary treatment of bums. Ann Med Bum Club, 1994.
Babalola, et al., "Aggregation of dispersed human cytotrophoblastic cells: Lessons relevant to the morphogenesis of the placenta", Developmental Biology, Academic Press, Amsterdam, NL, vol. 137, No. 1, Jan. 1, 1990 (Jan. 1, 1990), pp. 100-108, XP024788328, ISSN: 0012-1606.
Bagot et al., "Reconstructed human epidermis: absence of Langerhans cells and failure to stimulate allogeneic lymphocytes in vitro," Clin. Exp. Immunol., 71(1):138-143 (1988).
Bailo et al., "Engraftment potential of human amnion and chorion cells derived from term placenta," Transplantation, 78 (10):1439-1448 (2004).
Baker et al., "Metalloproteinase inhibitors: biological actions and therapeutic opportunities," J. Cell Sei., 115(Pt 19):3719-3727 (2002).
Bannasch et al., "Treatment of chronic wounds with cultured autologous keratinocytes as suspension in fibrin glue," Zentralbl Chir., 125 Suppl 1:79-81 (2000) (Abstract).
Barth et al., "Alpha 2-macroglobulin, a multifunctional binding protein with targeting characteristics," FASEB J., 6 (15):3345-3353 (1992).
Bergeson et al., "Fetal membrane collagens: Identification of two new collagen alpha chains," Proc. Natl. Acad. Sci. USA, 73(8):2579-2583 (1976).
Bertolami et al., "The Role of Proteoglycans in Hard and Soft Tissue Repair," Crit. Rev. Oral Biol. Med., 5 (3&4):311-337 (1994).
Bielby et al., "The role of mesenchymal stem cells in maintenance and repair of bone," Injury, Int. J. Care Injured, 38S1: S26-S32 (2007).
Branski, L.K., et al., Amnion in the treatment of pediatric partial-thickness facial bums. Burns, 2008. 34(3): p. 393-9.
Bravo et al., Effect of Storage on Preservation Methods on Viability in Transplantable Human Skin Allografts. Burns. 2000; 26:367-78.
Bruder et al., "Bone Regeneration by Implantation of Purified, Culture-Expanded Human Mesenchymal Stern Cells," J. Ortho. Res., 16:155-162 (1998).
Bruder et al., "Mesenchymal Stern Cells in Osteobiology and Applied Bone Regeneration," Clin. Ortho. Rei. Res., 355S:S247-S256 (1998).
Bryant-Greenwood, G.D., The extracellular matrix of the human fetal membranes: structure and function. Placenta, 1998. 19(1): p. 1-11.
Carter et al., "Immunolocalization of collagen types I and III, tenascin, and fibronectin in intramembranous bone," J. Histochem. Cytochem., 39(5):599-606 (1991).
Chang et al., "Rotator cuff repair with periosteum for enhancing tendon-bone healing: a biomechanical and histological study in rabbits," Knee Surg. Sports Traumatol. Arthrose., 17(12):1447-1453 (2009).
Chen et al., "Enveloping of periosteum on the hamstring tendon graft in anterior cruciate ligament reconstruction," Arthroscopy, 18(5):27E (2002).
Chen et al., "Enveloping the tendon graft with periosteum to enhance tendon-bone healing in a bone tunnel: A biomechanical and histologic study in rabbits," Arthroscopy, 19(3):290-296 (2003).
Chen et al., "Hypoxia and transforming growth factor-beta 1 act independently to increase extracellular matrix production by placental fibroblasts," J. Clin. Endocrinol. Metab., 90(2):1083-1090 (2005).
Chen, L., et al., Paracrine factors of mesenchymal stem cells recruit macrophages and endothelial lineage cells and enhance wound healing. PLoS One, 2008. 3(4): p. e1886.
Choi et al: "Full-Thickness Skin Wound Healing Using Human Placenta-Derived Extracellular Matrix Containing Bioactive Molecules", Tissue Engineering Part A, (2013); 19(3&4):329-339.
Clarke, "Normal Bane Anatomy and Physiology," Clin. J. Am. Soc. Nephrol., 3:S131-S139 {2008).
Communication Pursuant to Article 94(3) EPC dated Jul. 2, 2018 by the European Patent Office for Patent Application No. 14891336.1, which was filed on May 7, 2014 and published as EP 3139935 on Mar. 15, 2017 (Inventor—Jansen et al.; Applicant—Osiris Therapeutics, Inc.) (5 pages).
Communication Pursuant to Article 94(3) EPC dated Jul. 24, 2018 by the European Patent Office for Patent Application No. 117 45360.5, which was filed on Feb. 18, 2011 and published as EP 2536826 on Dec. 26, 2012 (Inventor—Jansen et al.; Applicant—Osiris Therapeutics, Inc.) (5 pages).
Communication Pursuant to Article 94(3) EPC dated Jun. 13, 2018 by the European Patent Office for Patent Application No. 14891208.2, which was filed on May 7, 2014 and published as EP 3139934 on Mar. 15, 2017 (Inventor—Tom et al.; Applicant—Osiris Therapeutics, Inc.) (4 pages).
Communication Pursuant to Article 94(3) EPC dated Jun. 15, 2018 by the European Patent Office for Patent Application No. 14891554.9, which was filed on May 7, 2014 and published as EP 3139936 on Mar. 15, 2017 (Inventor—Tom et al.; Applicant—Osiris Therapeutics, Inc.) (7 pages).
Communication Pursuant to Article 94(3) EPC dated Jun. 29, 2018 by the European Patent Office for Patent Application No. 117 4534 7.2, which was filed on Feb. 18, 2011 and published as EP 2536825 on Dec. 26, 2012 (Inventor—Tom et al.; Applicant—Osiris Therapeutics, Inc.) (4 pages).
Communication pursuant to Article 94(3) EPC was dated Nov. 4, 2016 by the European Patent Office for EP Application No. 11745360.5 dated Feb. 18, 2011 and published as 2536826 on Dec. 26, 2012 (Applicant—Osiris Therapeutics, Inc.; Applicant—Timothy Jansen et al) (5 Pages).
Communication pursuant to Article 94(3) EPC was dated Jul. 20, 2017 by the European Patent Office for EP Application No. 11745347.2, which was filed on Feb. 18, 2011 and published as EP 2536825 on Dec. 26, 2012 (Applicant—Osiris Therapeutics, Inc.) 15 pagess).
Communication pursuant to Article 94(3) EPC was dated Jul. 24, 2019 by the European Patent Office for EP Application No. 11745360.5, which was filed on Feb. 18, 2011 and published as EP 2536826 on Dec. 26, 2012 (Applicant—Osiris Therapeutics, Inc.) (3 pages).

(56) References Cited

OTHER PUBLICATIONS

Communication pursuant to Rules 161 (2) and 162 EPC was dated Dec. 15, 2016 by the European Patent Office for EP Application No. 14891208.2 dated May 7, 2014 (Applicant—Osiris Therapeutics, Inc.; Applicant—Timothy Jansen et all (5 Pages).
Communication pursuant to Rules 161 (2) and 162 EPC was dated Dec. 16, 2016 by the European Patent Office for EP Application No. 14891336.1 dated May 7, 2014 (Applicant—Osiris Therapeutics, Inc.; Applicant—Timothy Jansen et al) (2 Pages).
Communication pursuant to Rules 161 (2) and 162 EPC was dated Dec. 20, 2016 by the European Patent Office for EP Application No. 14891554.9 dated May 7, 2014 and published as 3139936 on Mar. 15, 2017 (Applicant—Osiris Therapeutics, Inc.; Applicant—Timothy Jansen et al) (2 pages).
Communication und er Rule 71 (3) EPC dated May 22, 2017 by the European Patent Office for European Patent Application No. 11745361. 3, which was filed an Feb. 18, 2011 and published as 2536827 an Dec. 26, 2012 (Inventar—Tom et al.; Applicant—Osiris Therapeutics, Inc.) (66 pages).
Database WPI Week 200522, Thomson Scientific. London. GB; AN 2005-214449; XP-002774389.
Davis, J.W., Skin transplantation with a review of 550 cases at the Johns Hopkins Hospital. Johns Hopkins Med J, 1910. 15.
De Rotth, "Plastic repair of conjunctival defects with fetal membranes," Arch. Ophthalmol., 23:522-525 (1940).
Devescovi et al., "Growth factors in bone repair," Chir. Organi. Mov., 92:161-168 (2008).
Dickinson et al., "Monoclonal anti-TNF-alpha suppresses graft vs hast disease reactions in an in vitro human skin model," Cytokine, 6(2):141-146 (1994).
Dioguardi, D., E. Brienza, and M. De Robertis, Skin Substitutes in bum treatment—our experience. Ann Med Bum Club, 1990.
Dua, Harminder S; Azuara-Blanco, Augusto; "Amniotic membrane transplantation" British Journal of Ophthalmology, 83, 748-752,(1999).
Dwek, "The periosteum: what is it, where is it, and what mimics it in its absence?" Skeletal Radial., 39:319-323 {2010).
E. Dimitriadis: "Cytokines, Chemokines and Growth Factors in Endometrium Related to Implantation", Human Reproduction Update, Val. 11, No. 6, Aug. 25, 2005 (Aug. 25, 2005), pp. 613-630, ISSN: 1355-4786, DOI: 10.10931 humupd/dmi023.
Eldad, A; et al; "Amniotic membranes as a biological dressing" South African Medical Journal, 51, 272-275,(1977).
Examination Report issued in Corresponding European Application No. 11745347.2, dated Apr. 23, 2020.
Examination Report dated Aug. 30, 2016 by the Canadian Intellectual Property Office for application CA 279036, filed on Feb. 18, 2011 (Inventor—Jansen, et al; Applicant—Osiris Therapeutics, Inc.) (5 pages).
Examination Report dated Aug. 31, 2016 by the Canadian Intellectual Property Office for application CA 2790333, filed on Feb. 18, 2011 (Inventor—Jansen, et al; Applicant—Osiris Therapeutics, Inc.) (5 pages).
Examination Report dated Sep. 19, 2016 by the Canadian Intellectual Property Office for application CA 2790340, filed on Feb. 18, 2011 (Inventor—Jansen, et al; Applicant—Osiris Therapeutics, Inc.) (6 pages).
Extended European Search Report and Written Opinion dated Oct. 17, 2017 by the European Patent Office for EP Patent Application No. 14891554.9, which was filed on May 7, 2014 and published as EP 3139936 on Mar. 15, 2017(Applicant—Osiris Therapeutics, Inc.) (13 pages).
Extended European Search Report and Written Opinion dated Oct. 13, 2017 by the European Patent Office for EP Patent Application No. 14891208.2, which was filed on May 7, 2014 and published as EP 3139934 on Mar. 15, 2017(Applicant—Osiris Therapeutics, Inc.) (7 pages).
Extended European Search Report and Written Opinion dated Oct. 13, 2017 by the European Patent Office for EP Patent Application No. 14891336.1, which was filed on May 7, 2014 and published as EP 3139935 on Mar. 15, 2017(Applicant—Osiris Therapeutics, Inc.) (7 pages).
Extended European Search Report dated Apr. 1, 2014 for application EP 11745341, filed on Feb. 18, 2011 and published as EP 2536824 on Dec. 26, 2012 (Applicant—Osiris Therapeutics, Inc.) (6 pages).
Extended European Search Report dated Apr. 1, 2014 for application EP 11745343, filed on Feb. 18, 2011 and published as EP 2536823 on Dec. 26, 2012 (Applicant—Osiris Therapeutics, Inc.) (6 pages).
Extended European Search Report dated Apr. 24, 2014 for application EP 11745347, filed on Feb. 18, 2011 and published as EP 2536825 on Dec. 26, 2012 (Applicant—Osiris Therapeutics, Inc.) (12 pages).
Extended European Search Report dated Apr. 24, 2014 for application EP 11745353, filed on Feb. 18, 2011 and published as EP 2536417 on Dec. 26, 2012 (Applicant—Osiris Therapeutics, Inc.) (10 pages).
Extended European Search Report dated Apr. 24, 2018 by the European Patent Office for Patent Application No. 17211013.2, which was filed on Dec. 29, 2017 (Inventor—Tom et al.; Applicant—Osiris Therapeutics, Inc.) (10 pages).
Extended European Search Report dated Apr. 29, 2014 for application EP 11745360, filed on Feb. 18, 2011 and published as EP 2536826 on Dec. 26, 2012 (Applicant—Osiris Therapeutics, Inc.) (10 pages).
Extended European Search Report dated May 24, 2018 by the European Patent Office for Patent Application No. 17207766.1, which was filed on Dec. 15, 2017 (Inventor—Tom et al.; Applicant—Osiris Therapeutics, Inc.) (9 pages).
Extended European Search Report dated May 25, 2018 by the European Patent Office for Patent Application No. 17211018.1, which was filed on Dec. 29, 2017 (Inventor—Jansen et al.; Applicant—Osiris Therapeutics, Inc.) (11 pages).
Extended European Search Report dated May 4, 2018 by the European Patent Office for Patent Application No. 17205385.2, which was filed on Dec. 5, 2017 (Inventor—Tom et al.; Applicant—Osiris Therapeutics, Inc.) (8 pages).
Extended European Search Report dated May 9, 2014 for application EP 11745361, filed on Feb. 18, 2011 and published as EP 2536827 on Dec. 26, 2012 (Applicant—Osiris Therapeutics, Inc.) (8 pages).
Fan et al., "Synovium-Derived Mesenchymal Stern Cells: A New Cell Source for Musculoskeletal Regeneration," Tissue Engineering: Part B, 15{1 ):75-86 (2009).
Final Office Action dated Apr. 21, 2017 by the U.S. Patent and Trademark Office for U.S. Appl. No. 14/056,101, filed Oct. 17, 2013 and published as US 2014/0037598 an Feb. 6, 2014 (Inventor—Jansen et al.; Applicant—Osiris Therapeutics, Inc.) (13 pages).
Final Office Action dated May 5, 2017 by the U.S. Patent and Trademark Office for U.S. Appl. No. 14/069,894, filed Nov. 1, 2013 and published as US 2014/0140966 an May 22, 2014 (Inventor—Tom et al.; Applicant—Osiris Therapeutics, Inc.) (18 pages).
Final Office Action issued on 2117/2017 for U.S. Appl. No. 14/070,040, filed Nov. 1, 2013 (Applicant—Osris therapeutics, Inc. //Inventor—Tom, et al.) (12 pages).
Final Office Action dated Feb. 5, 2019 by the U.S. Patent and Trademark Office for U.S. Appl. No. 14/056,101, filed Oct. 17, 2013 and published as US 2014/0037598 on Feb. 6, 2014 (Inventar—Jansen et al.; Applicant—Osiris Therapeutics, Inc.) (14 pages).
Final Office Action dated Jul. 26, 2018 by the U.S. Patent and Trademark Office for U.S. Appl. No. 14/172,940, filed Feb. 5, 2014 and published as US 2014/0294777 on Oct. 2, 2014 (Inventor—Tom et al..; Applicant—Osiris Therapeutics, Inc.) (20 pages).
Final Office Action dated May 9, 2017 by the U.S. Patent and Trademark Office for U.S. Appl. No. 14/291,256, filed May 30, 2014 and published as US 2014/0301986 on Oct. 9, 2014 (Inventor—Tom et al.; Applicant—Osiris Therapeutics, Inc.) (22 pages).
Final Office Action dated Nov. 30, 2015 for U.S. Appl. No. 14/070,040, filed Nov. 1, 2013 (Applicant—Osris therapeutics, Inc. //Inventor—Tom, et al.) (11 pages).

(56) References Cited

OTHER PUBLICATIONS

Final Office Action was dated Jul. 14, 2017 by the USPTO for U.S. Appl. No. 14/272,343, filed May 7, 2014 and published as US 2015/0010609 A1 on Jan. 8, 2015 (Applicant—Osiris Therapeutics, Inc.; Inventor—Samson Tom) (19 pages).
Final Office Action was dated Jul. 14, 2017 bythe USPTO for U.S. Appl. No. 14/272,345, filed May 7, 2014 and published as US 2015/0010610 A1 on Jan. 8, 2015 (Applicant—Osiris Therapeutics, Inc.; Inventor—Samson Tom) (18 pages).
Final Office Action was dated Jul. 21, 2017 bythe USPTO for U.S. Appl. No. 14/272,339, filed May 7, 2014 and published as US 2015/0010506 A1 on Jan. 8, 2015 (Applicant—Osiris Therapeutics, Inc.; Inventor—Samson Tom) (16 pages).
Final Rejection was dated Jan. 10, 2017 by the U.S. Patent and Trademark Office for U.S. Appl. No. 14/172,940, filed Feb. 5, 2014 and published as US 2014-0294777 A1 on Oct. 2, 2014 (Applicant—Osiris Therapeutics, Inc.; Applicant—Samson Tom et al.) (19 pages).
Final Rejection was dated Feb. 17, 2017 by the U.S. Patent and Trademark Office for U.S. Appl. No. 14/070,040, filed Nov. 1, 2013 and published as US 2014-0127177A1 on May 8, 2014 (Applicant—Osiris Therapeutics, Inc.) (12 pages).
Fortunato et al., "I. Organ Culture of Amniochorionic Membrane In Vitro," Am. J. Reprod. Immunol., 32:184-187 (1994).
Fortunato et al., "Inflammatory cytokine (interleukins 1, 6 and 8 and tumor necrosis factor-alpha) release from cultured human fetal membranes in response to endotoxic lipopolysaccharide mirrors amniotic fluid concentrations," Am. J. D Obstet. Gynecol., 174(6):1855-1861 (1996).
Gajiwala, K. and A. Lobo Gajiwala, Use of banked tissue in plastic surgery. Cell Tissue Bank, 2003. 4(2-4): p. 141-6.
Gajiwala, K. and A.L. Gajiwala, Evaluation of lyophilised, gamma-irradiated amnion as a biological dressing. Cell Tissue Bank, 2004. 5(2): p. 73-80.
Galiano et al., "Interaction between the insulin-like growth factor family and the integrin receptor family in tissue repair processes. Evidence in a rabbit ear dermal ulcer model," J. Clin. Invest., 98(11 ):2462-2468 (1996).
Ganatra, M.A. and K.M. Durrani, Method of obtaining and preparation of fresh human amniotic membrane for clinical use. J Pak Med Assoc, 1996. 46(6): p. 126-8.
Genbacev, Olga; et al; "Serum-free derivation of human embryonic stem cell lines on human placental fibroblast feeders" Fertility and Sterility, 83, 1517-1529,(2005).
Goldman, "Growth factors and chronic wound healing: past, present, and future," Adv. Skin Wound Care, 17:24-35 (2004).
Greenhalgh et al., "PDGF and FGF stimulate wound healing in the genetically diabetic mouse," Am. J. Pathol., 136 (6):1235-1246 (1990).
Haberal, M., et al., The use of silver nitrate-incorporated amniotic membrane as a temporary dressing. Burns Incl Therm Inj, 1987. 13(2): p. 159-63.
Hacking, A.M. and N.S. Gibran, Mesenchymal stem cells: paracrine signaling and differentiation during cutaneous wound repair. Exp Cell Res. 316(14): p. 2213-9.
Hadjiiski, 0. and N. Anatassov, Amniotic membranes for temporary bum coverage. Ann Bums Fire Disasters, 1996.
Hang et al., "The effect of various concentrations of human recombinant epidermal growth factor on split-thickness skin wounds," Int. Wound J., 3:123-130 (2006).
Hieber, A.D., et al., Detection of elastin in the human fetal membranes: proposed molecular basis for elasticity. Placenta, 1997. 18(4): p. 301-12.
Huang et al., "Human transforming growth factor beta.alpha 2-macroglobulin complex is a latent form of transforming growth factor beta," J. Biol. Chem., 263(3):1535-1541 (1988).
Hutmacher et al., "Periosteal Cells in Bane Tissue Engineering," Tissue Engineering, 9(Supp 1 ):S-45-8-64 (2003).
Ilancheran et al., "Human fetal membranes: a source of stem cells for tissue regeneration and repair?" Placenta, 30:2-10 (2009).

Intention to Grant dated Jan. 26, 2018 by the European Patent Office for Patent Application No. 11745341.5, which was filed on Feb. 18, 2011 and published as EP 2536824 on Dec. 26, 2012 (Inventor—Tom et al.; Applicant—Osiris Therapeutics, Inc.) (8 pages).
International Preliminary Report on Patentability mailed by the International Searching Authority dated Nov. 8, 2016 for application PCT/US2014/037204, filed on May 7, 2014 (Applicant—Osiris Therapeutics, Inc. // Inventor—Samson, Tom, et al.) (18 pages).
International Preliminary Report on Patentability mailed by the International Searching Authority dated Nov. 8, 2016 for application PCT/US2014/037208, filed on May 7, 2014 (Applicant—Osiris Therapeutics, Inc. // Inventor—Samson, Tom, et al.) (17 pages).
International Preliminary Report on Patentability mailed by the International Searching Authority dated Nov. 8, 2016 for application PCT/US2014/037201, filed on May 7, 2014 (Applicant—Osiris Therapeutics, Inc. // Inventor—Samson, Tom, et al.) (18 pages).
International Search Report and Written Opinion in PCT/US11/25459, dated May 3, 2011.
International Search Report and Written Opinion in PCT/US11/25465, dated Apr. 14, 2011.
International Search Report and Written Opinion in PCT/US11/25469, dated Apr. 27, 2011.
International Search Report and Written Opinion in PCT/US11/25478, dated May 25, 2011.
International Search Report and Written Opinion in PCT/US11/25490, dated Apr. 13, 2011.
International Search Report and Written Opinion in PCT/US11/25498, dated May 4, 2011.
International Search Report and Written Opinion mailed by the International Searching Authority dated Sep. 29, 2014 for application PCT/US2014/037208, filed on May 7, 2014 (Applicant—Osiris Therapeutics, Inc. II Inventor—Samson Tom, et al.) (19 pages).
International Search Report mailed by the International Searching Authority dated Sep. 29, 2014 for application PCT/US2014/037204, filed on May 7, 2014 (Applicant—Osiris Therapeutics, Inc. // Inventor—Samson, Tom, et al.) (2 pages).
International Search Report mailed by the International Searching Authority dated Sep. 29, 2014 for application PCT/US2014/037201, filed on May 7, 2014 (Applicant—Osiris Therapeutics, Inc. // Inventor—Samson, Tom, et al.) (3 pages).
Int'l Prelim. Report on Patentability in PCT/US2011/025459 dated Aug. 30, 2012.
Int'l Prelim. Report on Patentability in PCT/US2011/025465 dated Aug. 30, 2012.
Int'l Prelim. Report on Patentability in PCT/US2011/025469 dated Aug. 30, 2012.
Int'l Prelim. Report on Patentability in PCT/US2011/025478 dated Aug. 30, 2012.
Int'l Prelim. Report on Patentability in PCT/US2011/025490 dated Aug. 30, 2012.
Int'l Prelim. Report on Patentability in PCT/US2011/025493 dated Aug. 30, 2012.
Int'l Search Report and Written Opinion in PCT/US2011/025493 dated May 4, 2011.
Izumi et al., "Mortality of first-time amputees in diabetics: a 10-year observation," Diabetes Res. Clin. Pract., 83:126-131 (2009).
Jordan et al., "Optimal analysis of composite cytokine responses during alloreactivity," J. Immunol. Methods, 260:1-14 (2002).
Kasi, N., K.M. Durrani, and M.A. Siddiqui, Human amniotic membrane as a versatile biological dressing—a preliminary report. J Pak Med Assoc, 1987. 37(11 ): p. 290-2.
Kawai et al., "Effects of adiponectin on growth and differentiation of human keratinocytes-implication of impaired wound healing in diabetes," Biochem. Biophys. Res. Commun., 374:269-273 (2008).
Keene et al., "Human bone contains type III collagen, type VI collagen, and fibrillin: type III collagen is present on specific fibers that may mediate attachment of tendons, ligaments, and periosteum to calcified bone cortex," J. Histochem. Cytochem., 39:59-69 (2011).
Kesting et al., "The role of allogenic amniotic membrane in burn treatment," J. Burn Care Res., 29:907-916 (2008).

(56) References Cited

OTHER PUBLICATIONS

Kim et al., "Coexpression of myofibroblast and macrophage markers: novel evidence for an in vivo plasticity of chorioamniotic mesodermal cells of the human placenta," Lab Invest., 88:365-374 (2008).
Komarcevic et al., "New views on the physiology of wound healing," Med. Pregl., 53(9-10):479-483 (Abstract) (2000).
Komatsu et al., "The Control of Fracture Healing and Its Therapeutic Targeting: Improving Upon Nature," J. Cell. Biochem., 109:302-311 (2010).
Kruse F. E. et al: Cryopreserved Human Amniotic Membrane for Ocular Surface Reconstruction, Graefe's Archive for Clinical and Experimental Ophthalmology, Springer Verlag, DE, Val. 238, No. 1, Jan. 1, 2000 (Jan. 1, 2000), pp. 68-75, XP999923120, ISSN: 9721-B32X, 001: 19. 1997/8994179959912.
Kuba et al., "Immunogenicity of human amniotic membrane in experimental xenotransplantation" Invest Ophthalmol Vis Sci. Jun. 2001;42(7):1539-46.
Kwan et al., "Scar and contracture: biological principles," Hand Clin., 25:511-528 (2009).
Ley-Chavez, E., et al., Application of biological dressings from radiosterilized amnios with cobalt 60 and serologic studies on the handling of burns in pediatric patients. Ann Transplant, 2003. 8(4): p. 46-9.
Li, H; et al; "Hypoxia-induced Increase in Soluble Flt-1 Production Correlates with Enhanced Oxidative Stress in Trophoblast Cells from the Human Placenta" Placenta, 26, 210-217,(2005).
Lin, S.O., et al., Amnion overlay meshed skin auto graft. Burns Incl Therm Inj, 1985. 11(5): p. 374-8.
Liu et al., "Increased matrix metalloproteinase-9 predicts poor wound healing in diabetic foot ulcers," Diabetes Care, 32:117-119 (2009).
Livingston et al., "Mesenchymal stem cells combined with biphasic calcium phosphate ceramics promote bone regeneration," J. Mat. Sci.: Mat. Med., 14:211-218 (2003).
Lomas et al., "Application of a high-level peracetic acid disinfection protocol to reprocess antibiotic disinfected skin allografts," Cell Tissue Bank, 5:23-36 (2004).
Lorusso, R., V. Geraci, and M. Masellis, The treatment of superficial burns with biological and synthetic material: frozen amnion and biobrane. Ann Med Burn Club, 1989.
Lue et al., "Engagement of CD14 on human monocytes terminates T cell proliferation by delivering a negative signal to T cells," J. Immunol., 147(4):1134-1138 (1991).
Maddalena Soncini et al: "Isolation and characterization of mesenchymal cells from human fetal membranes", Journal of Tissue Engineering and Regenerative Medicine, (2007) 1 :296-305.
Magatti et al., "Human amnion mesenchyme harbors cells with allogeneic T-cell suppression and stimulation capabilities," Stern Cells, 26:182-192 (2008).
Magliacani, G., The surgical treatment of burns: skin substitutes. Ann Med Burn Club, 1990.
Majors et al., "Characterization of human bone marrow stromal cells with respect to osteoblastic differentiation," J. Orthop. Res., 15:546-557 (1997).
Malak et al., "Confocal immunofluorescence localization of collagen types I, III, IV, V and VI and their ultrastructural organization in term human fetal membranes," Placenta, 14(4):385-406 (1993).
Malhotra et al., Human amniotic membrane transplantation: Different modalities of its use in ophthalmology. World J. Transplant, Jun. 24, 2014; 4(2); 111-121.
Malizos et al., "The healing potential of the periosteum Molecular aspects," Injury, Int. J. Care Injured, 36S-S 13-S 19 (2005).
Mathew, S., et al., "Characterization of the interaction between α2macroglobulin and fibroblast growth factor-2: the role of hydrophobic interactions", Dept. of Pathology, pp. 123-129.
Meiler, D. et al., Amniotic Membrane Transplantation in the Human Eye. Dtsch Arztebl Int. 2011; 108(14) :243-8.
Meinert et al., "Proteoglycans and hyaluronan in human fetal membranes," Am. J. Obstet. Gynecol., 184(4):679-685 (2001).

Midura et al., "Parathyroid Hormone Rapidly Stimulates hyaluronan Synthesis by Periosteal Osteoblasts in the Tibial Diaphysis of the Growing Rat," J. Biol. Chem., 278(51):51462-51468 (2003).
Mwaura et al., "The impact of differential expression of extracellular matrix metalloproteinase inducer, matrix metalloproteinase-2, tissue inhibitor of matrix metalloproteinase-2 and PDGF-AA on the chronicity of venous leg ulcers," Eur. J. Vase. Endovasc. Surg., 31:306-310 (2006).
Nauth et al., "Bone morphogenetic proteins in open fractures: past, present, and future," Injury, Int. J. Care Injured, 40: S3, S27-S31 (2009).
Nedelec et al., "The effect of interferon alpha 2b on the expression of cytoskeletal proteins in an in vitro model of wound contraction," J. Lab. Clin. Med., 126:474-484 (1995).
Niknejad et al. "Properties of the Amniotic Membrane for Potential Use in Tissue Engineering" European Cells and Materials, (2008)15: 88-99.
Non Final dated Oct. 19, 2017 by the USPTO for U.S. Appl. No. 14/172,940, which was filed on 2/512014 and published as US 2014-0294777A1 on Oct. 2, 2014(Applicant—Osiris Therapeutics, Inc.; Inventor—Samson Tom) (22 pages).
Non Final Rejection was dated Nov. 1, 2017 by the U.S. Patent and Trademark Office for U.S. Appl. No. 14/272,343, filed May 17, 2014 and published as US 2015-0010609 A1 on Jan. 8, 2015 (Applicant—Osiris Therapeutics, Inc.; Applicant—Samson Tom et al.) (17 Pages).
Non Final Rejection was dated May 19, 2016 by the U.S. Patent and Trademark Office for U.S. Appl. No. 14/172,940, filed Feb. 5, 2014 and published US-2014-0294777-A1 on Oct. 2, 2014 (Inventor—Samson Tom et al; Applicant—Osiris Therapeutics, Inc.) (20 pages).
Non Final Rejection was dated Jun. 27, 2016 by the U.S. Patent and Trademark Office for U.S. Appl. No. 14/069,894, filed Nov. 11, 2013 and published US 2014-0140966A1 on May 22, 2014 (Inventor—Samson Tom et al; Applicant—Osiris Therapeutics, Inc.) (13 pages).
Non Final Rejection was dated Jun. 30, 2016 by the U.S. Patent and Trademark Office for U.S. Appl. No. 14/056,101, filed Oct. 17, 2013 and published US 2014-0037598A1 on Feb. 6, 2014 (Inventor—Timothy Jansen et al; Applicant—Osiris Therapeutics, Inc.) (13 pages).
Non Final Rejection was dated Aug. 27, 2019 by the USPTO for U.S. Appl. No. 15/949,808, filed Apr. 10, 2018 and published as US 2018-0360886A1 on Dec. 20, 2018 (Inventor—Samson Tom)(9 pages).
Non-Final Office Action issued by the U.S. Patent & Trademark Office dated Mar. 10, 2015, for U.S. Appl. No. 14/070,040, filed Nov. 1, 2013 and published as US 2014-0127177 A1 on May 8, 2014 (Inventor—Tom, et al. II Applicant—Osiris Therapeutics, Inc.) (13 pages).
Non-Final Office Action dated Aug. 18, 2016 for U.S. Appl. No. 14/070,040, filed Nov. 1, 2013 and published as US 2014-0127177A1 on May 8, 2014 (Inventor—Tom, et al; Applicant—Osiris Therapeutics, Inc.) (13 pages).
Non-Final Office Action dated Aug. 25, 2016 for U.S. Appl. No. 14/291,256, filed May 30, 2014 and published US 2014-0301986A1 on Oct. 9, 2014 (Inventor—Tom, et al; Applicant—Osiris Therapeutics, Inc.) (19 pages).
Non-Final Office Action dated Dec. 15, 2016 by the U.S. Patent and Trademark Office for U.S. Appl. No. 14/272,345, filed May 7, 2014 and published US 2015-0010610 A1 on Jan. 8, 2015 (Inventor—Tom, et al; Applicant—Osiris Therapeutics, Inc.) (pp. 1-16).
Non-Final Office Action dated Dec. 19, 2016 by the U.S. Patent and Trademark Office for U.S. Appl. No. 14/272,339, filed May 7, 2014 and published US 2015-0010506 A1 on Jan. 8, 2015 (Inventor—Jansen, et al; Applicant—Osiris Therapeutics, Inc.) (13 pages).
Non-Final Office Action dated Feb. 23, 2018 by the U.S. Patent and Trademark Office for U.S. Appl. No. 141272,343, filed May 7, 2014 and published as US 201510010609 on Jan. 8, 2015 (Inventor—Tom et al.; Applicant—Osiris Therapeutics, Inc.) (13 pages).
Non-Final Office Action dated Feb. 23, 2018 by the U.S. Patent and Trademark Office for U.S. Appl. No. 141291,256, filed May 30, 2014 and published as US 201410301986 on Oct. 9, 2014 (Inventor—Tom et al.; Applicant—Osiris Therapeutics, Inc.) (25 pages).

(56) References Cited

OTHER PUBLICATIONS

Non-Final Office Action dated Feb. 23, 2018 by the U.S. Patent and Trademark Office for U.S. Appl. No. 141069,894, filed Nov. 1, 2013 and published as US 201410140966 on May 22, 2014 (Inventor—Tom et al.; Applicant—Osiris Therapeutics, Inc.) (16 pages).
Non-Final Office Action dated Mar. 26, 2018 by the U.S. Patent and Trademark Office for U.S. Appl. No. 14/272,345, filed May 7, 2014 and published as US 2015/0010610 on Jan. 8, 2015 (Inventor—Tom et al.; Applicant—Osiris Therapeutics, Inc.) (18 pages).
Non-Final Office Action dated May 17, 2018 by the U.S. Patent and Trademark Office for U.S. Appl. No. 14/056,101, filed Oct. 17, 2013 and published as US 2014/0037598 on Feb. 6, 2014 (Inventor—Jansen et al.; Applicant—Osiris Therapeutics, Inc.) (14 pages).
Notice of Allowance dated Jan. 10, 2018 by the USPTO for U.S. Appl. No. 14/070,040, filed Nov. 1, 2013 and published as US 2014/0127177 on May 8, 2014 (Applicant—Osiris Therapeutics, Inc.; Inventor—Samson Tom) (8 pages).
Notice of Reason for Rejection dated Oct. 9, 2018 by the Intellectual Property Office of Japan for Patent Application No. 2016-567041, which was filed on Nov. 7, 2016 (Inventor—Tom et al.; Applicant—Osiris Therapeutics, Inc.) (Original—2 pages; Translation—2 pages).
Notice of Reasons for Rejection dated Feb. 27, 2018 by the Japanese Patent Office for Patent Application No. 2016-566997, which was filed on Nov. 7, 2016 (Inventor—Jansen et al.; Applicant—Osiris Therapeutics, Inc.) (Original—4 pages // Translation—4 pages).
Notice of Reasons for Rejection dated Feb. 6, 2018 by the Japanese Patent Office for Patent Application No. 2016-567041, which was filed on Nov. 7, 2016 (Inventor—Tom et al.; Applicant—Osiris Therapeutics, Inc.) (Original—2 pages // Translation—2 pages).
Notice of Reasons for Rejection dated Nov. 6, 2018 by the Intellectual Property Office of Japan for Patent Application No. 2016-566997, which was filed on Nov. 7, 2016 (Inventor—Jansen et al.; Applicant—Osiris Therapeutics, Inc.) (Original—3 pages; Translation—3 pages).
Occleston et al., "Prevention and reduction of scarring in the skin by Transforming Growth Factor beta 3 (TGFbeta3): from laboratory discovery to clinical pharmaceutical," J. Biomater. Sci. Polym. Ed., 19:1047-1063 (2008).
O'Driscoll et al., "The chondrogenic potential of periosteum decreases with age," J. Ortho. Res., 19:95-103 (2001).
Office Action in U.S. Appl. No. 13/030,507 dated Jan. 30, 2014.
Office Action in U.S. Appl. No. 13/030,507 dated Mar. 1, 2013.
Office Action in U.S. Appl. No. 13/030,539 dated Jun. 7, 2013.
Office Action in U.S. Appl. No. 13/030,562 dated Jul. 2, 2013.
Office Action in U.S. Appl. No. 13/030,580; dated Feb. 14, 2013.
Office Action in U.S. Appl. No. 13/030,580; dated May 17, 2013.
Office Action in U.S. Appl. No. 13/030,595; dated May 9, 2013.
Office Action in U.S. Appl. No. 13/030,539; dated Oct. 9, 2012.
Office Action in U.S. Appl. No. 13/030,562 dated Oct. 10, 2012.
Office Action issued in Corresponding Canadian Application No. 2,790,436, dated Jun. 23, 2020.
Office Action issued in Corresponding Canadian Application No. 2,790,336, dated May 15, 2020.
Office Action dated Apr. 30, 2019 by the Canadian Intellectual Property Office for CA Application No. 2,790,436, which was filed on Feb. 18, 2011 (Applicant—Osiris Therapeutics, Inc.) (6 pages).
Office Action dated Apr. 30, 2019 by the Canadian Intellectual Property Office for CA Application No. 2,790,325, which was filed on Feb. 18, 2011 (Applicant—Osiris Therapeutics, Inc.) (6 pages).
Office Action dated Apr. 5, 2018 by the Canadian Intellectual Property Office for Patent Application No. 2,790,436, which was filed on Aug. 17, 2012 (Inventor—Tom et al.; Applicant—Osiris Therapeutics, Inc.) (6 pages).
Office Action dated Apr. 5, 2018 by the Canadian Intellectual Property Office for Patent Application No. 2,790,325, which was filed on Aug. 17, 2012 (Inventor—Tom et al.; Applicant—Osiris Therapeutics, Inc.) (6 pages).
Office Action dated Dec. 15, 2017 by the Canadian Patent Office for Patent Application No. 2,790,333, which was filed on Aug. 17, 2012 (Inventor—Jansen et al.; Applicant—Osiris Therapeutics, Inc.) (5 pages).
Office Action dated Feb. 4, 2019 by the Canadian Intellectual Property Office for Patent Application No. 2,790,333, which was filed on Aug. 17, 2012 (Inventor—Jansen et al.; Applicant—Osiris Therapeutics, Inc.) (4 pages).
Office Action dated May 22, 2018 by the Japanese Patent Office for Patent Application No. 2016-566889, which was filed on Nov. 7, 2016 (Inventor—Tom et al.; Applicant—Osiris Therapeutics, Inc.) (Original—4 pages; Translation—5 pages).
Office Action was dated Jan. 24, 2017 by the Canadian Patent Office for CA Application No. 2,790,322, which was filed an Feb. 18, 2011 (Applicant—Osiris Therapeutics, Inc.; Applicant—Samson Tom et al.) (5 Pages).
Office Action was dated Jan. 25, 2017 by the Canadian Patent Office for CA Application No. 2,790,325, which was filed an Feb. 18, 2011 (Applicant—Osiris Therapeutics, Inc.; Applicant—Samson Tom et al.) (6 Pages).
Office Action was dated Jan. 24, 2017 by the International Searching Authority for International Application No. 2,790,436, which was filed on Feb. 18, 2011 (Applicant—Osiris Therapeutics, Inc.) (6 pages).
Office Action was dated Oct. 23, 2017 by the Canadian Patent Office for CA Application No. 2,790,336, which was filed on Feb. 18, 2011 (Applicant—Osiris Therapeutics, Inc.) (5 Pages).
Office Action was dated Oct. 30, 2017 by the Canadian Patent Office for CA Application No. 2,790,340, which was filed on Feb. 18, 2011 (Applicant—Osiris Therapeutics, Inc.) (4 Pages).
Ohashi et al., "Advanced glycation end products enhance monocyte activation during human mixed lymphocyte reaction," Clin. Immunol., 134:345-353 (2009).
Onishi et al., "Distinct and overlapping patterns of localization of bone morphogenetic protein (BMP) family members and a BMP type II receptor during fracture healing in rats," Bone, 22(6):605-612 (1998).
Page et al., "Critiquing clinical research of new technologies for diabetic foot wound management," J. Foot Ankle Surg., 41 (4):251-259 (2002).
Paquet-Fifield et al., "A role for pericytes as microenvironmental regulators of human skin tissue regeneration," J. Clin. Invest, 119:2795-2806 (2009).
Paradowska et al., "Constitutive and induced cytokine production by human placenta and amniotic membrane at term," Placenta, 18:441-446 (1997).
Parolini et al., "Concise review: isolation and characterization of cells from human term placenta: outcome of the first international workshop on placenta derived stem cells," Stern Cells, 26(2):300-311 (2008).
Pascher et al., "Biologies in the treatment of transplant rejection and ischemia/reperfusion injury," BioDrugs, 19 (4):211-231 (2005).
Pastar et al., "Role of keratinocytes in healing of chronic wounds," Surg. Technol. Int., 17:105-12 (2008).
Portmann-Lanz et al., "Isolation and characterization of mesenchymal cells from human fetal membranes," J. Tissue Eng. Regen. Med., 1(4):296-305 (2007).
Portmann-Lanz et al., "Placental mesenchymal stem cells as potential autologous graft for pre- and perinatal neuroregeneration," Am. J. Obstet. Gynecol., 194:664-673 (2006).
Presta et al., "Fibroblast growth factor/fibroblast growth factor receptor system in angiogenesis," Cytokine & Growth Factor Reviews, 16:159-178 (2005).
Rama, P. et al., Further Evaluation of Amniotic Membrane Banking for Transplantation in Ocular Surface Diseases. Cell Tissue Bank. 2001; 2(3) :155-63.
Ramakrishnan, K.M. and V. Jayaraman, Management of partialthickness burn wounds by amniotic membrane: a cost-effective treatment in developing countries. Burns, 1997. 23 Suppl 1: p. 833-6.
Rao, T.V. and V. Chandrasekharam, Use of dry human and bovine amnion as a biological dressing. Arch Surg, 1981. 116(7): p. 891-6.

(56) References Cited

OTHER PUBLICATIONS

Ravishanker, R., A.S. Bath, and R. Roy, "Amnion Bank"—the use of long term glycerol preserved amniotic membranes in the management of superficial and superficial partial thickness burns. Burns, 2003. 29(4): p. 369-74.
Requirement for Restriction or Election dated Aug. 24, 2016 by the U.S. Patent and Trademark Office for U.S. Appl. No. 14/272,33, filed May 7, 2014 and published US 2015-0010506 A1 on Jan. 8, 2015 (Inventor—Jansen, et al; Applicant—Osiris Therapeutics, Inc.) (10 pages).
Requirement for Restriction or Election dated Aug. 8, 2016 by the U.S. Patent and Trademark Office for U.S. Appl. No. 14/272,343, filed May 7, 2014 and published US-2015-0010609-A 1 on Jan. 8, 2015 (Inventor—Tom, et al; Applicant—Osiris Therapeutics, Inc.) (9 pages).
Requirement for Restriction or Election dated Aug. 9, 2016 by the U.S. Patent and Trademark Office for U.S. Appl. No. 14/272,345, filed May 7, 2014 and published US 2015-0010610 A1 on Jan. 8, 2015 (Inventor—Tom, et al; Applicant—Osiris Therapeutics, Inc.) (10 pages).
Response to Extended European Search Report filed on Dec. 3, 2014 for application EP 11745361, filed on Feb. 18, 2011 and published as EP 2536827 on Dec. 26, 2012 (Applicant—Osiris Therapeutics, Inc.) (14 pages).
Response to Extended European Search Report filed on Nov. 4, 2014 for application EP 11745353, filed on Feb. 18, 2011 and published as EP 2536417 on Dec. 26, 2012 (Applicant—Osiris Therapeutics, Inc.) (13 pages).
Response to Extended European Search Report filed on Nov. 5, 2014 for application EP 11745360, filed on Feb. 18, 2011 and published as EP 2536826 on Dec. 26, 2012 (Applicant—Osiris Therapeutics, Inc.) (15 pages).
Response to Extended European Search Report filed on Oct. 28, 2014 for application EP 11745341, filed on Feb. 18, 2011 and published as EP 2536824 on Dec. 26, 2012 (Applicant—Osiris Therapeutics, Inc.) (13 pages).
Response to Extended European Search Report filed on Oct. 29, 2014 for application EP 11745343, filed on Feb. 18, 2011 and published as EP 2536823 on Dec. 26, 2012 (Applicant—Osiris Therapeutics, Inc.) (14 pages).
Response to Extended European Search Report issued filed on Nov. 4, 2014 for application EP 11745347, filed on Feb. 18, 2011 and published as EP 2536825 on Dec. 26, 2012 (Applicant—Osiris Therapeutics, Inc.) (17 pages).
Restriction Requirement dated Feb. 11, 2016 for U.S. Appl. No. 14/056,101, filed Oct. 17, 2013 (Applicant—Osris therapeutics, Inc. //Inventor—Tom, et al.) (11 pages).
Reuss et al., "Fibroblast growth factors and their receptors in the central nervous system," Cell Tissue Res., 313:139-157 (2003).
Saksela, et al., "Presence of α2Macroglobulin in Normal but Not in Malignant Human Syncytiotrophoblasts" Dept. of Virology, Cancer Res. 41, 2507-2513, Jun. 1981.
Sangwan et al., "Treatment of uveitis: beyond steroids," Indian J. Ophthalmol., 58(1):1-2 (2009).
Sawhney, C.P., Amniotic membrane as a biological dressing in the management of bums. Burns, 1989. 15(5): p. 339-42.
Sekine et al., "Role of passenger leukocytes in allograft rejection: effect of depletion of donor alveolar macrophages on the local production of TNF-alpha, T helper 1/T helper 2 cytokines, IgG subclasses, and pathology in a rat model of lung transplantation," J. Immunol., 159:4084-4093 (1997).
Sen et al. "Oxygen, Oxidants, and Antioxidants in Wound Healing an Emerging Paradigm" Ann. 1-79 N.Y. Acad. Sci. May 1, 2002 (May 1, 2002), vol. 957, PQs. 239-249.
Shalaby et al., "The involvement of human tumor necrosis factors-alpha and -beta in the mixed lymphocyte reaction," J. Immunol., 141:499-503 (1988).
Shapiro, "Bone development and tis relation to fracture repair. The role of mesenchymal osteoblasts and surface osteoblasts," Eur. Cell. Mat., 15:53-76 (2008).

Shen et al., "IL-6 and TNF-Synergistically Inhibit Allograf! Acceptance," J. Am. Soc. Nephrol., 20:1032-1040 (2009).
Shimmura et al., "Antiinflammatory effects of amniotic membrane transplantation in ocular surface disorders," Cornea, 20{4 ):408-413 (2001).
Singh, R., et al., Microbiological safety and clinical efficacy of radiation sterilized amniotic membranes for treatment of second-degree bums. Burns, 2007. 33(4): p. 505-10.
Splichal, 1. and 1. Trebichavsky, Cytokines and other important inflammatory mediators in gestation and bacterial intraamniotic infections. Folia Microbiol (Praha). 2001. 46(4): p. 345-51.
Su et al., "Molecular profile of endothelial invasion of three-dimensional collagen matrices: insights into angiogenic sprout induction in wound healing," Am. J. Physiol. Cell Physiol., 295:C1215-C1229 (2008).
T.J. et al: "Biological properties of dehydrated human amnion/chorion composite graft: implications for chronic wo und healing". International Wound Journal. (2013); 10(5): 493-500.
Tadmori et al., "Suppression of the allogeneic response by human IL-10: a critical role for suppression of a synergy between IL-2 and TNF-alpha," Cytokine, 6:462-471 (1994).
Taylor et al., "Function of Lymphocytes and Macrophages after Cryopreservation by Procedures for Pancreatic Islets: Potential for Reducing Tissue Immunogenicity," Cryobiology, 25:1-17 (1988).
Taylor, Pamela V; Hancock KW; "Antigenicity of Trophoblast and Possible Antigen-masking Effects during Pregnancy" Immunology, 28, 973-982,(1975).
Thiex et al., "Tissue-specific cytokine release from human extraplacental membranes stimulated by lipopolysaccharide in a two-compartment tissue culture system," Reprod. Biol. Endocrinol., 7:117 (2009).
Thivolet et al., "Long-term survival and immunological tolerance of human epidermal allografts produced in culture," Transplantation, 42:274-280 (1986).
Thomasen, H. et al., Comparison of Cryopreserved and Air-dried Human Amniotic Membrane for Opthalmologic Applications. Graefes Arch Clin Exp Opthalmol. 2009; 24 7(12):1691-700.
Toungouz et al., "Alloactivation induced during mixed-lymphocyte reaction provokes release of tumor necrosis factor alpha and interleukin 6 by macrophages and primes them to lipopolysaccharides," Hum. Immunol., 38:221-225 (1993).
Tredget et al., "Hypertrophic scars, keloids, and contractures. The cellular and molecular basis for therapy," Surg. Clin. North Am., 77:701-730 (1997).
Tredget, E.E., et al., Transforming growth factor-beta in thermally injured patients with hypertrophic scars: effects of interferon alpha-2b. Blast Reconstr Surg, 1998. 102(5): p. 1317-28; discussion 1329-30.
Trengove et al., "Analysis of the acute and chronic wound environments: the role of proteases and their inhibitors," Wound Repair Regen., 7:442-452 (1999).
Tseng et al. "Amniotic Membrane Transplantation With or Without Limbal Allografts for Corneal A Surface Reconstruction in Ratients with Limbal Stern Cell Deficiency" Arch Ophthalmol. (1998); 116(4):431-41.
Ucakhan et al., "Nonpreserved human amniotic membrane transplantation in acute and chronic chemical eye injuries," Cornea, 21 : 169-172 (2002).
Uchide et al. "Possible Role of Proinflammatory and Chemoattractive Cytokines Produced by Human Fetal Membrane Cells in the Pathology of Adverse Pregnancy Outcomes Associated with Influenza Virus Infection." Hindawi Publishing Corporation, Mediators of Inflammation, vol. 2012, pp. 1-32.
Uchino, Y,, et al: "Amniotic membrane immobilized poly(vinyl alcohol) hybrid polymer as an artificial cornea scaffold that supports a stratified and differentiated corneal epithelium". Journal of Biomedical Materials Research. Part B: Applied Biomater. (2007); 81 B(1): 201-206.
Vaalamo et al., "Differential expression of tissue inhibitors of metalloproteinases (TIMP-1, -2, -3, and -4) in normal and aberrant wound healing," Hum. Pathol., 30:795-802 (1999).
Validation of Analytical Procedures: Text and Methodology Q2 (R1) (1994).

(56) References Cited

OTHER PUBLICATIONS

Waddington et al., "Differential roles for small leucine-rich proteoglycans in bone formation," Eur. Gell. Mat., 6:12-21 (2003).

Wang et al., "Interleukin-10 Modulation of Alloreactivity and Graft-Versus-Host Reactions," Transplantation, 74:772-778 (2002).

Wenstrup et al., "Type V Collagen Controls the Initiation of Collagen Fibril Assembly," J. Biol. Chem., 279 (51):53331-53337 (2004).

Wingenfeld et al., "Cryopreservation of Osteochondral Allografts: Dimethyl Sulfoxide Promotes Angiogenesis and Immune Tolerance in Mice," J. Bane Joint Surg. Am., 84-A:1420-1429 (2002).

Written Opinion mailed by the International Searching Authority dated Sep. 29, 2014 for application PCT/US2014/037204, filed on May 7, 2014 (Applicant—Osiris Therapeutics, Inc. // Inventor—Samson, Tom, et al.) (15 pages).

Written Opinion mailed by the International Searching Authority dated Sep. 29, 2014 for application PCT/US2014/037201, filed on May 7, 2014 (Applicant—Osiris Therapeutics, Inc. // Inventor—Samson, Tom, et al.) (15 pages).

Yu et al., "Bone morphogenetic protein 2 stimulates endochondral ossification by regulating periosteal cell fate during bone repair," Bone, 47(1):65-73 (2010).

Zaga et al., "Secretions of Interleukin-1 band Tumor Necrosis Factor a by Whole Fetal Membranes Depend on Initial Interactions of Amnion or Choriodecidua with Lipopolysaccharides or Group B Streptococci," Biol. Reprod., 71:1296-1302 (2004).

Zaga-Clavellina et al., "In vitro secretion profiles of interleukin (IL)-1beta, IL-6, IL-8, IL-10, and TNF alpha after selective infection with *Escherichia coli* in human fetal membranes," Reprod. Biol. Endocrinol., 5:46 (2007).

Zhang X et al: "Mesenchymal progenitor cells derived from chorionic villi of human placenta for cartilage tissue engineering", Biochemical and Biophysical Research Communications, (2006) 340(3):944-952.

\* cited by examiner

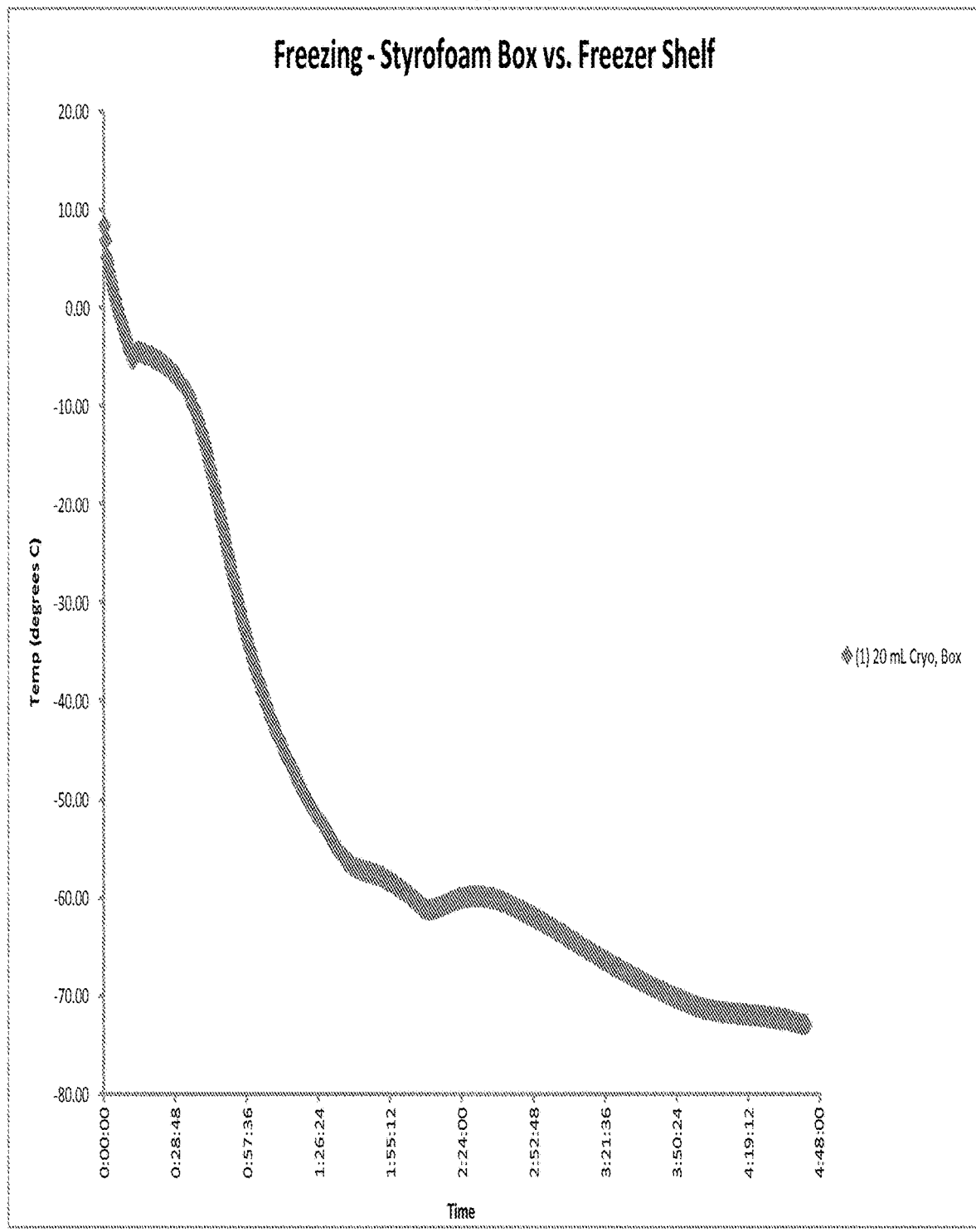

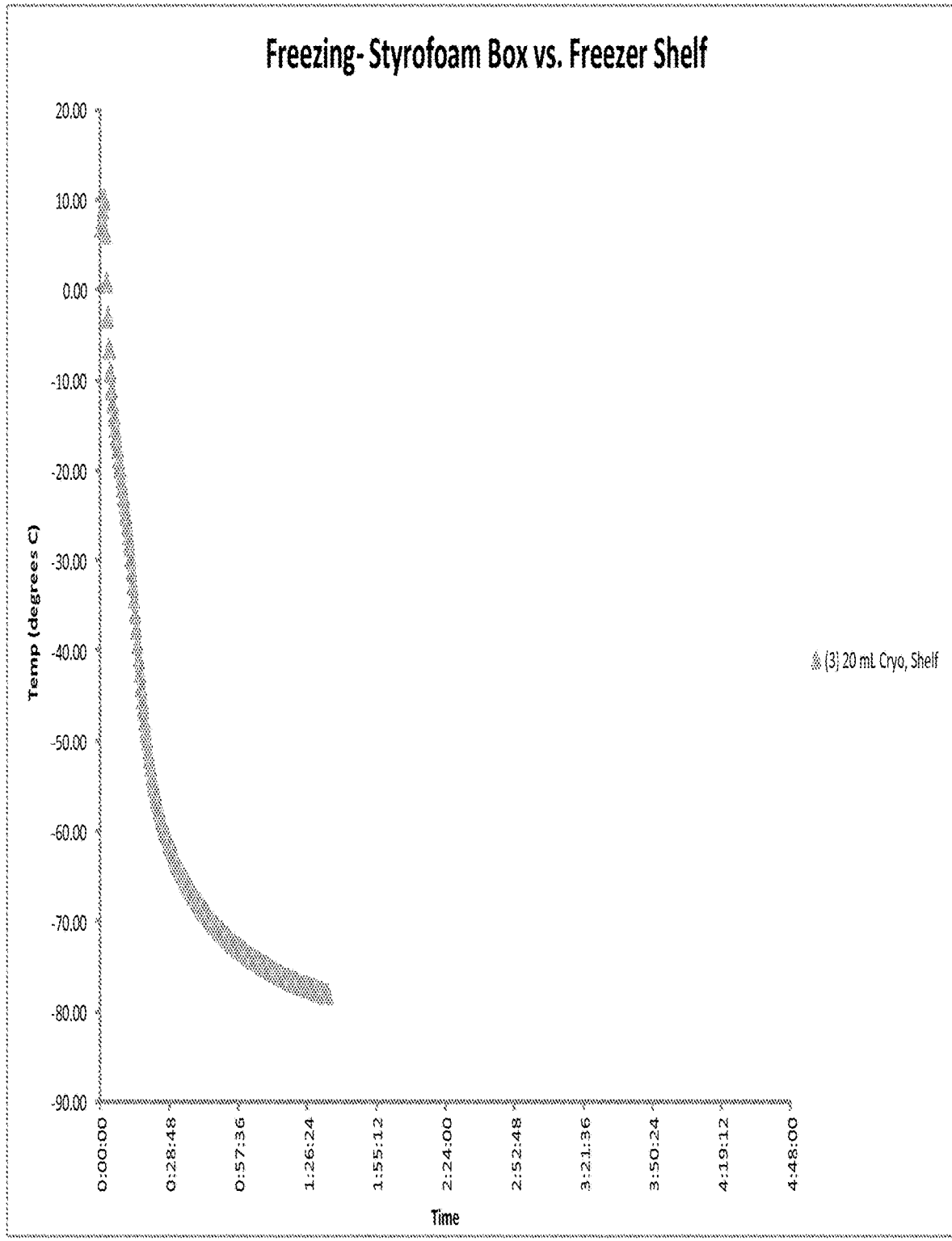

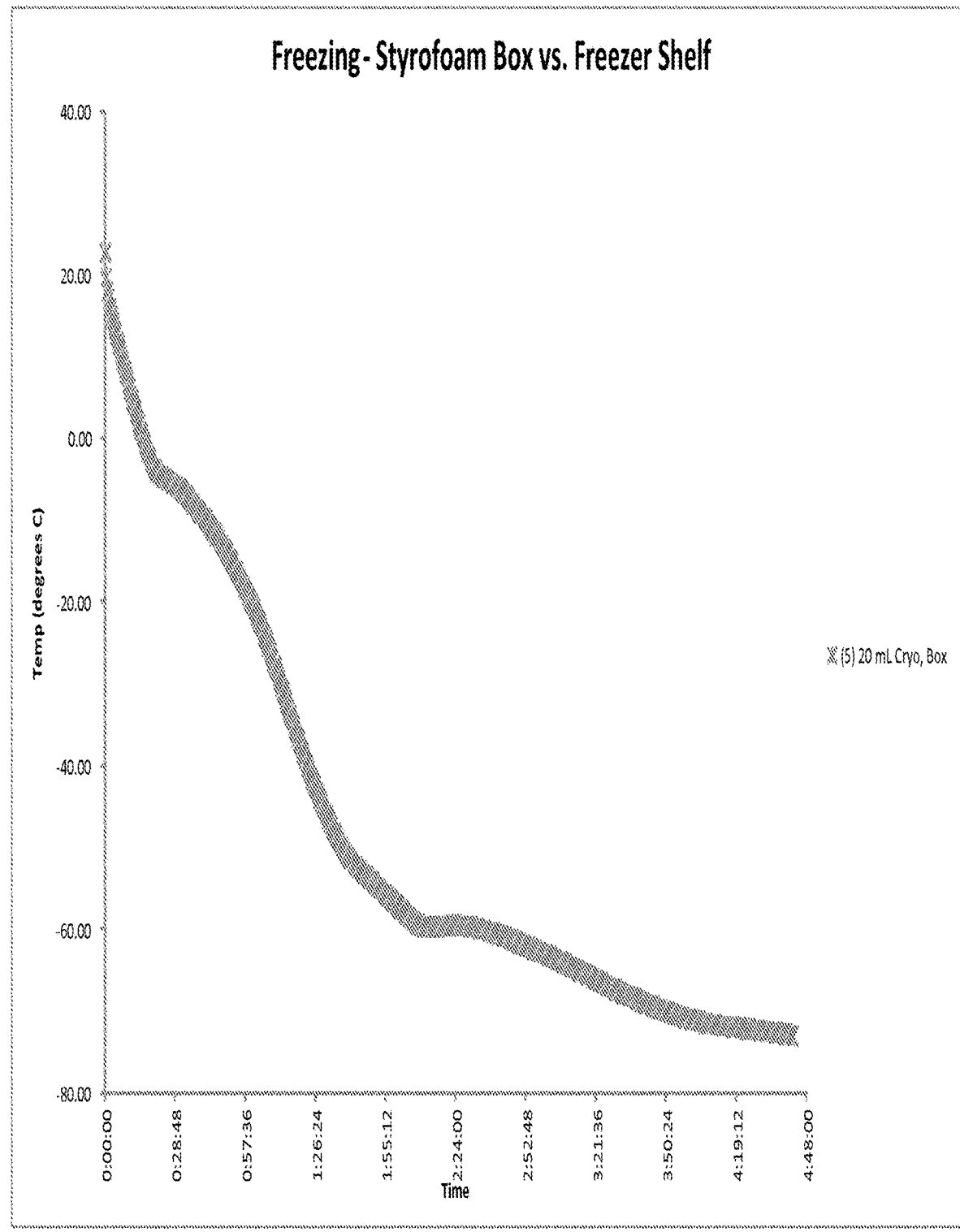

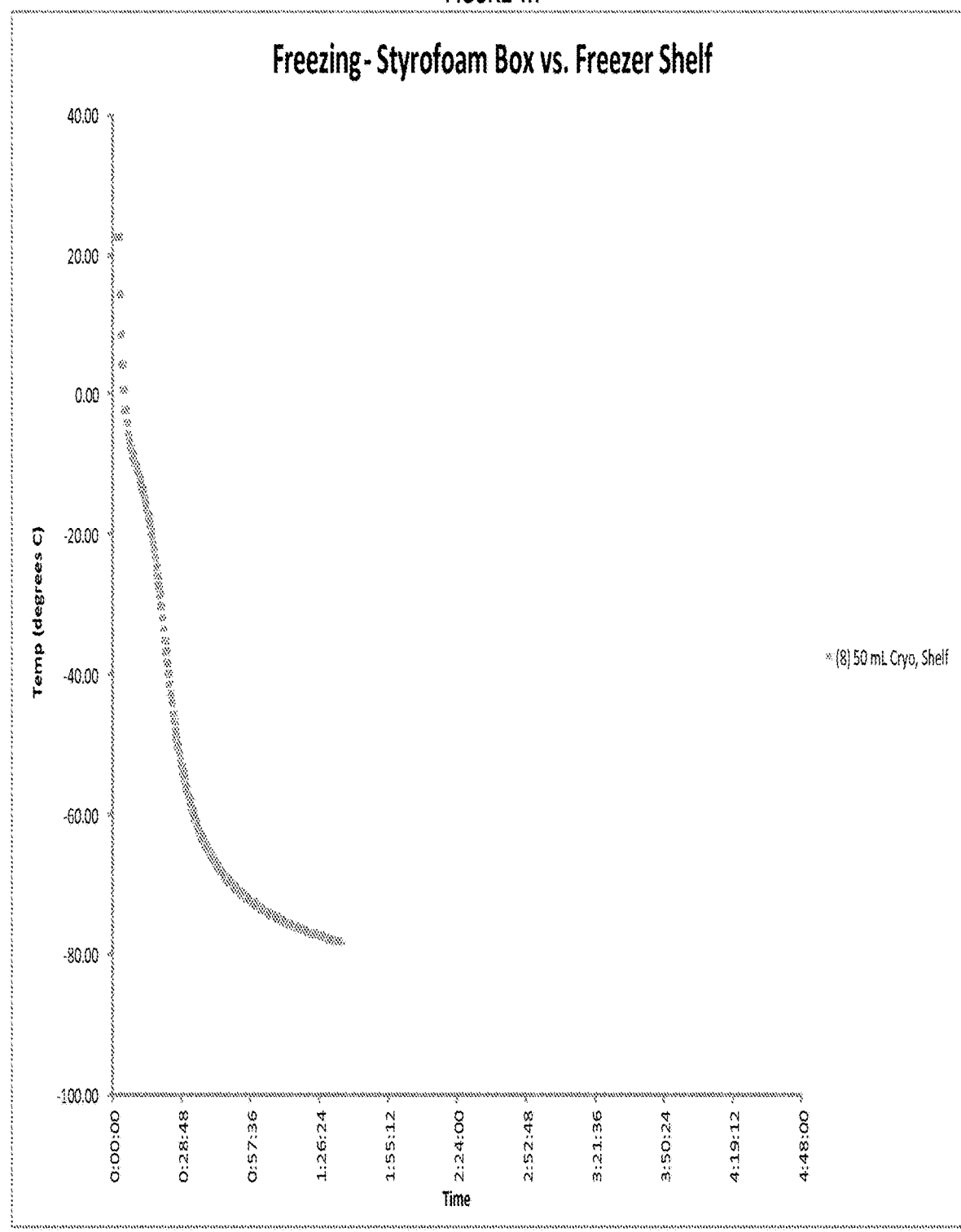

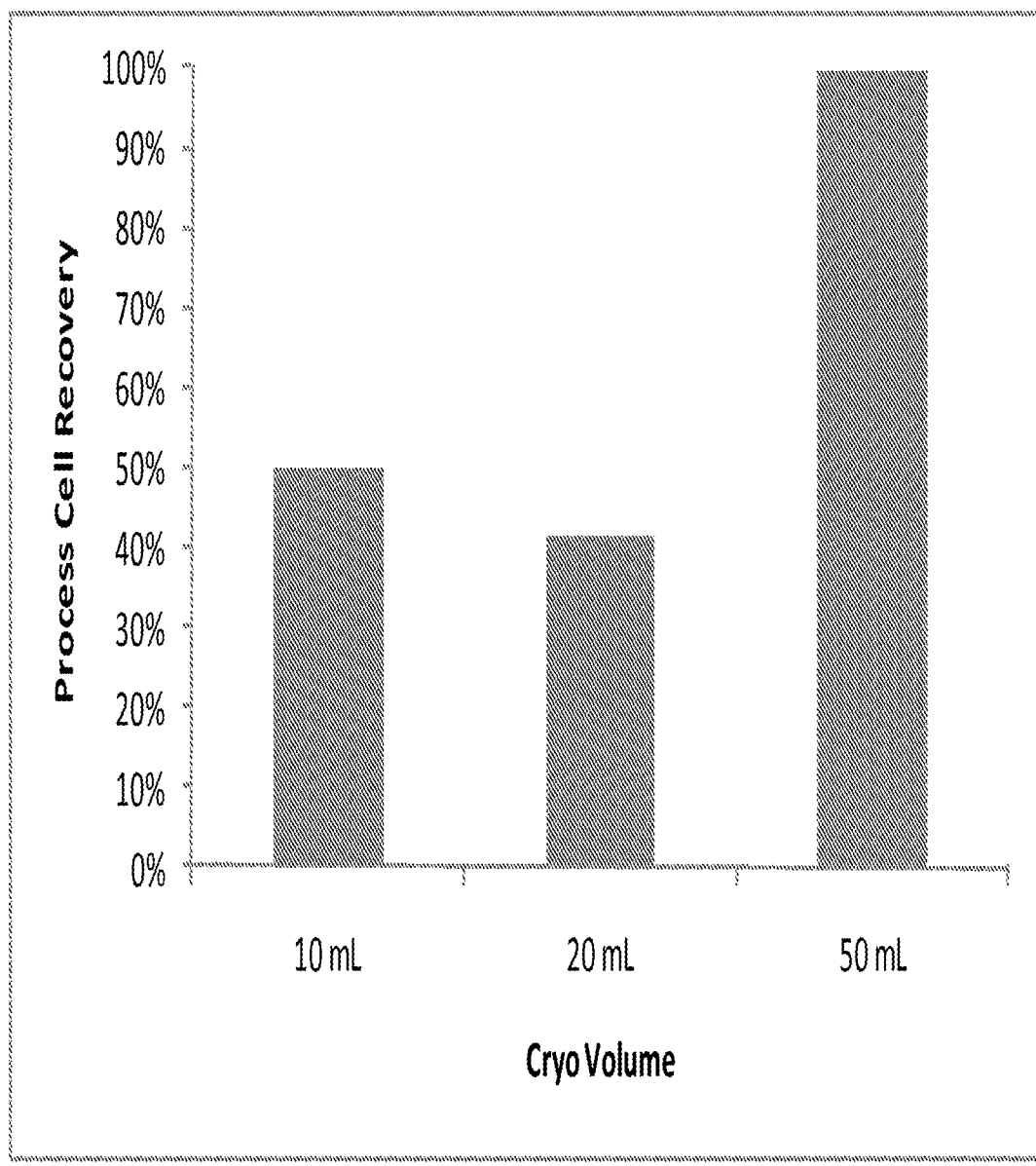

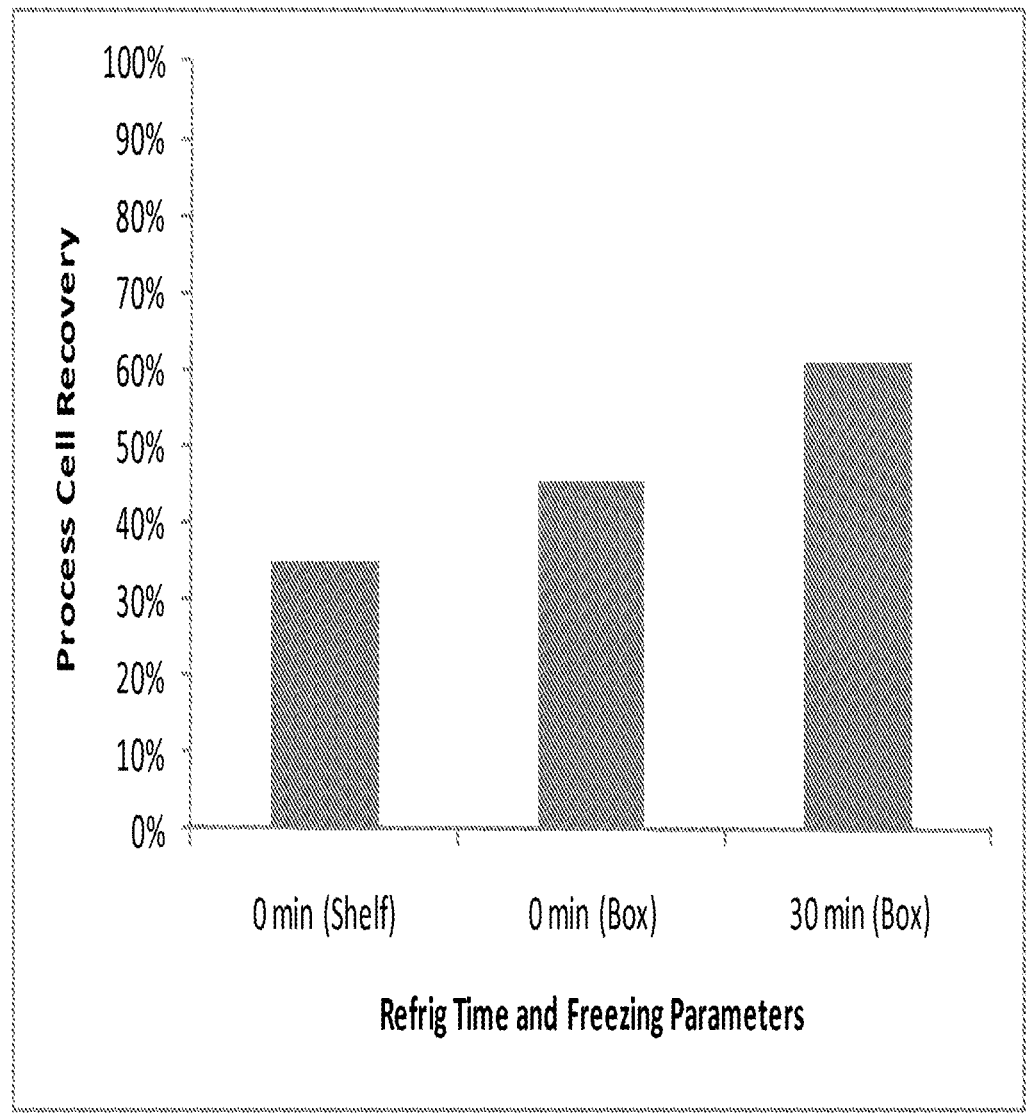

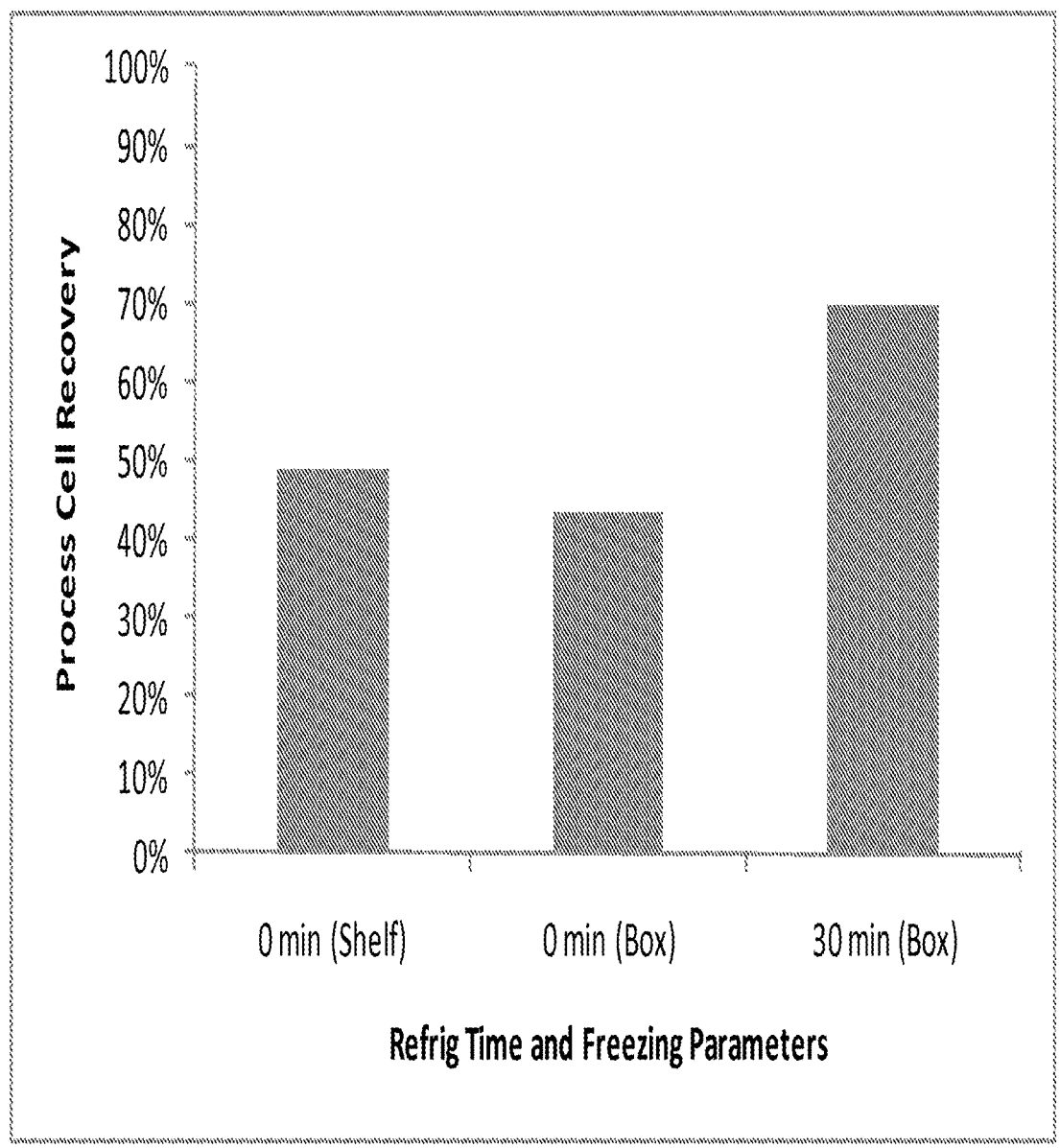

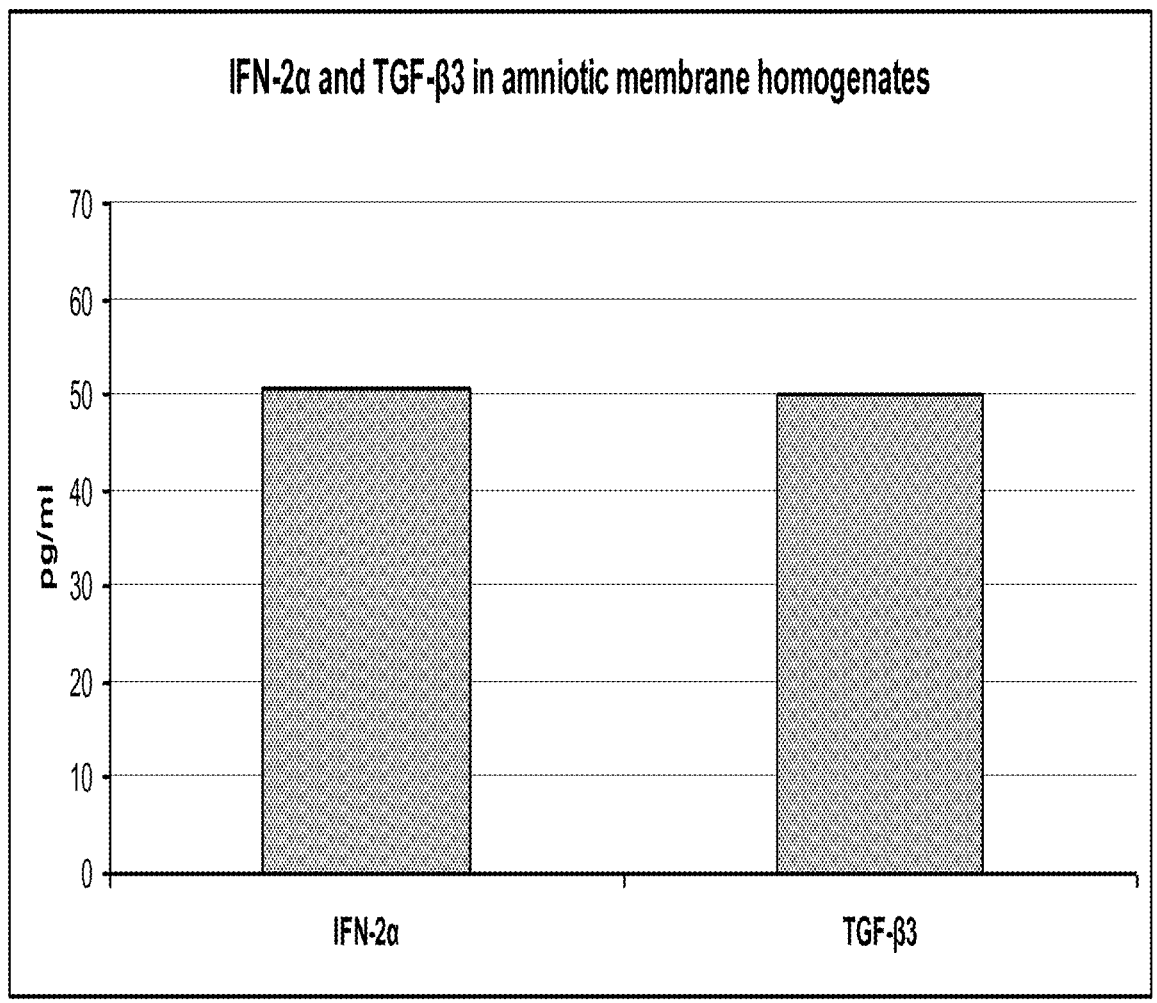

Expression of bone reparative proteins in amniotic membrane homogenates

Expression of IGF-1 in amniotic membrane homogenates though, for example Apligraf is bi-layered using keratinocytes which are obtained from human neonatal foreskin.

METHODS OF MANUFACTURE OF IMMUNOCOMPATIBLE AMNIOTIC MEMBRANE PRODUCTS

RELATED APPLICATIONS

This application is a continuation of U.S. patent application Ser. No. 14/070,035, entitled Methods of Manufacture of Immunocompatible Amniotic Membrane Products, filed on Nov. 1, 2013, which is a continuation of U.S. patent application Ser. No. 13/030,562, entitled Methods of Manufacture of Immunocompatible Amniotic Membrane Products, filed on Feb. 18, 2011, which claims priority to:

U.S. Provisional Application Ser. No. 61/338,464 entitled "Selectively Immunodepleted Chorionic Membranes", filed on Feb. 18, 2010, U.S. Provisional Application Ser. No. 61/338,489 entitled "Selectively Immunodepleted Amniotic Membranes", filed on Feb. 18, 2010, and U.S. Provisional Application Ser. No. 61/369,562 entitled "Therapeutic Products Comprising Vitalized Placental Dispersions filed on Jul. 30, 2010, the contents of which are hereby incorporated by reference in their entireties.

This application is being co-filed on Feb. 18, 2011 with, and incorporates by reference, applications entitled:

"Methods of Manufacture of Immunocompatible Chorionic Membrane Products",

"Immunocompatible Chorionic Membrane Products",

"Immunocompatible Amniotic Membrane Products",

"Therapeutic Products Comprising Vitalized Placental Dispersions", and

"Methods of Manufacture of Therapeutic Products Comprising Vitalized Placental Dispersions"

FIELD OF THE INVENTION

The present technology relates to products to facilitate wound healing such as placenta membrane-derived products and biologic skin. The present technology relates to products to protect injured or damaged tissue, or as a covering to prevent adhesions, to exclude bacteria, to inhibit bacterial activity, or to promote healing or growth of tissue. An example of such a placental membrane is an amniotic membrane. The field also relates to methods of manufacturing and methods of use of such membrane-derived products.

BACKGROUND OF THE INVENTION

Fresh or decellularized placental membranes have been used topically in surgical applications since at least 1910 when Johns Hopkins Hospital reported the use of placental membrane for dermal applications. Subsequently unseparated amnion and chorion were used as skin substitutes to treat burned or ulcerated surfaces. During the 1950's and 60's Troensegaard-Hansen applied boiled amniotic membranes to chronic leg ulcers.

The human amniotic membrane (AM) is the innermost of the fetal membranes deriving from the amniotic sac and constituting the lining of the amniotic cavity. It is approximately 0.02 to 0.5 mm thick. The AM consists of five layers: a thin layer rests on the basement membrane and contacts the amniotic fluid, an underlying layer of connective tissue attaching the basement membrane that consists of three layers: a compact layer, a layer of fibroblast, and a spongy layer. The spongy layer is adjacent to the cellular layer of the chorion. The amnion is essentially devoid of vasculature.

Both fresh and frozen AMs have been used for wound healing therapy. When fresh AM is used, there is increased risk of disease transmission. According to published reports, fresh amniotic tissue exhibits cell viability of 100%, however within 28 days of storage above 0° C. diminished cell viability to 15 to 35%. Freezing over a time of 3 weeks reduced cell viability to 13 to 18%, regardless of the temperature or medium.

Lee and Tseng report the successful cryopreservation of AM in glycerol and Dulbeccos Modified Eagle medium (DMEM) at −80° C., although such cryopreservation dramatically decreases cell viability. The cryopreservation of AM in glycerol and DMEM is recommended by the FDA. According to published reports, glycerol storage of AM resulted in immediate cell death. Glycerol cryopreserved AM (−80° C.) and glycerol-preserved AM (−4° C.) are sufficient to provide a matrix for wound healing, but fail to provide sufficient cell viability to bestow biological effectiveness Gajiwala and Gajiwala report the successful preservation of AM by freeze-drying (lyophilisation) and gamma-irradiation. According to this method, AM is pasteurized at 60° C., treated with 70% ethanol, and freeze-dried to remove most of the remaining moisture. Then the AM is sterilized by exposure of 25 kGy gamma-radiation in a Cobalt 60 Gamma chamber unit or at an ISO-certified radiation plant. The sterilized AM can be stored at room temperature for a short period (up to 6 months).

Gomes reports preservation of AM with lyophilisation followed by sterilization in ethylene oxide.

Rama et al reported the cryopreservation of AM in 10% dimethyl sulfoxide (DMSO) instead of glycerol and achieved a cell viability of about 40%.

Two placental tissue graft products containing living cells, Apligraf and Dermagraft, are currently commercially available. Both Apligraf and Dermagraft comprise ex vivo cultured cells. Neither Apligraf nor Dermagraft comprise stem cells. Furthermore, neither Apligraf nor Dermagraft comprise Insulin-like Growth Factor Binding Protein-1 (IGFBP-1) and adiponectin, which are key factors in the natural wound healing process. In addition, neither Apligraf nor Dermagraft exhibit a protease-to-protease inhibitor ratio favorable for wound healing. As wound healing is a multifactorial biological process, many factors are needed to properly treat a wound; products having non-native cellular populations are less capable of healing wounds relative to a product having an optimal population of cells representing the native array. It would represent an advance in the art to provide a chorion-derived biologic skin substitute comprising a population of cells representing the native array of factors, including, for example, growth factors and cytokines.

Apligraf is a living, bi-layered skin substitute manufactured using neonatal foreskin keratinocytes and fibroblasts with bovine Type I collagen. As used in this application, Apligraf refers to the product available for commercial sale in November 2009.

Dermagraft is cryopreserved human fibroblasts derived from newborn foreskin tissue seeded on extracellular matrix. According to its product literature, Dermagraft requires three washing steps before use which limits the practical implementation of Dermagraft as a wound dressing relative to products that require less than three washing steps. As used in this application, Dermagraft refers to the product available for commercial sale in November 2009.

Engineered wound dressings such as Apligraf and Dermagraft do not provide the best potential for wound healing because they comprise sub-optimal cellular compositions and therefore do not provide proper wound healing. For example, neither Apligraf nor Dermagraft comprises stem cells and, as a result, the ratio between different factors secreted by cells does not enable efficient wound healing. Additionally, some factors that are important for wound healing, including EGF, IGFBP1, and adiponectin, are absent from both Apligraf and Dermagraft. Additionally, some factors, including MMPs and TIMPs, are present in proportions that differ greatly from the proportions found in the natural wound healing process; this difference significantly alters, among other things, upstream inflammatory cytokine pathways which in turn allows for sub-optimal micro-environments at the wound site.

Paquet-Fifield et al. report that mesenchymal stem cells and fibroblasts are important for wound healing (J Clin Invest, 2009, 119: 2795). No product has yet been described that comprise mesenchymal stem cells and fibroblasts.

Both MMPs and TIMPs are among the factors that are important for wound healing. However, expression of these proteins must be highly regulated and coordinated. Excess of MMPs versus TIMPs is a marker of poor chronic wound healing (Liu et al, Diabetes Care, 2009, 32: 117; Mwaura et al, Eur J Vasc Endovasc Surg, 2006, 31: 306; Trengove et al, Wound Rep Reg, 1999, 7: 442; Vaalamo et al, Hum Pathol, 1999, 30: 795).

α2-macroglobulin is known as a plasma protein that inactivates proteinases from all 4 mechanistic classes: serine proteinases, cysteine proteinases, aspartic proteinases, and metalloproteinases (Borth et al., FASEB J, 1992, 6: 3345; Baker et al., J Cell Sci, 2002, 115:3719). Another important function of this protein is to serve as a reservoir for cytokines and growth factors, examples of which include TGF, PDGF, and FGF (Asplin et al, Blood, 2001, 97: 3450; Huang et al, J Biol Chem, 1988; 263: 1535). In chronic wounds like diabetic ulcers or venous ulcers, the presence of high amount of proteases leads to rapid degradation of growth factors and delays in wound healing. Thus, a placental membrane wound dressing comprising α2-macroglobulin would constitute an advance in the art.

An in vitro cell migration assay is important for assessing the wound healing potential of a skin substitute. The process of wound healing is highly complex and involves a series of structured events controlled by growth factors (Goldman, Adv Skin Wound Care, 2004, 1:24). These events include increased vascularization, infiltration by inflammatory immune cells, and increases in cell proliferation. The beginning stages of wound healing revolve around the ability of individual cells to polarize towards the wound and migrate into the wounded area in order to close the wound area and rebuild the surrounding tissue. An assay capable of evaluating the wound healing potential of skin substitutes by examining the correlation between cell migration and wound healing would represent an advance in the art.

SUMMARY OF THE INVENTION

The present invention provides a pharmaceutically acceptable placental product.

A placental product according to the present invention comprises an immunocompatible amniotic membrane in a cryopreservation medium (optionally cryopreserved) and viable native therapeutic cells and native therapeutic factors.

In some embodiments, the amniotic membrane of the placental product is selectively devitalized.

There is now provided a placental product that is selectively depleted of substantially all immunogenic cells.

There is now provided a placental product that does not contain ex vivo cultured cells.

In some embodiments, the placental product further comprises a chorionic membrane that is selectively devitalized.

There is now provided a placental product that comprises at least one of Epidermal Growth Factor, IGFBP1, and Adiponectin.

Optionally, the therapeutic factors include one or more of IGFBP1, adiponectin, α2-macroglobulin, bFGF, and EGF. Optionally, the therapeutic factors include MMP-9 and TIMP1, wherein the ratio of MMP-9:TIMP1 is from about 7 to about 10. Optionally, the therapeutic factors include IGFBP1, adiponectin, α2-macroglobulin, bFGF, EGF, MMP-9, and TIMP1. Optionally, the therapeutic factors include IGFBP1, adiponectin, α2-macroglobulin, bFGF, MMP-9, and TIMP1, wherein the ratio of MMP-9:TIMP1 is from about 7 to about 10 to one. Optionally, the therapeutic factor is present in a substantial amount in comparison to unprocessed human placental membrane. Optionally, each placental product embodiment optionally is devoid of ex-vivo expanded cultured cells.

The present invention also provides a method of manufacturing a placental product comprising: obtaining a placenta, wherein the placenta comprises an amniotic membrane, selectively depleted of immunogenicity, and cryopreserving the placenta, thereby providing a placental product. According to the present invention, the step of selective depletion comprises removing immunogenic cells (e.g. CD14+ macrophages and vascularized tissue-derived cells) and/or immunogenic factors (e.g. TNFα). Optionally, the step of selective depletion comprises removing CD14+ macrophages by refrigerating the placental product for a period of time (e.g. about 30-60 mins.) at a temperature above freezing (e.g. at 2-8° C.), and then freezing, whereby CD14+ macrophages are selectively killed relative to therapeutic cells.

The present invention also provides a method of screening a placental product for therapy comprising assaying the placental product for immunogenicity and/or therapeutic value. Optionally, the step of assaying the placental product for immunogenicity comprises a Mixed Lymphocyte Reaction (MLR) and/or Lipopolysaccharide (LPS)-induced Tumor Necrosis Factor (TNF)-α secretion. Optionally, the step of assaying the placental product for therapeutic value comprises assaying the placental product for cell migration induction.

The present invention also provides a method of treating a subject comprising administering a placental product to the subject. Optionally, the step of administering comprises applying the placental product to a wound, for example, topically applying the placental product to a skin wound. In one embodiment, a placental product is used in a tendon or ligament surgery to promote healing of a tendon or ligament.

The present inventors have identified a need for the development of amniotic membrane products comprising at least one of IGFBP1, and adiponectin, providing superior wound healing properties.

BRIEF DESCRIPTION OF THE DRAWINGS

FIG. 1A-1H depict freezing rates of various freezing methods of the membrane products either in a styrofoam box (1A, 1B, 1E, and 1F) or on a freezer shelf (1C, 1D, 1G, and 1H) under various cryopreservation conditions.

FIG. 3 depicts process cell recovery for chorionic membrane as a function of cryo volume.

FIG. 4 depicts the effects of refrigeration time and freezing parameters on process (cryopreservation) cell recovery for the amniotic membrane.

FIG. 5 depicts the effects of refrigeration time and freezing parameters on process (cryopreservation) cell recovery for the chorionic membrane.

FIG. 14 depicts expression of IFN-2α and TGF-β3 in amniotic membrane homogenates.

DETAILED DESCRIPTION OF THE INVENTION

Figure 1B:
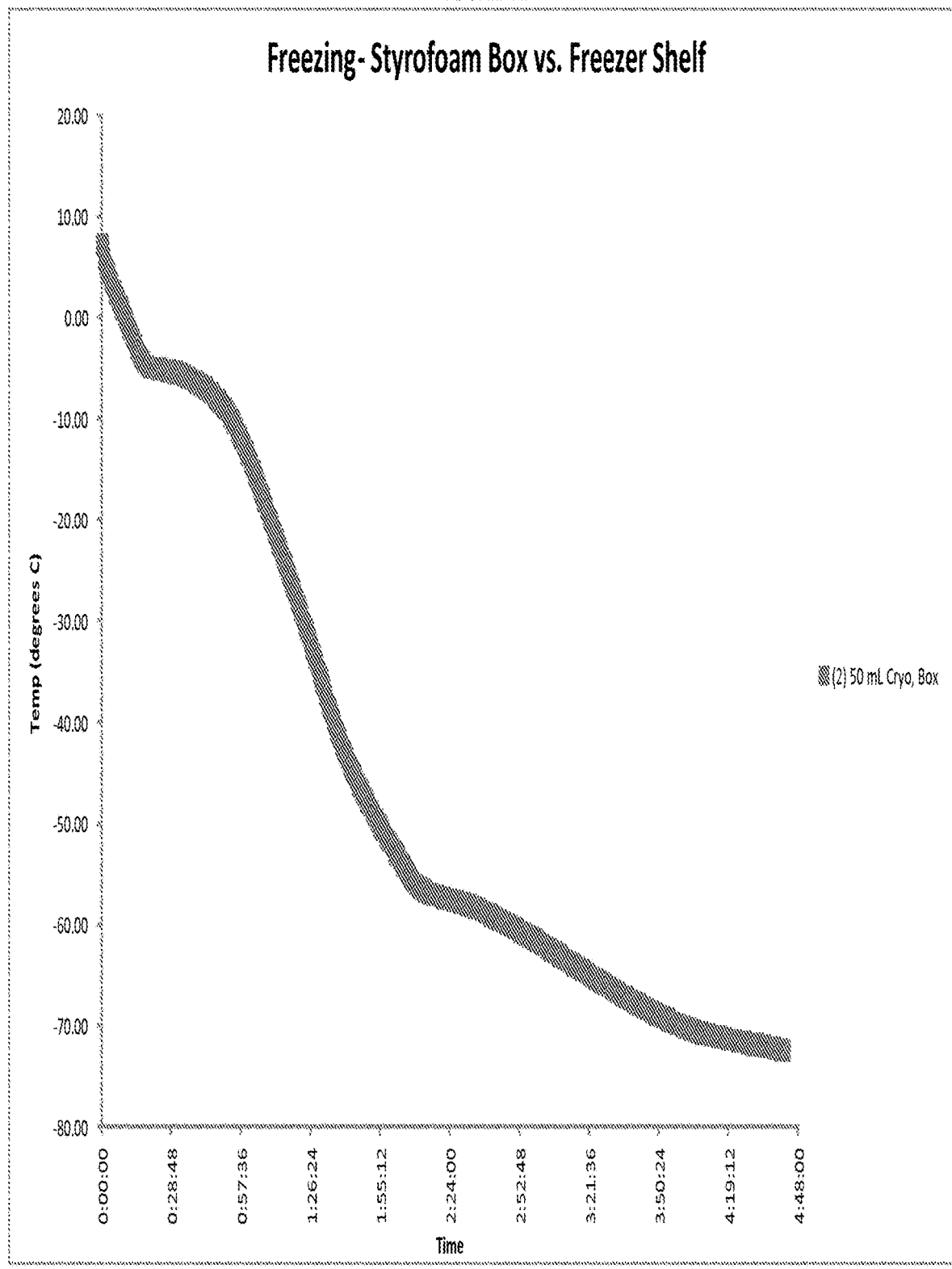
Figure 1D:
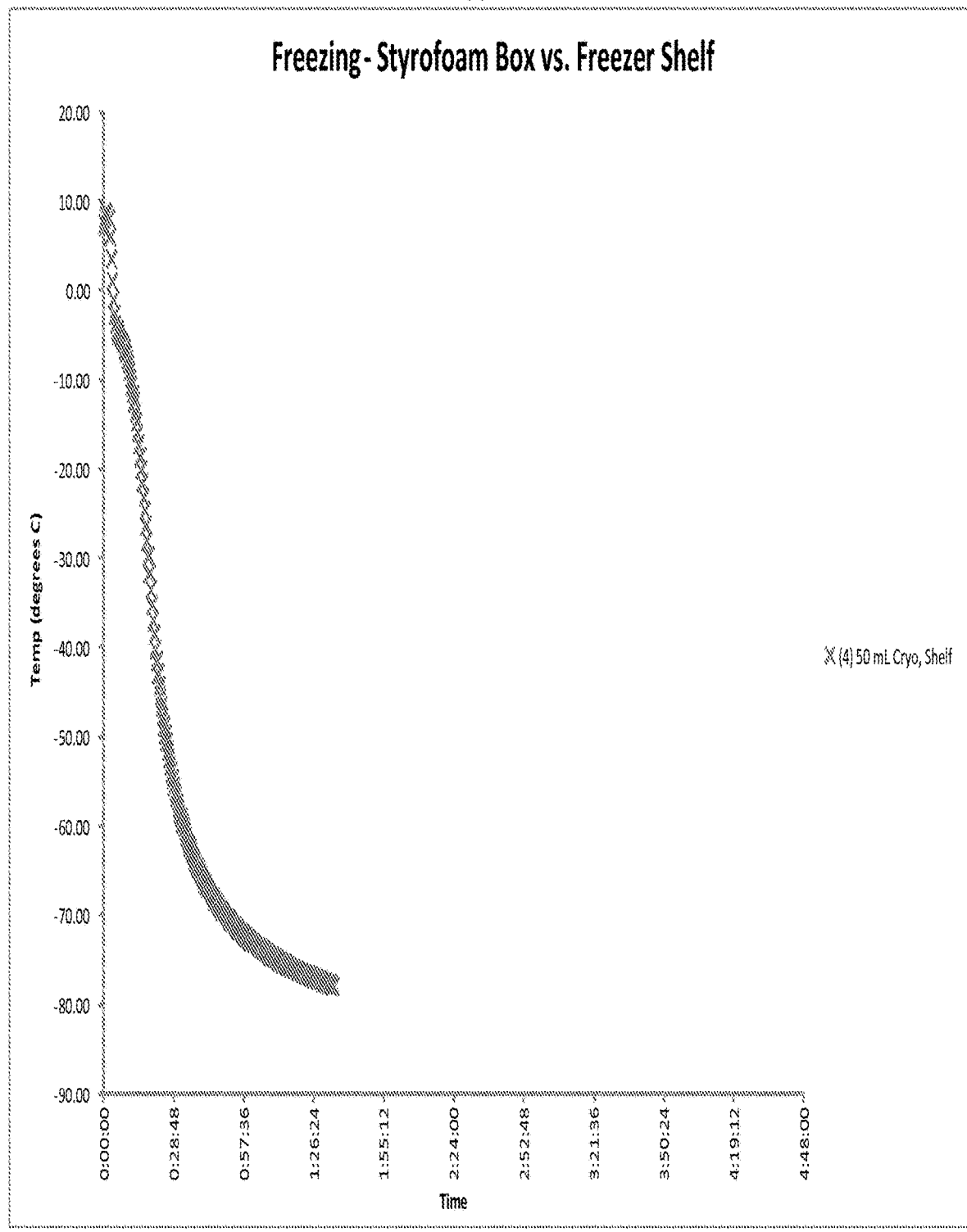
Figure 1F:
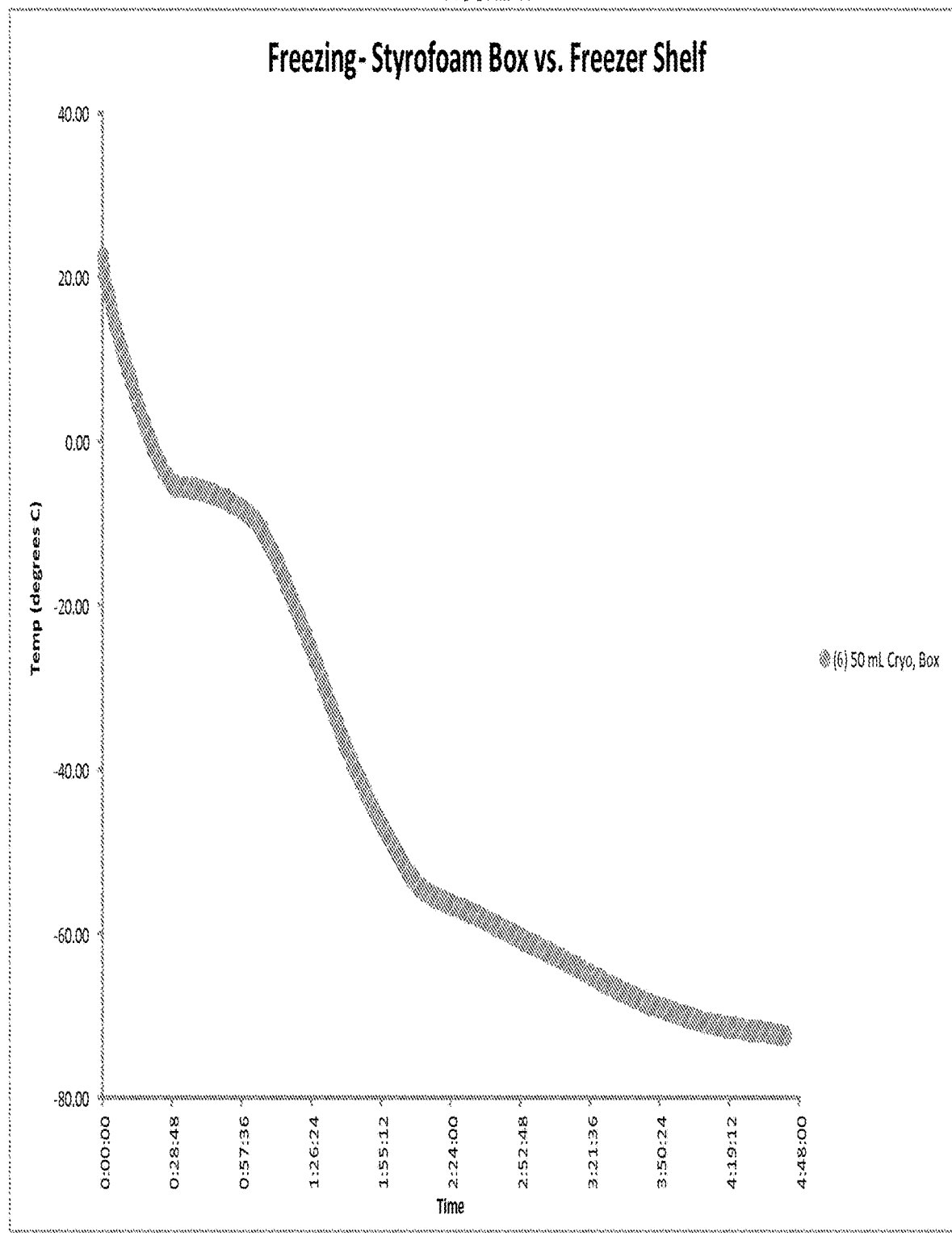
Figure 1G:
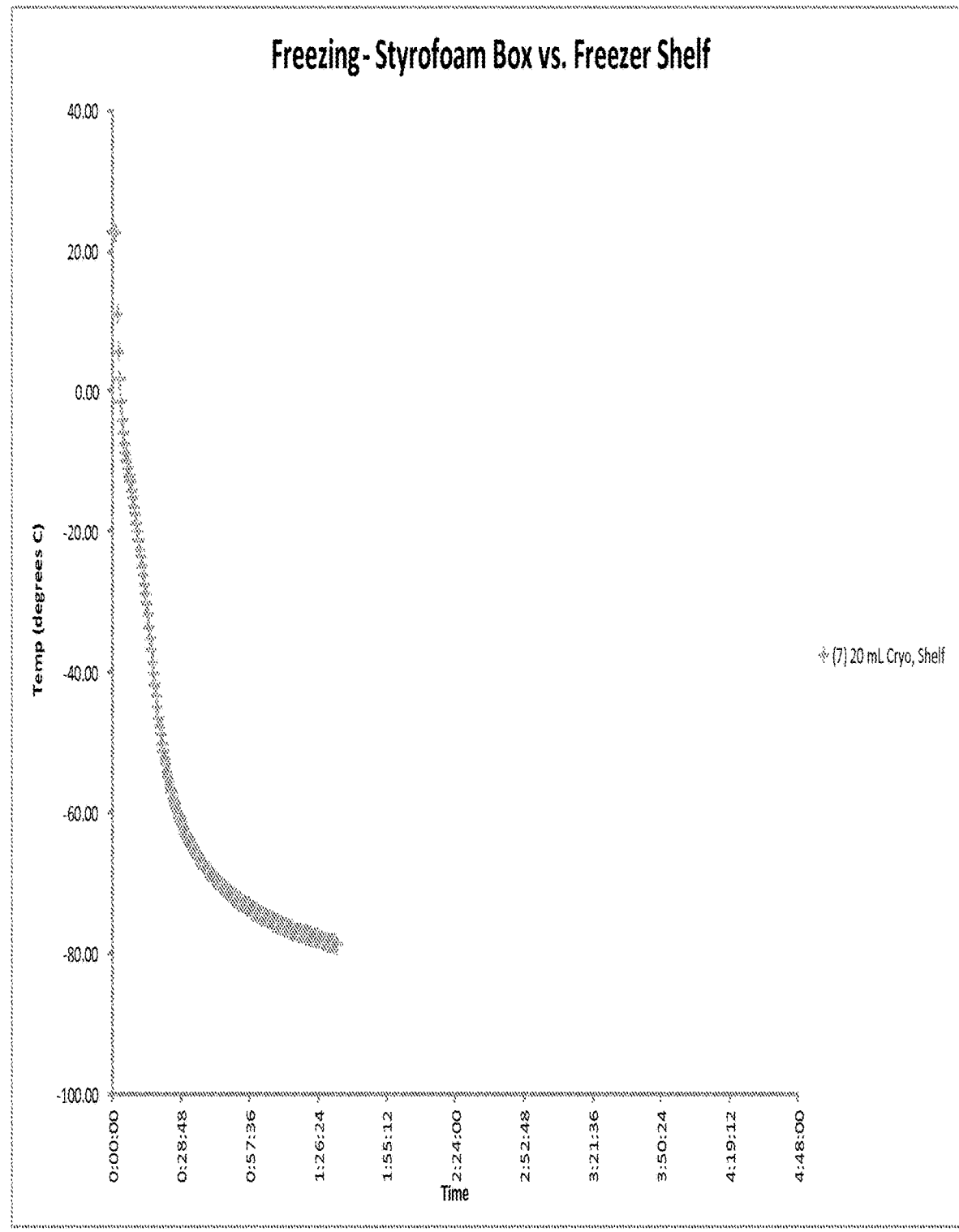

As used herein, the following definitions apply:

"Examplary" (or "e.g." or "by example") means a non-limiting example.

"hCMSCs: means human chorionic membrane stromal cells. hCMSCs are generally positive for CD73?, CD70, CD90, CD105, and CD166; negative for CD45 and CD34. hCMSCs differentiate to mesodermal lineages (osteogenic, chondrogenic, and adipogenic).

"Selective depletion of immunogenicity" or "selective depletion of immunogenic cells or factors" or "selective depletion" means a placental product that retains live therapeutic cells and/or retains therapeutic efficacy for the treatment of tissue injury yet is free, substantially free, or depleted of at least one of immune cell type (e.g. CD14+ macrophages, trophoblasts, and/or vascular-tissue derived cells) and/or immunogenic factor that are otherwise present in a native placenta or amniotic membrane.

"MSC" means mesenchymal stem cells and include fetal, neonatal, adult, or post-natal. "MSCs" include amniotic MSCs (AMSCs). MSCs generally express one or more of CD73, CD90, CD105, and CD166.

"Native cells" means cells that are native, resident, or endogenous to the placental membrane, i.e. cells that are not exogenously added to the placental membrane.

"Native factors" means placental membrane factors that are native, resident, or endogenous to the placental membrane, i.e. factors that are not exogenously added to the placental membrane.

"Placental products" means the instant placental products disclosed and claimed herein.

"Substantial amount" of an element of the present invention, e.g. native factors, native cells, therapeutic factors, or selective depletion, means a value at least about 10% or more in comparison to an unprocessed, not cryopreserved, fresh membrane sample. A substantial amount can optionally be at least about 50%.

"Therapeutic cells" or "beneficial cells" means stromal cells, MSCs, fibroblasts, and/or epithelial cells.

"Therapeutic factors" means placenta- or amniotic membrane-derived factors that promote wound healing. Examples include IGFBP1, adiponectin, α2-macroglobulin, and/or bFGF. Other examples include MMP-9 and TIMP1.

"Stromal cells" refers to a mixed population of cells present (optionally in native proportions) composed of neonatal mesenchymal stem cells and neonatal fibroblasts. Both neonatal mesenchymal stem cells and neonatal fibroblasts are immunoprivileged; neither express surface proteins present on immunogenic cell types.

In some embodiments, the present technology discloses placental products for clinical use, including use in wound healing such as diabetic foot ulcers, venous leg ulcers, and burns. The manufacturing process optionally eliminates essentially all potentially immunogenic cells from the placental membrane while preserving of specific cells that play an important role in wound healing.

In some embodiments, the present technology discloses a placental product that is selectively devitalized. There is now provided a placental product that is selectively depleted of substantially all immunogenic cells. There is now provided a placental product that does not contain ex vivo cultured cells. There is now provided a placental product that comprises at least one of IGFBP1, and adiponectin. There is now provided a placental product that comprises Epidermal Growth Factor, IGFBP1. There is now provided a placental product that comprises adiponectin.

In some embodiments, the present technology discloses a method of cyropreserving a placental product that preserves the viability of specific beneficial cells that are the primary source of factors for the promotion of healing to the wound healing process while selectively depleting immunogenic cells (e.g. killing or rendering non-immunogenic).

In some embodiments, the present technology discloses a bioassay to test immunogenicity of manufactured placental products.

In some embodiments, the present technology discloses a placental product exhibiting a therapeutic ratio of MMP to TIMP comparable to that exhibited in vivo. The present inventors have identified a need for the development of placental products exhibiting a ratio of MMP-9 and TIMP1 of about 7-10 to one.

In some embodiments, the present technology discloses a placental product that comprises α2-macroglobulin.

There is now provided a placental product that inactivates substantially all serine proteinases, cysteine proteinases, aspartic proteinases, and metalloproteinases present in the amniotic membrane. There is now provided a placental product that inactivates substantially all serine proteinases present in the amniotic membrane. There is now provided a placental product that inactivates substantially all cysteine proteinases present in the amniotic membrane. There is now provided a placental product that inactivates substantially all aspartic proteinases present in the amniotic membrane. There is now provided a placental product that inactivates substantially all metalloproteinases present in the amniotic membrane.

In some embodiments, the present technology discloses a placental product that comprises bFGF.

In some embodiments, the present technology discloses a placental product exhibiting a protease-to-protease inhibitor ratio favorable for wound healing.

In some embodiments, the present technology discloses a cell migration assay capable of evaluating the wound-healing potential of a placental product.

IGFBP1 and adiponectin are among the factors that are important for wound healing. Evaluation of proteins derived from placental products prepared according to the presently disclosed technology reveal that EGF is one of the major factors secreted in higher quantities by these tissues. Additionally, the importance of EGF for wound healing together with high levels of EGF detected in the presently disclosed amniotic membranes support selection of EGF as a potency marker for evaluation of membrane products manufactured for clinical use pursuant to the present disclosure.

The present technology discloses a cryopreservation procedure for a placental product that selectively depletes immunogenic cells and preserves the viability of other beneficial cells (including at least one or 2 or all of mesenchymal stem cells, epithelial cells and fibroblasts. In some embodiments, the beneficial cells are the primary source of factors for the promotion of healing.

Placental products, their usefulness, and their immunocompatability are surprisingly enhanced by depletion of maternal trophoblast and selective elimination of CD14+ fetal macrophages. Immunocompatability can be demonstrated by any means commonly known by the skilled artisan, such demonstration can be performed by the mixed Lymphocyte Reaction (MLR) and by lipopolysaccharide (LPS)-induced Tumor Necrosis Factor (TNF)-α secretion.

The instant placental products contain bFGF optionally at a substantial concentration.

The instant placental products optionally secrete factors that stimulate cell migration and/or wound healing. The presence of such factors can be demonstrated by any commonly recognized method, For example, commercially available wound healing assays exist (Cell Biolabs) and cell migration can be assessed by cell line HMVEC (Lonza Inc.). In one embodiment, conditioned medium from the present placental products enhance cell migration.

The placental products disclosed herein are useful in treating a number of wounds including: tendon repair, cartilage repair (e.g. femoral condyle, tibial plateau), ACL replacement at the tunnel/bone interface, dental tissue augmentation, fistulas (e.g. Crohn's disease, G-tube, tracheoesophogeal), missing tissue at adhesion barriers (e.g. nasal septum repair, vaginal wall repair, abdominal wall repair, tumor resection), dermal wounds (e.g. partial thickness burns, toxic epidermal necrolysis, epidermolysis bullosa, pyoderma gangrenosum, ulcers e.g. diabetic ulcers (e.g. foot), venous leg ulcers), surgical wounds, hernia repair, tendon repair, bladder repair, periosteum replacement, keloids, organ lacerations, epithelial defects, and repair or replacement of a tympanic membrane.

The placental products disclosed herein exhibit one or more of the following properties beneficial to the wound healing process:

a. an epithelial cell layer, wherein the approximate number of cells per cm2 of the amniotic membrane is about 10,000 to about 360,000 or about 40,000 to about 90,000.
b. a thick basement membrane (comprising one or more of Collagen Type I, III, IV, laminin, and fibronectin),
c. a stromal cell layer;
d. an amniotic membrane with a thickness of about 20 to about 50 μm,
e. high thrombin activity,
f. low immunogenicity,
g. cryopreserved/cryopreserveable,
h. amniotic MSC,
i. analgesic effect
j. reduces scarring,
k. anti-inflammatory proteins such as IL-1a and IL-10,
l. anti-inflammatory suppression of lymphocyte reactivity in vitro, for example by inhibition of CD8+ and CD4+ proliferation or increased CD4+ Treg cells,
m. antibacterial proteins such as defensins and allantoin (bacteriolytic proteins),
n. angiogenic and mitogenic factors that promote re-epithelialization such as EGF, HGF, and VEGF,
o. cells that are positive for CD70, CD90, CD105, and CD166 and negative for CD45 and CD34,
p. cells that express HLA-G,
q. cells that express a placenta specific MHC-1 antigen important to immune tolerance that inhibits both NK cytolysis and T-cell-mediated cytolysis and activation of immune cells (e.g. interferon-γ secretion),
r. cells that express IDO and FAS ligand, which likely contribute to immune tolerance,
s. cells with a capacity to differentiate into 1-Human Amniotic Epithelial Cells (hAECs)
t. cells with a capacity to differentiate to neural, hepatocyte, and pancreatic cells,
u. Human Amniotic Membrane Stromal Cells (hAMSCs) differentiate to mesodermal lineages (osteogenic, chondrogenic, and adipogenic) and to all three germ layers-ectoderm (neural), mesoderm (skeletal muscle, cardiomyocytic, and endothelial), and ectoderm (pancreatic),
v. Cells that expression CD49d by hAMSCs distinguishes hAMSCs from hAECs,
w. hAMSCs that positive for the embryonic cytoplasmic marker Oct-4 that plays a role in maintaining pluripotency and self renewal,
x. hAECs that are positive for SSEA-3, SSEA-4, TRA-1-60, TRA-1-81, and negative for SSEA-4 and non-tumorogenic.

The present inventors have now identified a need for the development of placental products that do not contain ex vivo cultured cells.

The present inventors have now identified a need for the development of placental products comprising IGFBP1.

The present inventors have now identified a need for the development of placental products comprising adiponectin.

The present inventors have now identified a need for the development of placental products exhibiting a protease-to-protease inhibitor ratio favorable for wound healing.

The present inventors have now identified a need for the development of a method of cyropreserving placental products that preserves the viability of specific cells that are other beneficial cells that are the primary source of factors for the promotion of healing to the wound healing process while selectively depleting immunogenic cells from chorionic membranes.

The present inventors have now identified a need for the development of a bioassay to test immunogenicity of manufactured placental products.

The present inventors have now identified a need for the development of placental products exhibiting a ratio of MMP toTIMP comparable to that exhibited in vivo. The present inventors have now identified a need for the development of placental products exhibiting a ratio of MMP-9 and TIMP1 of about 7-10 to one.

The present inventors have now identified a need for the development of placental products that comprise α2-macroglobulin.

The present inventors have now identified a need for the development of placental products that inactivate serine proteinases, cysteine proteinases, aspartic proteinases, and metalloproteinases. The present inventors have now identified a need for the development of placental products that inactivate serine proteinases. The present inventors have now identified a need for the development of placental products that inactivate cysteine proteinases. The present inventors have now identified a need for the development of placental products that inactivate aspartic proteinases. The present inventors have now identified a need for the development of placental products that inactivate metalloproteinases.

The present inventors have now identified a need for the development of placental products that comprise bFGF.

The present inventors have now identified a need for the development of a cell migration assay to evaluate the potential of placental membrane products.

The present inventors have now identified a need for the development of a placental product for wound healing that comprises mesenchymal stem cells, epithelial cells and fibroblasts.

Placental Product

Overview

One embodiment of the present invention provides a placental product comprising a cryopreservation medium and an amniotic membrane, wherein the amniotic membrane comprises viable native therapeutic cells and native therapeutic factors, and wherein the cryopreservation medium comprises a cryopreserving amount of a cryopreservative. According to this embodiment, the amniotic membrane is substantially free of at least one at least one or both of the following immunogenic cell types: CD14+ macrophages and vascularized tissue-derived cells.

In one embodiment, the amniotic membrane comprises one or more layers which exhibit the architecture of the native amniotic membrane (e.g. has not been homogenized or treated with collagenase).

In one embodiment, the placental product is suitable for dermal application to a wound.

With the teachings provided herein, the skilled artisan can now produce the present placental products. The present disclosure provides methods of manufacture that produce the technical features of the present placental products. Accordingly, in one embodiment, the placental product is manufactured by steps taught herein. The present placental products are not limited to products manufactured by the methods taught here. For example, products of the present invention could be produced through methods that rely on screening steps; e.g. steps to screen for preparations with the described technical features and superior properties.

The present placental product comprises one or more of the following technical features:

a. the viable therapeutic native cells are capable of differentiating into cells of more than one lineage (e.g. osteogenic, adipogenic and/or chonodrogenic lineages),
b. the native therapeutic factors include IGFBP1,
c. the native therapeutic factors include adiponectin,
d. the native therapeutic factors include α2-macroglobulin,
e. the native therapeutic factors include bFGF,
f. the native therapeutic factors include EGF,
g. the native therapeutic factors include MMP-9 and TIMP1,
h. the native therapeutic factors include MMP-9 and TIMP1 in a ratio of about 7 to about 10,
i. the placental product does not comprise ex-vivo cultured cells,
j. the cryopreservative medium is present in an amount of greater than about 20 ml or greater than about 50 ml,
k. the cryopreservative comprises DMSO,
l. cryopreservative comprises DMSO in a majority amount,
m. the cryopreservation medium further comprises albumin, optionally wherein the albumin is HSA,
n. the cryopreservative comprises DMSO and albumin (e.g. HSA),
o. comprises about 5,000 to about 240,000 cells/cm$^2$ or about 20,000 to about 60,000,
p. the amniotic membrane comprises at least: about 2,000, or about 2,400, or about 4,000' or about 6,000, or about 8,000, or about 10,000, or about 10,585, or about 15,000 stromal cells per unit cm$^2$ of the amniotic membrane,
q. the amniotic membrane comprises about 2,000 to about 15,000 of stromal cells per cm$^2$ of the amniotic membrane,
r. comprises stromal cells wherein at least: about 40%, or about 50%, or about 60%, or about 70%, or about 74.3%, or about 83.4 or about 90%, or about 92.5% of the stromal cells are viable after a freeze-thaw cycle,
s. comprises stromal cells wherein about 40% to about 92.5% of the stromal cells are viable after a freeze-thaw cycle,
t. the amniotic membrane has a thickness of about 20 μm to about 50 μm,
u. secretes less than about any of: 420 pg/mL, 350 pg/mL, or 280 pg/mL TNF-α into a tissue culture medium upon placing a 2 cm×2 cm piece of the tissue product in a tissue culture medium and exposing the tissue product to a bacterial lipopolysaccharide for about 20 to about 24 hours,
v. cryopreservation and thawing, secretes less than about any of: 420 pg/mL, 350 pg/mL, or 280 pg/mL TNF-α into a tissue culture medium upon placing a 2 cm×2 cm piece of the tissue product in a tissue culture medium and exposing the tissue product to a bacterial lipopolysaccharide for about 20 to about 24 hours,
w. after refrigeration, cryopreservation and thawing, secretes less than about any of: 420 pg/mL, 350 pg/mL, or 280 pg/mL TNF-α into a tissue culture medium upon placing a 2 cm×2 cm piece of the tissue product in a tissue culture medium and exposing the tissue product to a bacterial lipopolysaccharide for about 20 to about 24 hours, x. further comprises an chorionic membrane, amniotic membrane comprises a layer of amniotic epithelial cells,

Y.

z. further comprises an chorionic membrane, wherein the amniotic membrane and the chorionic membrane are associated to one another in the native configuration, aa. further comprises an chorionic membrane, wherein the amniotic membrane and the chorionic membrane are not attached to one another in the native configuration, bb. further comprises a chorionic membrane wherein the chorionic membrane comprises about 2 to about 4 times more stromal cells relative to the amniotic membrane, cc. does not comprise a chorionic membrane;

dd. comprises chorionic membrane, wherein the chorionic membrane comprises about 2 to about 4 times more stromal cells relative to the amniotic membrane, and ee. is suitable for dermal application to a wound;

Cells

According to the present invention, a placental product comprises native therapeutic cells of the amniotic membrane. The cells comprise one or more of stromal cells, MSCs, fibroblasts, and epithelial cells.

In one embodiment, the native therapeutic cells comprise viable stromal cells.

In one embodiment, the native therapeutic cells comprise viable MSCs.

In one embodiment, the native therapeutic cells comprise viable fibroblasts.

In one embodiment, the native therapeutic cells comprise viable epithelial cells.

In one embodiment, the native therapeutic cells comprise viable MSCs and viable fibroblasts.

In one embodiment, the native therapeutic cells comprise viable MSCs, viable fibroblasts, and viable epithelial cells.

In one embodiment, the native therapeutic cells comprise viable stromal cells and viable epithelial cells.

In one embodiment, the therapeutic native cells are viable cells capable of differentiating into cells of more than one lineage (e.g. osteogenic, adipogenic and/or chonodrogenic lineages).

In one embodiment, the placental product comprises about 10,000 to about 360,000 or about 40,000 to about 90,000 cells per $cm^2$.

In one embodiment, the placental product comprises at least: about 2,000, or about 2,400, or about 4,000, or about 6,000, or about 8,000, or about 10,000, or about 10,585, or about 15,000 stromal cells per unit $cm^2$ of the placental product.

In one embodiment, the placental product comprises about 2,000 to about 15,000 of stromal cells per $cm^2$ of the placental product.

In one embodiment, the placental product comprises stromal cells wherein at least: about 40%, or about 50%, or about 60%, or about 70%, or about 74.3%, or about 83.4 or about 90%, or about 92.5% of the stromal cells are viable after a freeze-thaw cycle.

In one embodiment, the placental product comprises stromal cells wherein about 40% to about 92.5% of the stromal cells are viable after a freeze-thaw cycle.

In one embodiment, the placental product comprises less than about 1% of CD14+ macrophages per total cells.

In one embodiment, the amniotic membrane of the placental product comprises about 2 to about 4 times less stromal cells relative to a chorionic membrane of the same area derived from the same placenta.

In one embodiment, the placental product further comprises membrane chorionic membrane containing about 2 to about 4 times more stromal cells relative to the amniotic membrane.

In one embodiment, the amniotic membrane of the placental product comprises MSCs in an amount of: at least about 1%, at least about 2%, at least about 3%, at least about 4%, at least about 5%, about 1% to about 10%, or about 3% to about 10%, relative to the total number of cells in the amniotic membrane of the placental product. Optionally, at least: about 40%, about 50%, about 60%, or about 70% of the MSCs are viable after a freeze-thaw cycle.

In one embodiment, the amniotic membrane of the placental product comprises fibroblasts in an amount of: about 1%, about 20%, about 5% to about 15%, at least about 1%, at least about 2%, at least about 3%, or at least about 4 relative to the total number of cells in the amniotic membrane of the placental product. Optionally, at least: about 40%, about 50%, about 60%, or about 70% of the fibroblasts are viable after a freeze-thaw cycle.

In one embodiment, the amniotic membrane of the placental product comprises stromal cells in an amount of: about 5% to about 40%, about 5% to about 30%, about 10% to about 30%, about 15% to about 25%, at least about 5%, at least about 10%, or at least about 15%, relative to the total number of cells in the amniotic membrane of the placental product. Optionally, at least: about 40%, about 50%, about 60%, or about 70% of the stromal cells are viable after a freeze-thaw cycle.

In one embodiment, the amniotic membrane of the placental product comprises epithelial cells in an amount of: about 60% to about 90%, about 70% to about 90%, about 40% to about 90%, about 50% to about 90%, at least about 40%, at least about 50%, least about 60%, or at least about 70%, relative to the total number of cells in the amniotic membrane of the placental product. Optionally, at least: about 40%, about 50%, about 60%, or about 70% of the epithelial cells are viable after a freeze-thaw cycle.

In one embodiment, the amniotic membrane of the placental product comprises MSCs and functional macrophages in a ratio of greater than about any of: 5:1, 7:1, or 10:1.

In one embodiment, the amniotic membrane of the placental product comprises fibroblasts and functional macrophages in a ratio of greater than about any of: 10:1, 15:1, 20:1, or 25:1.

In one embodiment, the amniotic membrane of the placental product comprises fibroblasts and MSCs in a ratio of: about 4:1 to about 1:1 or about 3:1 to about 3:2, or about 2:1.

In one embodiment, the amniotic membrane of the placental product comprises MSCs in an amount of: at least about 1,000 cells/$cm^2$, at least about 2,000 cells/$cm^2$, about 1,000 to about 5,000 cells/$cm^2$, or about 2,000 to about 5,000 cells/$cm^2$. Optionally, at least: about 40%, about 50%, about 60%, or about 70% of the MSCs are viable after a freeze-thaw cycle.

In one embodiment, the amniotic membrane of the placental product comprises fibroblasts in an amount of: at least about 2,000 cells/$cm^2$, at least about 4,000 cells/$cm^2$, about 2,000 to about 9,000 cells/$cm^2$, or about 2,000 to about 9,000 cells/$cm^2$. Optionally, at least: about 40%, about 50%, about 60%, or about 70% of the fibroblasts are viable after a freeze-thaw cycle.

In one embodiment, the amniotic membrane of the placental product comprises stromal cells in an amount of: at least about 4,000, at least about 8,000 cells/$cm^2$, about 4,000 to about 18,000 cells/cm$^2$, or about 4,000 to about 18,000 cells/cm$^2$. Optionally, at least: about 40%, about 50%, about 60%, or about 70% of the stromal cells are viable after a freeze-thaw cycle.

In one embodiment, the amniotic membrane of the placental product comprises epithelial cells in an amount of: at least about 10,000 cells/cm$^2$, at least about 20,000 cells/cm$^2$, at least about 32,000 cells/cm$^2$, about 10,000 to about 72,000 cells/cm$^2$, about 20,000 to about 72,000 cells/cm$^2$, or about 32,000 to about 72,000 cells/cm$^2$ Optionally, at least: about 40%, about 50%, about 60%, or about 70% of the epithelial cells are viable after a freeze-thaw cycle.

In one embodiment, the amniotic membrane of the placental product comprises functional macrophages in an amount of: less than about 3,000 cells/cm$^2$, less than about 1,000 cells/cm$^2$, or less than about 500 cells/cm$^2$.

In one embodiment, the placental product comprises a layer of amniotic epithelial cells.

In one embodiment, the placental product comprises a chorionic membrane but is substantially free of trophoblasts.

In one embodiment, the placental product is substantially free of functional CD14+ macrophages.

In one embodiment, the placental product is substantially free of vascularized tissue-derived cells.

In one embodiment, the placental product is substantially free of trophoblasts, functional CD14+ macrophages, and vascularized tissue-derived cells. Optionally, the placental product comprises viable stromal cells. Optionally, the placental product comprises viable MSCs. Optionally, the placental product comprises viable fibroblasts. Optionally, the placental product comprises viable epithelial cells. Optionally, the placental product comprises viable MSCs, fibroblasts, and epithelial cells.

In one embodiment, the placental product comprises a chorionic membrane but is substantially free of maternal decidual cells.

In one embodiment, the placental product comprises a chorionic membrane but is substantially free of maternal leukocytes and/or trophoblast cells.

In one embodiment, the placental product is substantially free of ex-vivo cultured cells.

Placental Factors

According to the present invention, a placental product comprises native therapeutic factors of the amniotic membrane.

In one embodiment, the factors include one or more of: IGFBP1, adiponectin, α2-macroglobulin, bFGF, EGF, MMP-9, and TIMP1. Optionally, the factors are present in amounts/cm$^2$ that are substantially similar to that of a native amniotic membrane or layer thereof (e.g. ±10% or 20%).

In one embodiment, the factors include IGFBP1, adiponectin, α2-macroglobulin, bFGF, EGF, MMP-9, and TIMP1. Optionally, the factors are present in ratios that are substantially similar to that of a native amniotic membrane or layer thereof. Optionally, the factors are present in amounts/cm$^2$ that are substantially similar to that of a native amniotic membrane or layer thereof (e.g. ±10% or 20%).

In one embodiment, the factors include MMP-9 and TIMP1 in a ratio of about 7 to about 10 (e.g about 7). Optionally, the factors are present in amounts/cm$^2$ that are substantially similar to that of a native amniotic membrane or layer thereof (e.g. ±10% or 20%).

In one embodiment, the factors include one or more (e.g. a majority or all) of the factors listed in Table 16. Optionally, the factors are present in ratios that are substantially similar to that of a native amniotic membrane or layer thereof. Optionally, the factors are present in amounts/cm$^2$ that are substantially similar to that of a native amniotic membrane or layer thereof (e.g. ±10% or 20%).

In one embodiment, the placental product or layer thereof comprises substantially less TNF-α/cm$^2$ than a native amniotic membrane or layer thereof, respectively.

In one embodiment, the placental product or layer thereof secretes substantially less TNF-α/cm$^2$ than a native placental product or layer thereof, respectively.

In one embodiment, the placental product secretes less than about any of: 420 pg/mL, 350 pg/mL, or 280 pg/mL TNF-α into a tissue culture medium upon placing a 2 cm×2 cm piece of the tissue product in a tissue culture medium and exposing the tissue product to a bacterial lipopolysaccharide for about 20 to about 24 hours.

In one embodiment, after cryopreservation and thawing, the placental product secretes less than about any of: 420 pg/mL, 350 pg/mL, or 280 pg/mL TNF-α into a tissue culture medium upon placing a 2 cm×2 cm piece of the tissue product in a tissue culture medium and exposing the tissue product to a bacterial lipopolysaccharide for about 20 to about 24 hours;

In one embodiment, after refrigeration, cryopreservation and thawing, the placental product secretes less than about any of: 420 pg/mL, 350 pg/mL, or 280 pg/mL TNF-α into a tissue culture medium upon placing a 2 cm×2 cm piece of the tissue product in a tissue culture medium and exposing the tissue product to a bacterial lipopolysaccharide for about 20 to about 24 hours.

In one embodiment, the placental product further comprises an exogenously added inhibitor of TNF-α. Optionally, the inhibitor of TNF-α is IL-10.

In one embodiment, the product has been treated with an antibiotic

Architecture

A placental product of the present invention comprises one or more layers which exhibit the architecture of the native amniotic membrane. With the teachings provided herein, the skilled artisan will recognize placental layers that exhibit native architecture, for example, layers that have not been homogenized or treated with collagenase or other enzyme that substantially disrupts the layer.

In one embodiment, the placental product comprises a stromal cell layer with native architecture of the amniotic membrane.

In one embodiment, the placental product comprises a basement membrane with native architecture of the amniotic membrane.

In one embodiment, the placental product comprises an epithelial cell layer with native architecture of the amniotic membrane.

In one embodiment, the placental product comprises a stromal cell layer and a basement layer with native architecture of the amniotic membrane.

In one embodiment, the placental product comprises a stromal layer, a basement layer, and an epithelial cell layer with native architecture of the amniotic membrane.

In one embodiment, the placental product or amniotic membrane thereof has a thickness of about 20 μm to about 50 μm.

In one embodiment, the placental product comprises a chorionic membrane but is substantially free of trophoblasts. In one embodiment, the placental product comprises a basement membrane with native architecture of the chorionic membrane and the chorionic membrane is substantially free of trophoblasts. Optionally, the maternal side of the chorionic membrane comprises fragments of extracellular matrix proteins in a concentration substantially greater than that of a native chorionic membrane. Optionally, the placental product has been treated with Dispase (e.g. Dispase II) and/or a substantial portion of the extracellular matrix protein fragments comprises terminal leucine or phenylalanine.

In one embodiment, the placental product further comprises a chorionic membrane. Optionally, the amniotic membrane and the chorionic membrane in the placental product are associated to one another in the native configuration. Alternatively, the amniotic membrane and the chorionic membrane are not attached to one another in the native configuration.

In one embodiment, the placental product does not comprise a chorionic membrane.

Formulation

According to the present invention, the placental product can be formulated with a cryopreservation medium.

In one embodiment, the cryopreservation medium comprising one or more cell-permeating cryopreservatives, one or more non cell-permeating cryopreservatives, or a combination thereof.

Optionally, the cryopreservation medium comprises one or more cell-permeating cryopreservatives selected from DMSO, a glycerol, a glycol, a propylene glycol, an ethylene glycol, or a combination thereof.

Optionally, the cryopreservation medium comprises one or more non cell-permeating cryopreservatives selected from polyvinylpyrrolidone, a hydroxyethyl starch, a polysacharide, a monosaccharides, a sugar alcohol, an alginate, a trehalose, a raffinose, a dextran, or a combination thereof.

Other examples of useful cryopreservatives are described in "Cryopreservation" (BioFiles Volume 5 Number 4—Sigma-Aldrich® datasheet).

In one embodiment, the cryopreservation medium comprises a cell-permeating cryopreservative, wherein the majority of the cell-permeating cryopreservative is DMSO. Optionally, the cryopreservation medium does not comprise a substantial amount of glycerol.

In one embodiment, the cryopreservation medium comprises DMSO. Optionally, the cryopreservation medium does not comprise glycerol in a majority amount. Optionally, the cryopreservation medium does not comprise a substantial amount of glycerol.

In one embodiment, the cryopreservation medium comprises additional components such as albumin (e.g. HSA or BSA), an electrolyte solution (e.g. PlasmaLyte), or a combination thereof.

In one embodiment, the cryopreservation medium comprises 1% to about 15% albumin by weight and about 5% to about 20% cryopreservative by volume (e.g. about 10%). Optionally, the cryopreservative comprises DMSO (e.g. in a majority amount).

In one embodiment, the placental product is formulated in greater than about 20 ml or greater than about 50 ml of cryopreservation medium. Optionally, the cryopreservative comprises DMSO (e.g. in a majority amount). Optionally, the cryopreservation medium does not comprise a substantial amount of glycerol.

In one embodiment, the placental product is placed on nitrocellulose paper.

In one embodiment, the placenta is cut into a plurality of sections. Optionally, the sections are less than about 10 cm×10 cm. Optionally, the sections are between about 2 cm×2 cm and 5 cm×5 cm.

Manufacture

Overview

A placental product of the present invention can manufactured from a placenta in any suitable manner that provides the technical features taught herein. According to the present invention, a placenta product comprises at least an immunocompatible amniotic membrane.

In one embodiment, a placental product is manufactured by a method comprising:
a. obtaining a placenta,
b. selectively depleting the placenta of immunogenicity; and
c. cryopreserving the placenta.

Optionally, the method comprises a step of removing vascularized tissue from the placenta, for example, by lysing red blood cells, by removing blood clots, or a combination thereof.

Optionally, the method comprises a step of treating the placenta with one or more antibiotics.

Optionally, the method comprises a step of selectively depleting CD14+ macrophages, optionally as demonstrated by a substantial decrease in LPS stimulation of TNFα release.

Optionally, the step of cryopreserving the placenta comprises freezing the placenta in a cryopreservation medium which comprises one or more cell-permeating cryopreservatives, one or more non cell-permeating cryopreservatives, or a combination thereof.

Optionally, the step of cryopreserving the placenta comprises refrigerating for a period of time and then freezing, thereby selectively depleting CD14+ macrophages optionally as demonstrated by a substantial decrease in LPS stimulation of TNFα release.

Optionally, the method comprises retaining a layer of epithelial cells of the amniotic membrane.

Optionally, the method comprises a step of removing the chorionic membrane or portion thereof. Optionally, the method comprises removing trophoblasts from the chorionic membrane while retaining the stromal cell layer, reticular layer, and/or basement membrane of the chorionic membrane.

An examplary placental product of the present invention can be manufactured or provided with a bandage or wound dressing.

Immunocompatability and Selective Depletion

In one embodiment, the invention the placental product is immunocompatible. Immunocompatability can be accomplished by any selective depletion step that removes immunogenic cells or factors or immunogenicity from the placenta (or amniotic membrane thereof).

In one embodiment, the placental product is made immunocompatible by selectively depleting it of functional immunogenic cells. A placenta can be made immunocompatible by selectively removing immunogenic cells from the placenta (or amniotic membrane thereof) relative to therapeutic cells. For example, immunogenic cells can be removed by killing the immunogenic cells or by purification of the placenta there from.

In one embodiment, the placental product is made immunocompatible by selectively depleting trophoblasts, for example, by removal of the trophoblast layer.

In one embodiment, the placenta is made immunocompatible by selective depletion of functional CD14+ macrophages, optionally as demonstrated by a substantial decrease in LPS stimulation of TNFα release or by MLR assay.

In one embodiment, the placenta is made immunocompatible by selective depletion of vascularized tissue-derived cells.

In one embodiment, the placenta is made immunocompatible by selective depletion of functional CD14+ macrophages, trophoblasts, and vascularized tissue-derived cells.

In one embodiment, the placenta product is made immunocompatible by selective depletion of trophoblasts and/or CD14+ macrophages, optionally as demonstrated by a substantial decrease in LPS stimulation of TNFα release or by MLR assay.

Trophoblast Removal

In one embodiment, Immunocompatability (or selective depletion) is accomplished by removal or depletion of trophoblasts from the placental product. Trophoblasts can be removed by removing the chorionic membrane from the placental product or by removing trophoblasts from the chorionic membrane while retaining at least one of the basement layer, reticular layer, or stromal cell layer of the chorionic membrane. Surprisingly, such a placental product has one or more of the following superior features:

a. is substantially non-immunogenic;
b. provides remarkable healing time; and
c. provides enhanced therapeutic efficacy.

In one embodiment, trophoblasts are removed while retaining the basement layer, reticular layer, and/or stromal cell layer of the chorionic membrane.

Trophoblasts can be removed in any suitable manner which substantially diminishes the trophoblast content of the placental product. Optionally, the trophoblasts are selectively removed or otherwise removed without eliminating a substantial portion of one or more therapeutic components from the chorionic membrane (e.g. MSCs, placental factors, etc). Optionally, a majority (e.g. substantially all) of the trophoblasts are removed.

One method of removing trophoblasts comprises treating the placenta (e.g. chorion or amnio-chorion) with a digestive enzyme such as dispase (e.g. dispase II) and separating the trophoblasts from the placenta. Optionally, the step of separating comprises mechanical separation such as peeling or scraping. Optionally, scraping comprises scraping with a soft instrument such as a finger.

One method of removing trophoblasts comprises treating the chorionic membrane with dispase for about 30 to about 45 minutes separating the trophoblasts from the placenta. Optionally, the dispase is provided in a solution of about less than about 1% (e.g. about 0.5%). Optionally, the step of separating comprises mechanical separation such as peeling or scraping. Optionally, scraping comprises scraping with a soft instrument such as a finger.

Useful methods of removing trophoblasts from a placenta (e.g. chorion) are described by Portmann-Lanz et al. ("Placental mesenchymal stem cells as potential autologous graft for pre- and perinatal neuroregeneration"; American Journal of Obstetrics and Gynecology (2006) 194, 664-73), ("Isolation and characterization of mesenchymal cells from human fetal membranes"; Journal Of Tissue Engineering And Regenerative Medicine 2007; 1: 296-305.), and (Concise Review: Isolation and Characterization of Cells from Human Term Placenta: Outcome of the First International Workshop on Placenta Derived Stem Cells").

In one embodiment, trophoblasts are removed before cryopreservation.

Macrophage Removal

In one embodiment, functional macrophages are depleted or removed from the placental product. Surprisingly, such a placental product has one or more of the following superior features:

a. is substantially non-immunogenic;
b. provides remarkable healing time; and
c. provides enhanced therapeutic efficacy.

Functional macrophages can be removed in any suitable manner which substantially diminishes the macrophage content of the placental product. Optionally, the macrophages are selectively removed or otherwise removed without eliminating a substantial portion of one or more therapeutic components from the placenta (e.g. MSCs, placental factors, etc). Optionally, a majority (e.g. substantially all) of the macrophages are removed.

One method of removing immune cells such as macrophages comprises killing the immune cells by rapid freezing rates such as 60-100° C./min.

Although immune cells can be eliminated by rapid freezing rates, such a method can also be detrimental to therapeutic cells such as stromal cells (e.g. MSCs). The present inventors have discovered a method of selectively killing CD14+ macrophages can be selectively killed by refrigerating the placenta for a period of time (e.g. for at least about 10 min such as for about 30-60 mins) at a temperature above freezing (e.g. incubating at 2-8° C.) and then freezing the placenta (e.g. incubating at −80° C.±5° C.). Optionally, the step of freezing comprises freezing at a rate of less than 10°/min (e.g. less than about 5°/min such as at about 1°/min).

In one embodiment, the step of refrigerating comprises soaking the placenta in a cryopreservation medium (e.g. containing DMSO) for a period of time sufficient to allow the cryopreservation medium to penetrate (e.g. equilibrate with) the placental tissues. Optionally, the step of freezing comprises reducing the temperature at a rate of about 1°/min. Optionally, the step of freezing comprises freezing at a rate of less than 10°/min (e.g. less than about 5°/min such as at about 1°/min).

In one embodiment, the step of refrigerating comprises soaking the placenta in a cryopreservation medium (e.g. containing DMSO) at a temperature of about −10-15° C. (e.g. at 2-8° C.) for at least about any of: 10 min, 20 min, 30 min, 40 min, or 50 min. In another embodiment the step of refrigerating comprises soaking the placenta in a cryopreservation medium (e.g. containing DMSO) at a temperature of about −10-15° C. (e.g. at 2-8° C.) for about any of: 10-120, 20-90 min, or 30-60 min. Optionally, the step of freezing comprises freezing at a rate of less than 10°/min (e.g. less than about 5°/min such as at about 1°/min).

Removal of Vascularized Tissue-Derived Cells

In one embodiment, vascularized tissue-derived cells (or vascularized tissue) are depleted or removed from the placental product. Surprisingly, such a placental product has one or more of the following superior features:

a. is substantially non-immunogenic;
b. provides remarkable healing time; and
c. provides enhanced therapeutic efficacy.

Vascularized tissue-derived cells can be removed in any suitable manner which substantially diminishes such cell content of the placental product. Optionally, the vascularized tissue-derived cells are selectively removed or otherwise removed without eliminating a substantial portion of one or more therapeutic components from the placenta (e.g. MSCs, placental factors, etc).

In one embodiment, removal of vascularized tissue-derived cells comprises rinsing the amniotic membrane (e.g. with buffer such as PBS) to remove gross blood clots and any excess blood cells.

In one embodiment, removal of vascularized tissue-derived cells comprises treating the amniotic membrane with an anticoagulant (e.g. citrate dextrose solution).

In one embodiment, removal of vascularized tissue-derived cells comprises rinsing the amniotic membrane (e.g. with buffer such as PBS) to remove gross blood clots and any excess blood cells, and treating the amniotic membrane with an anticoagulant (e.g. citrate dextrose solution).

In one embodiment, the chorionic membrane is retained and removal of vascularized tissue-derived cells comprises separating the chorion from the placenta by cutting around the placental skirt on the side opposite of the umbilical cord. The chorion on the umbilical side of the placenta is not removed due to the vascularization on this side.

In one embodiment, the chorionic membrane is retained and removal of vascularized tissue-derived cells comprises separating the chorion from the placenta by cutting around the placental skirt on the side opposite of the umbilical cord and rinsing the amniotic membrane and chorionic membrane (e.g. with buffer such as PBS) to remove gross blood clots and any excess blood cells.

In one embodiment, the chorionic membrane is retained and removal of vascularized tissue-derived cells comprises separating the chorion from the placenta by cutting around the placental skirt on the side opposite of the umbilical cord and treating the amniotic membrane and chorionic membrane with an anticoagulant (e.g. citrate dextrose solution).

In one embodiment, the chorionic membrane is retained and removal of vascularized tissue-derived cells comprises separating the chorion from the placenta by cutting around the placental skirt on the side opposite of the umbilical cord, rinsing the chorionic membrane amniotic membrane (e.g. with buffer such as PBS) to remove gross blood clots and any excess blood cells, and treating the amniotic membrane with an anticoagulant (e.g. citrate dextrose solution).

Selective Depletion of Immunogenicity as Demonstrated by a Substantial Decrease in LPS Stimulation of TNFα Release.

In one embodiment, the placental product is selectively depleted of immunogenicity as demonstrated by a reduction in LPS stimulated TNF-α release. In one embodiment, the placental product is selectively depleted of macrophages.

In one embodiment, TNF-α is depleted by killing or removal of macrophages.

In one embodiment, TNF-α is functionally depleted by treatment with IL-10, which suppresses TNF-α secretion.

Preservation

A placental product of the present invention may be used fresh or may be preserved for a period of time. Surprisingly, cryopreservation results in immunocompatible placental products.

In one embodiment, a placental product is cryopreserved. A placental product may be cryopreserved by incubation at freezing temperatures (e.g. a −80° C.±5° C.) in a cryopreservative medium.

Cryopreservation can comprise, for example, incubating the placental product at 4° C. for 30-60 min, and then incubating at −80° C. until use. The placental product may then be thawed for use. Optionally, the placental product is cryopreserved in a manner such that cell viability is retained surprisingly well after a freeze-thaw cycle.

In one embodiment, cryopreservation comprises storage in a cryopreservation medium comprising one or more cell-permeating cryopreservatives, one or more non cell-permeating cryopreservatives, or a combination thereof. Optionally, the cryopreservation medium comprises one or more cell-permeating cryopreservatives selected from DMSO, a glycerol, a glycol, a propylene glycol, an ethylene glycol, or a combination thereof. Optionally, the cryopreservation medium comprises one or more non cell-permeating cryopreservatives selected from polyvinylpyrrolidone, a hydroxyethyl starch, a polysacharide, a monosaccharides, a sugar alcohol, an alginate, a trehalose, a raffinose, a dextran, or a combination thereof. Other examples of useful cryopreservatives are described in "Cryopreservation" (BioFiles Volume 5 Number 4—Sigma-Aldrich® datasheet).

In one embodiment, the cryopreservation medium comprises a cell-permeating cryopreservative, wherein the majority of the cell-permeating cryopreservative is DMSO. Optionally, the cryopreservation medium does not comprise a substantial amount of glycerol.

In one embodiment, the cryopreservation medium comprises DMSO. Optionally, the cryopreservation medium does not comprise glycerol in a majority amount. Optionally, the cryopreservation medium does not comprise a substantial amount of glycerol.

In one embodiment, the cryopreservation medium comprises additional components such as albumin (e.g. HSA or BSA), an electrolyte solution (e.g. PlasmaLyte), or a combination thereof.

In one embodiment, the cryopreservation medium comprises 1% to about 15% albumin by weight and about 5% to about 20% cryopreservative by volume (e.g. about 10%). Optionally, the cryopreservative comprises DMSO (e.g. in a majority amount).

In one embodiment, cryopreservation comprises placing the placenta on nitrocellulose paper.

In one embodiment, the placenta is cut into a plurality of sections before cryopreservation. Optionally, the sections are placed on nitrocellulose paper before refrigeration.

Methods of Use

The placental products of the present invention may be used to treat any tissue injury. A method of treatment may be provided, for example, by administering to a subject in need thereof, a placental product of the present invention.

A typical administration method of the present invention is topical administration. Administering the present invention can optionally involve administration to an internal tissue where access is gained by a surgical procedure.

Placental products can be administered autologously, allogeneically or xenogeneically.

In one embodiment, a present placental product is administered to a subject to treat a wound. Optionally, the wound is a laceration, scrape, thermal or chemical burn, incision, puncture, or wound caused by a projectile. Optionally, the wound is an epidermal wound, skin wound, chronic wound, acute wound, external wound, internal wounds, congenital wound, ulcer, or pressure ulcer. Such wounds may be accidental or deliberate, e.g., wounds caused during or as an adjunct to a surgical procedure. Optionally, the wound is closed surgically prior to administration.

In one embodiment, a present placental product is administered to a subject to treat a burn. Optionally, the burn is a first-degree burn, second-degree burn (partial thickness burns), third degree burn (full thickness burns), infection of burn wound, infection of excised and unexcised burn wound, loss of epithelium from a previously grafted or healed burn, or burn wound impetigo.

In one embodiment, a present placental product is administered to a subject to treat an ulcer, for example, a diabetic ulcer (e.g. foot ulcer).

In one embodiment, a placental product is administered by placing the placental product directly over the skin of the subject, e.g., on the stratum corneum, on the site of the wound, so that the wound is covered, for example, using an adhesive tape. Additionally or alternatively, the placental product may be administered as an implant, e.g., as a subcutaneous implant.

In one embodiment, a placental product is administered to the epidermis to reduce rhtids or other features of aging skin. Such treatment is also usefully combined with so-called cosmetic surgery (e.g. rhinoplasty, rhytidectomy, etc.).

In one embodiment, a placental product is administered to the epidermis to accelerate healing associated with a dermal ablation procedure or a dermal abrasion procedure (e.g. including laser ablation, thermal ablation, electric ablation, deep dermal ablation, sub-dermal ablation, fractional ablation, and microdermal abrasion).

Other pathologies that may be treated with placental products of the present invention include traumatic wounds (e.g. civilian and military wounds), surgical scars and wounds, spinal fusions, spinal cord injury, avascular necrosis, reconstructive surgeries, ablations, and ischemia.

In one embodiment, a placental product of the present invention is used in a tissue graft procedure. Optionally, the placental product is applied to a portion of the graft which is then attached to a biological substrate (e.g. to promote healing and/or attachment to the substrate). By way of non-limiting example, tissues such as skin, cartilage, ligament, tendon, periosteum, perichondrium, synovium, fascia, mesenter and sinew can be used as tissue graft.

In one embodiment, a placental product is used in a tendon or ligament surgery to promote healing of a tendon or ligament. Optionally, the placental product is applied to portion of a tendon or ligament which is attached to a bone. The surgery can be any tendon or ligament surgery, including, e.g. knee surgery, shoulder, leg surgery, arm surgery, elbow surgery, finger surgery, hand surgery, wrist surgery, toe surgery, foot surgery, ankle surgery, and the like. For example, the placental product can be applied to a tendon or ligament in a grafting or reconstruction procedure to promote fixation of the tendon or ligament to a bone.

Through the insight of the inventors, it has surprisingly been discovered that placental products of the present invention provide superior treatment (e.g. healing time and/or healing strength) for tendon and ligament surgeries. Tendon and ligament surgeries can involve the fixation of the tendon or ligament to bone. Without being bound by theory, the present inventors believe that osteogenic and/or chondrogenic potential of MSCs in the present placental products promotes healing process and healing strength of tendons or ligaments. The present inventors believe that the present placental products provide an alternative or adjunctive treatment to periosteum-based therapies. For example, useful periosteum based treatments are described in Chen et al. ("Enveloping the tendon graft with periosteum to enhance tendon-bone healing in a bone tunnel: A biomechanical and histologic study in rabbits"; Arthroscopy. 2003 March; 19(3):290-6), Chen et al. ("Enveloping of periosteum on the hamstring tendon graft in anterior cruciate ligament reconstruction"; Arthroscopy. 2002 May-June; 18(5):27E), Chang et al. ("Rotator cuff repair with periosteum for enhancing tendon-bone healing: a biomechanical and histological study in rabbits"; Knee Surgery, Sports Traumatology, Arthroscopy Volume 17, Number 12, 1447-1453), each of which are incorporated by reference.

As non-limiting example of a method of tendon or ligament surgery, a tendon is sutured to and/or wrapped or enveloped in a placental membrane and the tendon is attached to a bone. Optionally, the tendon is placed into a bone tunnel before attached to the bone.

In one embodiment, the tendon or ligament surgery is a graft procedure, wherein the placental product is applied to the graft. Optionally, the graft is an allograft, xenograft, or an autologous graft.

In one embodiment, the tendon or ligament surgery is repair of a torn ligament or tendon, wherein the placental product is applied to the torn ligament or tendon.

Non-limiting examples of tendons to which a placental product can be applied include a digitorum extensor tendon, a hamstring tendon, a bicep tendon, an Achilles Tendon, an extensor tendon, and a rotator cuff tendon.

In one embodiment, a placental product of the present invention is used to reduce fibrosis by applying the placental product to a wound site.

In one embodiment, a placental product of the present invention is used as an anti-adhesion wound barrier, wherein the placental product is applied to a wound site, for example, to reduce fibrosis (e.g. postoperative fibrosis).

Non-limiting examples of wound sites to which the placental product can be applied include those that are surgically induced or associated with surgery involving the spine, laminectomy, knee, shoulder, or child birth, trauma related wounds or injuries, cardiovascular procedures, angiogenesis stimulation, brain/neurological procedures, burn and wound care, and ophthalmic procedures. For example, optionally, the wound site is associated with surgery of the spine and the stromal side of the placental product is applied to the dura (e.g. the stromal side facing the dura). Direction for such procedures, including the selection of wound sites and/or methodologies, can be found, for example, in WO 2009/132186 and US 2010/0098743, which are hereby incorporated by reference.

A placental product of the present invention can optionally be used to reduce adhesion or fibrosis of a wound. Postoperative fibrosis is a natural consequence of all surgical wound healing. By example, postoperative peridural adhesion results in tethering, traction, and compression of the thecal sac and nerve roots, which cause a recurrence of hyperesthesia that typically manifests a few months after laminectomy surgery. Repeated surgery for removal of scar tissue is associated with poor outcome and increased risk of injury because of the difficulty of identifying neural structures that are surrounded by scar tissue. Therefore, experimental and clinical studies have primarily focused on preventing the adhesion of scar tissue to the dura matter and nerve roots. Spinal adhesions have been implicated as a major contributing factor in failure of spine surgery. Fibrotic scar tissue can cause compression and tethering of nerve roots, which can be associated with recurrent pain and physical impairment.

Without being bound by theory, the present inventors believe that placental products taught herein are useful to reduce adhesion or fibrosis of a wound, at least in part, because the placental products can perform the very critical function in-situ of providing a immunoprivileged environment (i.e. relatively high resistance against immune responses) in the human development process. One advantage of the wound dressings and processes of the present invention is that an anti-adhesion barrier is provided which can be used to prevent adhesions following surgery, and in particular following back surgery.

In the preceding paragraphs, use of the singular may include the plural except where specifically indicated. As used herein, the words "a," "an," and "the" mean "one or more," unless otherwise specified. In addition, where aspects of the present technology are described with reference to lists of alternatives, the technology includes any individual member or subgroup of the list of alternatives and any combinations of one or more thereof.

The disclosures of all patents and publications, including published patent applications, are hereby incorporated by reference in their entireties to the same extent as if each patent and publication were specifically and individually incorporated by reference.

It is to be understood that the scope of the present technology is not to be limited to the specific embodiments described above. The present technology may be practiced other than as particularly described and still be within the scope of the accompanying claims.

Likewise, the following examples are presented in order to more fully illustrate the present technology. They should in no way be construed, however, as limiting the broad scope of the technology disclosed herein.

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Other features and embodiments of the present technology will become apparent from the following examples which are given for illustration of the present technology rather than for limiting its intended scope.

Example 1 Characterization of Placental Membranes

Cells in placental membranes were characterized by Fluorescence Activated Cell Sorting (FACS) demonstrated the presence of stromal cells (Mesenchymal Stem Cell-like cells) in addition to fetal epithelial cells and fibroblasts.

One unique characteristic of the presently disclosed placental products is the presence of MSCs, which have been shown to be one of three types of cells (in addition to epithelial cells and fibroblasts) that are important for wound healing. Placental membranes secrete a variety of factors involved in wound healing such as angiogenic factors, factors supporting proliferation and migration of epithelial cells and fibroblasts, factors attracting endothelial stem cells from blood circulation to the wound site, antibacterial factors, and others.

Evaluation of proteins secreted by examplary placental products of the invention in comparison to Apligraf and Dermagraft demonstrated a number of growth factors present in the tested products that are involved in wound healing. Examples are Vascular Endothelial Growth Factor (VEGF), Platelet-Derived Growth Factor (PDGF), Transforming Growth Factor (TGF) and others. However, several unique factors including Epidermal Growth Factor (EGF), which is one of the key factors for wound healing, are present in placental membranes and absent in Apligraf and Dermagraft. Also, placental membranes have a favorable protease-to-protease inhibitor ratio for wound healing. In an in vitro model of wound healing (cell migration assay, disclosed herein), the present inventors have demonstrated that placental membranes secrete factors promoting cell migration that will support wound closure.

Example 2 Exemplary Manufacturing Process of a Placental Product

In one embodiment, the present invention is a method of manufacturing a placental product comprising an amniotic membrane and optionally a chorionic membrane from placenta post partum. One such method is:
a. Remove umbilical cord close to placental surface,
b. Blunt dissect of the amnion to placental skirt,
c. Flip placenta over and completely remove amnion,
d. Rinse amnion in PBS to remove red blood cells,
e. Rinse amnion once with 11% ACD-A solution to assist in red blood cell removal,
f. Rinse amnion with PBS to remove ACD-A solution,
g. Use PBS to remove any remaining blood from the amnion,
h. Gently remove the connective tissue layer from the amnion,
i. Place the amnion in PBS and set aside,
j. Place the amnion into a bottle containing antibiotic solution and incubate at 37° C.±2° C. for 24-28 hrs,
k. Remove bottle from the incubator and rinse membrane with PBS to remove antibiotic solution,
l. Mount amnion (epithelial side up) on reinforced nitrocellulose paper and cut to size,
m. Place into an FP-90 cryobag and heat seal,
n. Add 50 mL cryopreservation solution to the bag through a syringe and remove any air trapped within the bag with the syringe,
o. Tube seal the solution line on the FP-90 bag,
P. Place filled bag into secondary bag and heat seal,
q. Place unit into packaging carton,
r. Refrigerate at 2-8° C. for 30-60 minutes, Freeze at −80° C.±5° C. inside a Styrofoam container.

Example 3 Examplary Manufacturing Process of a Placental Product Containing an Amniotic Membrane and a Chorionic Membrane In one embodiment, the present invention is a method of manufacturing a placental product comprising an amniotic membrane and optionally a chorionic membranes from placenta post partum. One such method is:
a. Remove umbilical cord close to placental surface,
b. Blunt dissect of the amnion to placental skirt,
c. Flip placenta over and completely remove amnion,
d. Remove chorion by cutting around placental skirt,
e. Rinse both membranes in PBS to remove red blood cells,
f. Rinse both membranes once with 11% ACD-A solution to assist in red blood cell removal,
g. Rinse both membranes with PBS to remove ACD-A solution, \
h. Treat chorion in 0.5% dispase solution at 37° C.±2° C. for 30-45 minutes, optionally, during dispase incubation period, use PBS to remove any remaining blood from the amnion,
i. Gently remove the connective tissue layer from the amnion,
j. Place the amnion in PBS and set aside,
k. When dispase treatment is complete, rinse chorion with PBS to remove dispase solution,
l. Gently remove trophoblast layer from the chorion,
m. Place the amnion and chorion each into a bottle containing antibiotic solution and incubate at 37° C.±2° C. for 24-28 hrs, n. Remove bottles from the incubator and rinse each membrane with PBS to remove antibiotic solution,
o. Mount amnion (epithelial side up) or chorion on reinforced nitrocellulose paper and cut to size,
p. Place each piece into an FP-90 cryobag and heat seal,
q. Add 50 mL cryopreservation solution to the bag through a syringe and remove any air trapped within the bag with the syringe,
r. Tube seal the solution line on the FP-90 bag,
s. Place filled bag into secondary bag and heat seal,
t. Place unit into packaging carton,
u. Refrigerate at 2-8° C. for 30-60 minutes,
v. Freeze at −80° C.±5° C. inside a Styrofoam container.

Example 4 Exemplary Placental Product Manufacturing Process

One method manufacturing a placental product comprising an amniotic membrane according to the presently disclosed manufacturing procedure is as follows:

One method of manufacturing a placental product comprising a chorionic membrane product and an amniotic membrane product according to the presently disclosed manufacturing procedure was as follows:

The placenta was processed inside a biological safety cabinet. The umbilical cord was first removed, and the amniotic membrane was peeled from the underlying chorionic membrane using blunt dissection. The membrane was rinsed with phosphate buffered saline (PBS) (Gibco Invitrogen, Grand Island, N.Y.) to remove gross blood clots and any excess blood cells. The membrane was then washed with 11% anticoagulant citrate dextrose solution (USP) formula A (ACD-A) (Baxter Healthcare Corp., Deerfield, Ill.) in saline (Baxter Healthcare Corp., Deerfield, Ill.) to remove remaining blood cells.

The stromal side of the amnion was cleaned by gently scraping away any remaining connective tissue.

The amnion was then each disinfected in 500 mL of antibiotic solution consisting of gentamicin sulfate (50 µg/mL) (Abraxis Pharmaceutical Products, Schaumburg, Ill.), vancomycin HCl (50 µg/mL) (Hospira Inc., Lake Forest, Ill.), and amphotericin B (2.5 µg/mL) (Sigma Aldrich, St. Louis, Mo.) in DMEM at 37° C.±2° C. for 24-28 hours. Vented caps were used with the incubation flasks. After the incubation period, the membrane was washed with PBS to remove any residual antibiotic solution.

The membrane was mounted on Optitran BA-S 85 reinforced nitrocellulose paper (Whatman, Dassel, Germany) and cut to the appropriate size prior to packaging into an FP-90 cryobag (Charter Medical Ltd., Winston-Salem, N.C.). The stromal side of the amnion was mounted towards the nitrocellulose paper. Once the membrane unit was placed into the FP-90 cryobag and the cryobag was heat sealed, 50 mL of a cryopreservation solution containing 10% dimethyl sulfoxide (DMSO) (Bioniche Teo. Inverin Co., Galway, Ireland) and 5% human serum albumin (HSA) (Baxter, West Lake Village, Calif.) in PlasmaLyte-A (Baxter Healthcare Corp., Deerfield, Ill.) were added through the center tubing line. Any excess air was removed, and the tubing line was subsequently sealed.

The FP-90 cryobag was placed into a mangar bag (10 in.×6 in.) (Mangar Industries, New Britain, Pa.), which was then heat sealed. The mangar bag was placed into a packaging carton (10.5 in.×6.5 in.×0.6 in.) (Diamond Packaging, Rochester, N.Y.). All cartons were refrigerated at 2-8° C. for 30-60 minutes prior to freezing at −80° C.±5° C. inside a Styrofoam container.

Example 5 Exemplary Manufacturing Process of a Placental Product Comprising Chorionic Membrane and Amniotic Membrane One method of manufacturing a placental product comprising a chorionic membrane product and an amniotic membrane product according to the presently disclosed manufacturing procedure was as follows:

The placenta was processed inside a biological safety cabinet. The umbilical cord was first removed, and the amniotic membrane was peeled from the underlying chorionic membrane using blunt dissection. Subsequently, the chorion was removed by cutting around the placental skirt on the side opposite of the umbilical cord. The chorion on the umbilical side of the placenta was not removed due to the vascularization on this side. Both membranes were rinsed with phosphate buffered saline (PBS) (Gibco Invitrogen, Grand Island, N.Y.) to remove gross blood clots and any excess blood cells. The membranes were then washed with 11% anticoagulant citrate dextrose solution (USP) formula A (ACD-A) (Baxter Healthcare Corp., Deerfield, Ill.) in saline (Baxter Healthcare Corp., Deerfield, Ill.) to remove remaining blood cells.

The chorion was then incubated in 200 mL of a 0.5% dispase (BD Biosciences, Bedford, Mass.) solution in Dulbecco's modified eagles media (DMEM) (Lonza, Walkersville, Md.) at 37° C.±2° C. for 30-45 minutes to digest the connective tissue layer between the chorion and adjacent trophoblast layer. During this incubation period, the stromal side of the amnion was cleaned by gently scraping away any remaining connective tissue. Once the chorion incubation period was complete, the chorion was rinsed with PBS to remove the dispase solution. Subsequently, the trophoblast layer was removed by gently peeling or scraping away these maternal decidual cells.

The amnion and chorion were then each disinfected in 500 mL of antibiotic solution consisting of gentamicin sulfate (50 µg/mL) (Abraxis Pharmaceutical Products, Schaumburg, Ill.), vancomycin HCl (50 µg/mL) (Hospira Inc., Lake Forest, Ill.), and amphotericin B (2.5 µg/mL) (Sigma Aldrich, St. Louis, Mo.) in DMEM at 37° C.±2° C. for 24-28 hours. Vented caps were used with the incubation flasks. After the incubation period, the membranes were washed with PBS to remove any residual antibiotic solution.

The membranes were mounted on Optitran BA-S 85 reinforced nitrocellulose paper (Whatman, Dassel, Germany) and cut to the appropriate size prior to packaging into an FP-90 cryobag (Charter Medical Ltd., Winston-Salem, N.C.). For the amnion, the stromal side was mounted towards the nitrocellulose paper. Once a membrane unit was placed into the FP-90 cryobag and the cryobag was heat sealed, 50 mL of a cryopreservation solution containing 10% dimethyl sulfoxide (DMSO) (Bioniche Teo. Inverin Co., Galway, Ireland) and 5% human serum albumin (HSA) (Baxter, West Lake Village, Calif.) in PlasmaLyte-A (Baxter Healthcare Corp., Deerfield, Ill.) were added through the center tubing line. Any excess air was removed, and the tubing line was subsequently sealed.

The FP-90 cryobag was placed into a mangar bag (10 in.×6 in.) (Mangar Industries, New Britain, Pa.), which was then heat sealed. The mangar bag was placed into a packaging carton (10.5 in.×6.5 in.×0.6 in.) (Diamond Packaging, Rochester, N.Y.). All cartons were refrigerated at 2-8° C. for 30-60 minutes prior to freezing at −80° C.±5° C. inside a Styrofoam container.

Example 6 Quantitative Evaluation of Cell Number and Cell Viability after Enzymatic Digestion of Placental Membranes Amnion and chorion membranes and present placental products (from above) were evaluated for cell number and cell viability throughout the process. These analyses were performed on fresh placental tissue (prior to the antibiotic treatment step), placental tissue post antibiotic treatment, and product units post thaw. Cells were isolated from the placental membranes using enzymatic digestion. For the frozen product units, the FP-90 cryobags were first removed from the packaging cartons and mangar bags. Then the FP-90 cryobags were thawed for 2-3 minutes in a room temperature water bath. Early experiments involved the use of a 37° C.±2° C. water bath. After thaw, the placental membranes were removed from the FP-90 cryobag and placed into a reservoir containing saline (Baxter Healthcare Corp., Deerfield, Ill.) for a minimum of 1 minute and a maximum of 60 minutes. Each membrane was detached from the reinforced nitrocellulose paper prior to digestion.

Amniotic membranes were digested with 40 mL of 0.75% collagenase (Worthington Biochemical Corp., Lakewood, N.J.) solution at 37° C.±2° C. for 20-40 minutes on a rocker. After collagenase digestion, the samples were centrifuged at 2000 rpm for 10 minutes. The supernatant was removed, and 40 mL of 0.05% trypsin-EDTA (Lonza, Walkersville, Md.) were added and incubated at 37° C.±2° C. for an additional 5-15 minutes on a rocker. The trypsin was warmed to 37° C.±2° C. in a water bath prior to use. After trypsin digestion, the suspension was filtered through a 100 µm cell strainer nylon filter to remove any debris. Centrifugation at 2000 rpm for 10 minutes was performed, and supernatant was removed. Cell pellets were reconstituted with a volume of PlasmaLyte-A that was proportional to the pellet size, and 20 µL of the resuspended cell suspension were mixed with 80 µL of trypan blue (Sigma Aldrich, St. Louis, Mo.) for counting. The cell count sample was placed into a hemocytometer and evaluated using a microscope.

Chorionic membranes were digested with 25 mL of 0.75% collagenase solution at 37° C.±2° C. for 20-40 minutes on a rocker. After collagenase digestion, the suspension was filtered through a 100 µm cell strainer nylon filter to remove any debris. Centrifugation at 2000 rpm for 10 minutes was performed, and supernatant was removed. Cell pellets were reconstituted with a volume of PlasmaLyte-A that was proportional to the pellet size, and 20 µL of the resuspended cell suspension were mixed with 80 µL of trypan blue for counting. The cell count sample was placed into a hemocytometer and evaluated using a microscope.

Placenta membranes were analyzed prior to any processing to determine the initial characteristics of the membranes. Table 1 contains the average cell count per $cm^2$ and cell viability values for the amniotic and chorionic membranes from 32 placenta lots.

The average cell count per $cm^2$ for the amniotic membrane was 91,381 cells with a corresponding average cell viability of 84.5%. For the chorionic membrane, the average cell count per $cm^2$ was 51,614 cells with a corresponding cell viability of 86.0%.

As certain methods of manufacture are taught herein to retain amniotic membrane cells, these data further demonstrate that the present methods can produce placental products that comprise an amniotic membrane containing about 10.000 to about 360,000 cells/$cm^2$.

Since the amniotic membrane consists of epithelial cells and stromal cells, experiments were conducted to determine the ratio of epithelial cells to stromal cells. Amniotic membranes from 3 placenta lots were analyzed. First, a 5 cm×5 cm piece of amniotic membrane was digested with approximately 25 mL of 0.05% trypsin-EDTA (Lonza, Walkersville, Md.) at 37° C.±2° C. in a water bath for 30 minutes. After the incubation step, epithelial cells were removed by gently scraping the cells from the membrane. After rinsing with PBS (Gibco Invitrogen, Grand Island, N.Y.), the membrane was subsequently digested in the same manner as chorionic membrane (described above). In addition, another intact 5 cm×5 cm piece of amniotic membrane was digested using the standard procedure (described above) to determine the total number of cells. The percentage of stromal cells was then determined by dividing the cell count from the amniotic membrane with the epithelial cells removed with the cell count from the intact membrane.

Results indicate that 19% of the total cells were stromal cells. Therefore, approximately 17,362 stromal cells were present in amniotic membrane with approximately 74,019 epithelial cells. These data indicated that there are approximately 3 times more stromal cells in chorionic membranes as compared to amniotic membranes. As certain methods of manufacture are taught herein to retain stromal cells, this ratio demonstrates that the present methods can produce placental products that comprise a chorionic membrane and amniotic membrane, wherein the chorionic membrane comprises about 2 to about 4 times more stromal cells relative to the amniotic membrane.

TABLE 1

Cell count per $cm^2$ and cell viability values from fresh placental tissue from 32 donors.

| Membrane | Statistics | Cell Count per $cm^2$ | Cell Viability |
|---|---|---|---|
| Amnion | Average | 91,381 | 84.5% |
|  | SD | 49,597 | 3.7% |
| Chorion | Average | 51,614 | 86.0% |
|  | SD | 25,478 | 4.7% |

Cell count and cell viability was assessed after the antibiotic treatment step. Table 2 provides the results from these analyses. Cell recoveries from this step for the amniotic membrane and the chorionic membrane were 87.7% and 70.3%, respectively.

TABLE 2

Cell count per $cm^2$, cell viability, and process (antibiotic treatment) cell recovery values for post antibiotic placental tissue from 28 donors.

| Membrane | Statistics | Cell Count per $cm^2$ | Cell Viability | Process Cell Recovery |
|---|---|---|---|---|
| Amnion | Average | 75,230 | 84.4% | 87.7% |
|  | SD | 46,890 | 4.2% | 49.4% |
| Chorion | Average | 33,028 | 85.6% | 70.3% |
|  | SD | 18,595 | 4.4% | 31.1% |

Example 7 Development of a Placental Product Cryopreservation Procedure

Cryopreservation is a method that provides a source of tissues and living cells. A main objective of cryopreservation is to minimize damage to biological materials during low temperature freezing and storage. Although general cryopreservation rules are applicable to all cells, tissues, and organs, optimization of the cryopreservation procedure is required for each type of biological material. The present application discloses a cryopreservation procedure for placental membrane products that can selectively deplete immunogenic cells from the placental membranes; and preserve viability of other beneficial cells that are the primary source of factors for the promotion of healing.

During cryopreservation method development for placental membranes, the present inventors evaluated key parameters of cryopreservation including volume of cryopreservative solution, effect of tissue equilibration prior to freezing, and cooling rates for a freezing procedures.

Acceptance of tissue allografts in the absence of immunosuppression will depend on the number of satellite immune cells present in the tissue. Cryopreservation is an approach which can be utilized to reduce tissue immunogenicity. This approach is based on differential susceptibility of different cell types to freezing injury in the presence of DMSO; leukocytes are sensitive to fast cooling rates. The freezing rate of 1° C./min is considered optimal for cells and tissues including immune cells. Rapid freezing rates such as 60-100° C./min eliminate immune cells. However, this type of procedure is harmful to other tissue cells, which are desirable for preservation according to the present invention. The developed cryopreservation procedure utilized a cryopreservation medium containing 10% DMSO, which is a key component protecting cells from destruction when water forms crystals at low temperatures. The second step of cryopreservation was full equilibration of placental membrane in the cryopreservation medium, which was achieved by soaking membranes in the cryopreservation medium for 30-60 min at 4° C. This step allowed DMSO to penetrate the placental tissues. Although there are data in the literature showing that tissue equilibration prior to freezing affects survival of immune cells (Taylor & Bank, Cryobiology, 1988, 25:1), It was unexpectedly found that 30-60 min placental membrane equilibration in a DMSO-containing solution at 2-8° C. increases sensitivity of immune cells to freezing so that these type of cells cannot withstand freezing even at a 1° C./min freezing rate.

Temperature mapping experiments were performed to analyze the temperature profiles of potential cryopreservation conditions for the membrane products. These results are illustrated in FIG. 1. Eight (8) FP-90 cryobags were filled with either 20 mL or 50 mL of cryopreservation solution, and temperature probes were placed inside each cryobag. The first set of parameters (conditions 1 through 4 of FIG. 1a through FIG. 1d, respectively) involved a 30-minute refrigeration (2-8° C.) step prior to freezing (-80° C.±5° C.). In addition, the analysis involved freezing of the cryobags either inside a Styrofoam container or on the freezer shelf. The second set of parameters (conditions 5 through 8 of FIG. 1e through FIG. 1h, respectively) involved direct freezing (-80° C.±5° C.) of the cryobags either inside a Styrofoam container or on the freezer shelf. The results indicated that condition 6 and condition 2 exhibited the most gradual temperature decreases. Gradual temperature decreases are typically desired in order to preserve cell viability. The difference between condition 6 and condition 2 was that condition 2 included a 30-minute refrigeration step. Therefore, the decrease in temperature from the start of freezing to -4° C., where latent heat evolution upon freezing occurs, was examined further. For condition 6, the rate of cooling was approximately -1° C./minute during this period. The rate of cooling for condition 2 was approximately -0.4° C./minute during the same timeframe. Therefore, condition 2 was selected for incorporation into a non-limiting cryopreservation process since slower rates of cooling are generally desired to maintain optimal cell viability.

Figure 2:
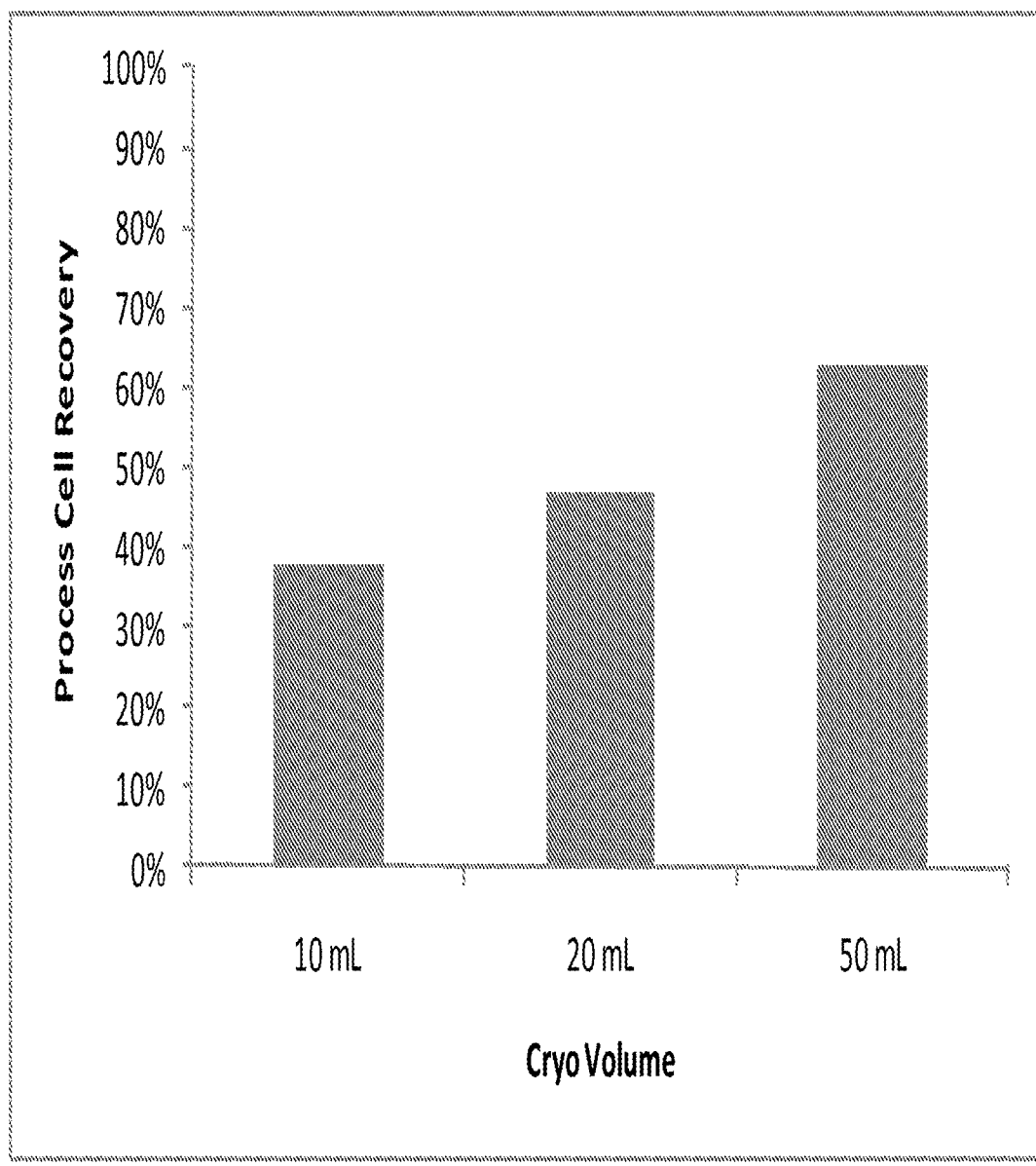
FIG. 2 depicts process cell recovery for amniotic membrane as a function of cryo volume.

FIG. 2 depicts the effects of cryopreservation solution volume on process (cryopreservation) cell recovery for the amniotic membrane. The analysis of the 10 mL cryopreservation solution volume involved 5 placenta lots, and the analysis of the 20 mL cryopreservation solution volume included 3 lots. For the 50 mL cryopreservation solution volume, 14 placenta lots were analyzed.

As depicted in FIG. 2, the 50 mL volume of cryopreservation solution volume provided superior cell recovery compared to that of the 10 ml and 20 ml. Since the 50 mL cryopreservation solution volume provided the slowest cooling rate, FIG. 2 indicates that a cooling rate of less than about 2° C./minute or less than about 1° C./minute can provide a superior method of manufacture according to the present invention.

FIG. 3 shows the results of a similar study of analysis of the cryopreservation cell recovery for the chorionic membrane, demonstrating that a cryopreservation solution volume of 50 mL was optimal. The analysis of the 10 mL cryopreservation solution volume involved 5 placenta lots, and the analysis of the 20 mL cryopreservation solution volume included 3 lots. For the 50 mL cryopreservation solution volume, 16 placenta lots were analyzed.

Experiments were conducted to evaluate different potential freezing conditions to maximize cell recovery after the cryopreservation process. FIG. 4 (cells from amniotic membrane) and FIG. 4 (cells from chorionic membranes) depict these results, showing the effects of refrigeration time and freezing parameters on process (cryopreservation) cell recovery for the chorionic membrane. Three conditions were analyzed. These conditions were also linked to the temperature mapping studies. The first condition involved directly freezing the product unit on a shelf within the freezer (-80° C.±5° C.). The second condition also contained a direct freeze, but the product unit was placed into a Styrofoam container within the freezer. The third condition included a refrigeration (2-8° C.) period of 30 minutes prior to the freezing step. For the amniotic membrane, 3 placenta lots were evaluated. Two (2) placenta lots were analyzed for the chorionic membrane. Results indicated that the third condition was optimal for both membrane types.

All of the cryopreservation parameters that were assessed for the amniotic and chorionic membranes are summarized in Table 3 and Table 4. The evaluation of the cell recoveries and cell viabilities from these experiments resulted in the selection of the final parameters for the manufacturing process. In addition, all average cell viability values were 70%.

TABLE 3

Post thaw cell count per cm², cell viability, and process (cryopreservation) cell recovery values for the amniotic membrane.

| Parameter | Condition Tested | Statistics | Cell Count per cm² | Cell Viability | Process Cell Recovery | Comments/ Conclusions |
|---|---|---|---|---|---|---|
| Refrigerate at 2-8° C. for 30-60 min and freeze at −80° C. ± 10° C. | All conditions | Average<br>SD<br>N | 55,709<br>45,210<br>32 | 83.4%<br>4.4%<br>32 | 64.2%<br>22.5%<br>32 | Overall assessment. |
| Refrigeration time interval | 30 min | Average<br>SD<br>N | 52,173<br>39,750<br>26 | 83.1%<br>4.5%<br>26 | 63.7%<br>21.4%<br>26 | No significant difference found in process cell recovery. A 30-60 min range was established. |
|  | 60 min | Average<br>SD<br>N | 71,033<br>66,525<br>6 | 85.0%<br>3.9%<br>6 | 66.5%<br>29.3%<br>6 |  |
| Thawing temperature | 37° C. ± 2° C. Water bath | Average<br>SD<br>N | 48,524<br>27,804<br>7 | 83.3%<br>1.7%<br>7 | 64.0%<br>34.4%<br>7 | No significant difference found in process cell recovery. The room temp condition was selected for logistical reasons. |
|  | Room temp water bath | Average<br>SD<br>N | 57,721<br>49,271<br>25 | 83.5%<br>4.9%<br>25 | 64.3%<br>19.0%<br>25 |  |
| Holding period after transfer into saline | 1-15 min | Average<br>SD<br>N | 50,873<br>38,969<br>26 | 83.1%<br>3.9%<br>26 | 65.0%<br>24.2%<br>26 | No significant difference found in process cell recovery. Membranes can be held in saline for up to 1 hr. |
|  | 1 hr | Average<br>SD<br>N | 76,667<br>66,565<br>6 | 85.1%<br>6.2%<br>6 | 61.0%<br>14.3%<br>6 |  |
| Tissue size | 5 cm × 5 cm | Average<br>SD<br>N | 58,431<br>47,603<br>28 | 83.3%<br>4.5%<br>28 | 62.8%<br>21.7%<br>28 | No decrease in process cell recovery from the 5 cm × 5 cm product to the 2 cm × 2 cm product. Both sizes were acceptable for use. |
|  | 2 cm × 2 cm | Average<br>SD<br>N | 36,656<br>13,175<br>4 | 84.4%<br>3.4%<br>4 | 73.9%<br>29.5%<br>4 |  |

TABLE 4

Post thaw cell count per cm², cell viability, and process (cryopreservation) cell recovery values for the chorionic membrane.

| Parameter | Condition Tested | Statistics | Cell Count per cm² | Cell Viability | Process Cell Recovery | Comments/ Conclusions |
|---|---|---|---|---|---|---|
| Refrigerate at 2-8° C. for 30-60 min and freeze at −80° C. ± 10° C. | All conditions | Average<br>SD<br>N | 23,217<br>9,155<br>27 | 87.3%<br>4.1%<br>27 | 102.8%<br>65.5%<br>27 |  |
| Dispase treatment | 30 min | Average<br>SD<br>N | 22,354<br>9,505<br>24 | 85.7%<br>5.1%<br>24 | 81.1%<br>32.4%<br>24 | No decrease in process cell recovery for the 45 min treatment. A 30-45 min range was established. |
|  | 45 min | Average<br>SD<br>N | 27,125<br>7,963<br>6 | 90.6%<br>2.2%<br>6 | 172.6%<br>101.2%<br>6 |  |

TABLE 4-continued

Post thaw cell count per cm², cell viability, and process (cryopreservation) cell recovery values for the chorionic membrane.

| Parameter | Condition Tested | Statistics | Cell Count per cm² | Cell Viability | Process Cell Recovery | |
|---|---|---|---|---|---|---|
| Refrigeration time interval | 30 min | Average | 23,815 | 86.8% | 102.2% | The process recovery value was >80% for the 60 min time interval. A 30-60 min range was established. |
| | | SD | 9,681 | 5.2% | 68.8% | |
| | | N | 25 | 25 | 25 | |
| | 60 min | Average | 20,773 | 85.8% | 84.9% | |
| | | SD | 7,356 | 4.7% | 14.4% | |
| | | N | 5 | 5 | 5 | |
| Thawing temperature | 37° C.± 2° C. water bath | Average | 33,360 | 85.9% | 114.7% | No significant difference found in process cell recovery. The room temp condition was selected for logistical reasons. |
| | | SD | 8,497 | 4.0% | 38.1% | |
| | | N | 5 | 5 | 5 | |
| | Room temp water bath | Average | 21,298 | 86.8% | 96.3% | |
| | | SD | 8,189 | 5.3% | 67.2% | |
| | | N | 25 | 25 | 25 | |
| Holding period after transfer into saline | 1-15 min | Average | 23,733 | 86.6% | 100.6% | No significant difference found in process cell recovery. Membranes can be held in saline for up to 1 hr. |
| | | SD | 9,674 | 5.1% | 67.0% | |
| | | N | 26 | 26 | 26 | |
| | 1 hr | Average | 20,550 | 87.0% | 91.4% | |
| | | SD | 6,575 | 4.8% | 32.0% | |
| | | N | 4 | 4 | 4 | |
| Tissue size | 5 cm × 5 cm | Average | 23,391 | 86.1% | 99.6% | No decrease in process cell recovery from the 5 cm × 5 cm product to the 2 cm × 2 cm product. Both sizes were acceptable for use. |
| | | SD | 8,865 | 5.0% | 58.7% | |
| | | N | 23 | 23 | 23 | |
| | 2 cm × 2 cm | Average | 23,036 | 88.4% | 98.7% | |
| | | SD | 11,362 | 5.0% | 81.3% | |
| | | N | 7 | 7 | 7 | |

Notes:
cm = centimeter; min = minutes; temp = temperature; hr = hour, SD = standard deviation; N = number.

These data indicate that a step of dispase treatment for about 30-45 mins provides a superior method of manufacture according to the present invention. These data also indicate that a step of refrigeration at 2-8° C. for 30-60 min before freezing provides a superior method of manufacture according to the present invention.

Example 8 Qualitative Evaluation of Cell Viability by Tissue Staining

The amniotic and chorionic membranes were stained using a LIVE/DEAD® Viability/Cytotoxicity kit (Molecular Probes Inc., Eugene, Oreg.) to qualitatively assess cell viability. Staining was performed as per the manufacturer's protocol. Membrane segments of approximately 0.5 cm×0.5 cm were used. Evaluation of stained membranes was performed using a fluorescent microscope. An intense uniform green fluorescence indicated the presence of live cells, and a bright red fluorescence indicated the presence of dead cells. Images of fresh amniotic and chorionic membranes as well as cryopreserved amniotic and chorionic membranes demonstrated that the manufacturing process did not alter the phenotypic characteristics of the membranes post thaw.

Figures 6A, 6B, 6C, 6D, 6E, 6F:
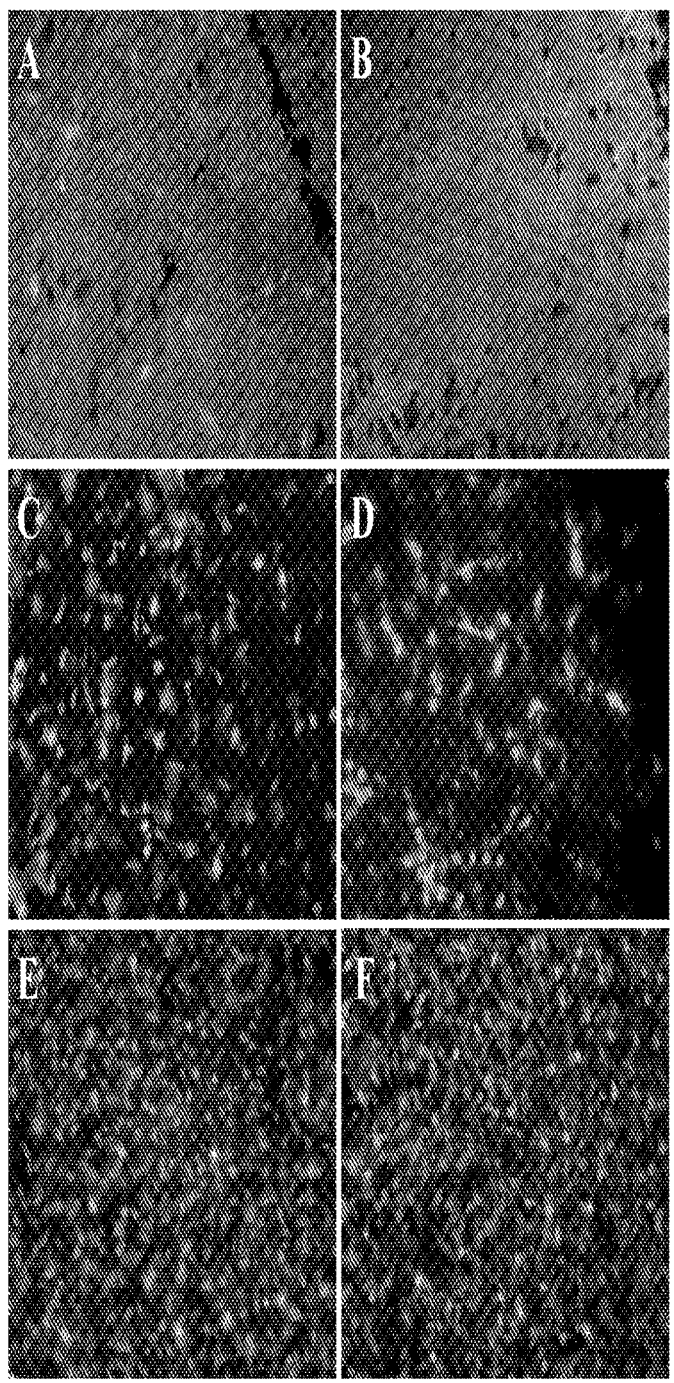
FIG. 6A-6F show representative images of the live/dead staining of the epithelial layer of fresh amniotic membrane. Representative images of the live/dead staining of the epithelial layer of fresh amniotic membrane (A); epithelial layer of cryopreserved amniotic membrane (B); stromal layer of fresh amniotic membrane (C); stromal layer of cryopreserved amniotic membrane (D); fresh chorionic membrane (E); and cryopreserved chorionic membrane (F). The bright staining is the live cells.

FIG. 6 contains representative images of fresh amniotic and chorionic membranes as well as cryopreserved amniotic and chorionic membranes. These images demonstrated that the manufacturing process did not alter the phenotypic characteristics of the membranes and the proportion of viable cell types (epithelial and stromal cells) in the membranes post thaw.

FIG. 6. Representative images of the live/dead staining of the epithelial layer of fresh amniotic membrane (A); epithelial layer of cryopreserved amniotic membrane (B); stromal layer of fresh amniotic membrane (C); stromal layer of cryopreserved amniotic membrane (D); fresh chorionic membrane (E); and cryopreserved chorionic membrane (F). Live cells are green, and dead cells are red.

Example 9 Placental Tissue Immunogenicity Testing

One unique feature of the human amnion and chorion is the absence of fetal blood vessels that prevent mobilization of leukocytes from fetal circulation. On the fetal side, macrophages resident in the chorioamniotic mesodermal layer represent the only population of immune cells. Thus, fetal macrophages present in the chorion and amnion are the major source of tissue immunogenicity. However, the number of macrophages in amnion is significantly lower (Magatti et al, Stem Cells, 2008, 26: 182), and this explains the low immunogenicity of amnion and the ability to use it across HLA barriers without matching between the donor and recipient (Akle et al, Lancet, 1981, 8254:1003; Ucakhan et al., Cornea, 2002, 21:169). In contrast, the chorion is considered immunogenic. In a study where the amnion was used together with the chorion for plastic repair of conjunctival defects, the success rate was low (De Roth Arch Ophthalmol, 1940, 23: 522). Without being bound by theory, the present inventors believe that removal of CD14+ cells from placental membranes eliminates activation of lymphocytes in vitro. In addition to the presence of fetal macrophages, the present inventors believe that immunogenicity of chorion can be mediated by contamination of blood cells coming from the maternal trophoblast, which contains blood vessels. Thus, the processing of placental membrane for clinical use can be enhanced by purification of the amnion and chorion from maternal trophoblasts and selective elimination of all CD14+ fetal macrophages.

Immunogenicity testing can be used to characterize a placental product as safe clinical therapeutics. For example, two bioassays can be used to test immunogenicity of manufactured placental products: Mixed Lymphocyte Reaction (MLR) and Lipopolysaccharide (LPS)-induced Tumor Necrosis Factor (TNF)-α secretion.

Example 10 Mixed Lymphocyte Reaction (MLR)

An MLR is a widely used in vitro assay to test cell and tissue immunogenicity. The assay is based on the ability of immune cells (responders) derived from one individual to recognize allogeneic Human Leukocyte Antigen (HLA) and other antigenic molecules expressed on the surface of allogeneic cells and tissues (stimulators) derived from another individual when mixed together in a well of an experimental tissue culture plate. The response of immune cells to stimulation by allogeneic cells and tissues can be measured using a variety of methods such as secretion of particular cytokines (e.g., Interleukin (IL)-2), expression of certain receptors (e.g., IL-2R), or cell proliferation, all of which are characteristics of activated immune cells.

Placental tissue samples representing different steps of the presently disclosed manufacturing process were used for immunogenicity testing. These samples included amnion with chorion and trophoblast as a starting material and separated choriotrophoblast, chorion, trophoblast, and amnion. Both freshly purified and cryopreserved (final products) tissues were tested.

For the MLR assay, cells from placental tissues were isolated using 280 U/mL of collagenase type II (Worthington, Cat No. 4202). Tissues were treated with enzyme for 60-90 min at 37° C.±2° C., and the resulting cell suspension was filtered through a 100 μm filter to remove tissue debris. Single cell suspensions were then centrifuged using a Beckman, TJ-6 at 2000 rpm for 10 min and washed twice with DPBS. Supernatant was discarded after each wash, and cells were resuspended in 2 mL of DMEM (Invitrogen, Cat No. 11885) and evaluated for cell number and cell viability by counting cells in the presence of Trypan blue dye (Invitrogen, Cat No. 15250-061). For the MLR, placental-derived cells were mixed with allogeneic hPBMCs at a 1:5 ratio in 24-well culture plates in DMEM supplemented with 5% fetal bovine serum (FBS) and incubated for 4 days in the incubator containing κ% $CO_2$, 95% humidity at 37° C.±2° C. Human Peripheral Blood Mononuclear Cells (hPBMCs) alone were used as a negative control, and a mixture of two sets of hPBMCs derived from two different donors was used as a positive MLR control. After 4 days of incubation, cells were collected from wells, lysed using a lysis buffer (Sigma, Cat No. C2978) supplemented with protease inhibitor cocktail (Roche, Cat No. 11836153001), and IL-2R□ was measured in cell lysates using the sIL-2R ELISA kit (R&D Systems, Cat No. SR2A00) according to the established protocol (G-SOP-Q088).

Figure 7:
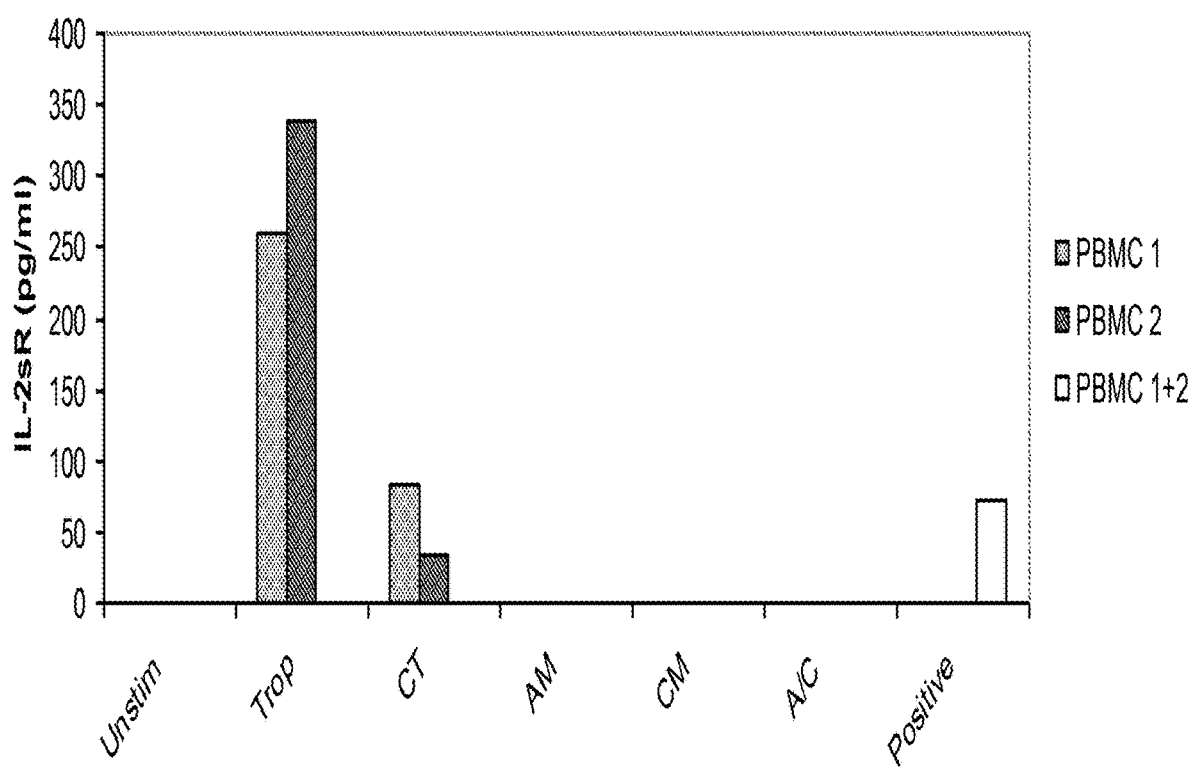
FIG. 7 depicts expression of IL-2sR from T-cells stimulated by placental derived cells from various membrane preparations.
Figure 8:
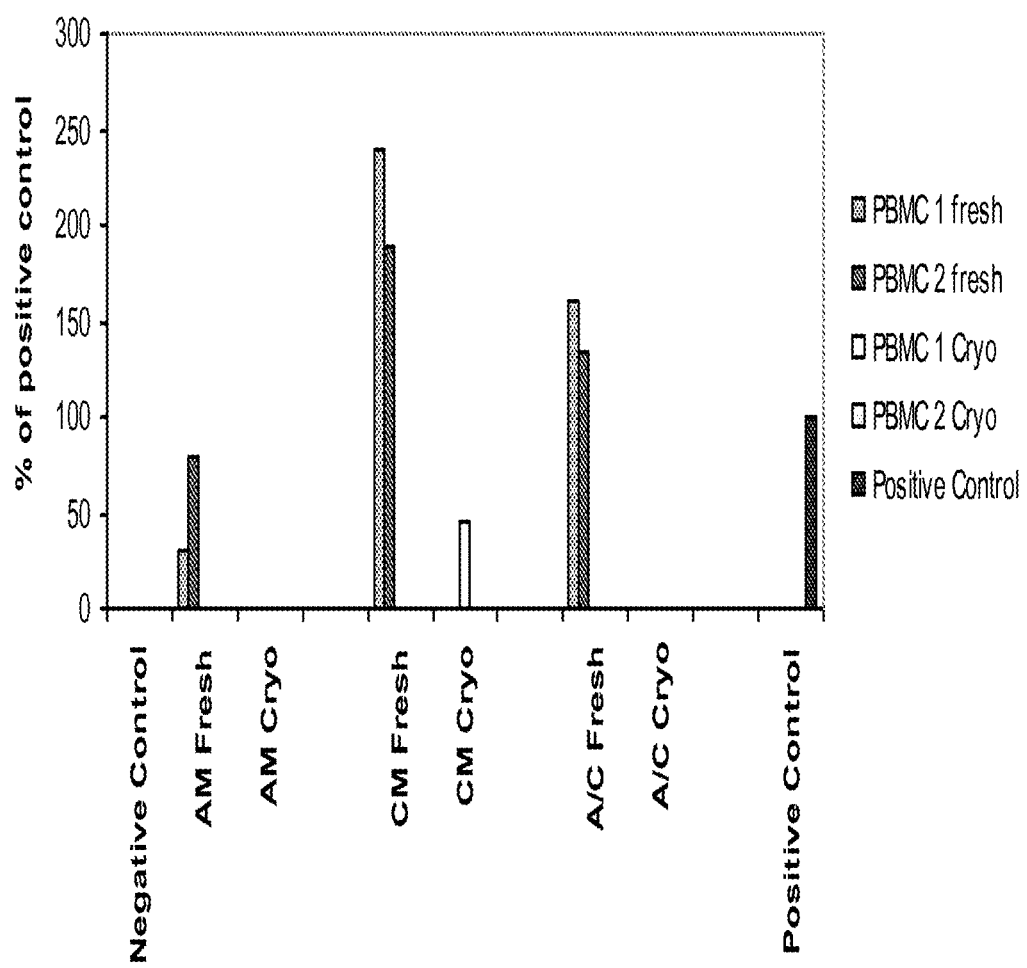
FIG. 8 depicts expression of IL-2sR from T-cells stimulated by placental derived cells from various membrane preparations after cryopreservation.

The level of IL-2R is a measure of activation of T-cells in response to immunogenic molecules expressed by allogeneic cells. Results of 2 out of 12 representative experiments are shown in FIG. 7 and FIG. 8. Results presented in these figures demonstrate a method of manufacture of placental membranes, resulting in low immunogenicity of the final products.

As depicted in FIG. 7: the manufacturing process serially reduces immunogenicity of the placental product. Samples representing different steps of the manufacturing process (Chorion+ Trophoblast (CT), Trophoblast (T), Amnion (AM), and Chorion (CM)) were co-cultured with hPBMCs for 4 days. IL-2αR was measured in cell lysates as a marker of T-cell activation. Negative control shows a basal level of immune cell activation: PBMCs derived from one donor were cultured alone. Positive control: a mixture of PBMCs derived from 2 different donors.

As depicted in FIG. 8, selective depletion of immunogenicity results from the present cryopreservation process of producing the present placental products, as evidenced by the significant decrease in immunogenicity upon cryopreservation.

Example 11 LPS-Induced TNF-α Secretion by Placental Membrane Cells

As described herein, fetal macrophages present in the amnion and chorion are a major source of tissue immunogenicity. Without being bound by theory, the present inventors believe that removal of CD14+ cells from placental membrane eliminates activation of lymphocytes and that depletion of allogeneic donor tissue macrophages decreases the level of inflammatory cytokine secretion and tissue immunogenicity. The inventors also believe that reduction of tissue immunogenicity can also be reached by depletion of TNF-α with anti-TNF-α antibodies or suppression of TNF-α secretion by IL-10. Macrophages in fetal placental membranes respond to bacteria by secretion of inflammatory cytokines. The secretion of TNF-α by fresh placental membranes in vitro in response to bacterial LPS is significantly higher in the chorionic membrane. Thus, the present inventors believe that immunogenicity of placental membranes is mediated by macrophages, the amount and/or activity of which is higher in the chorionic membrane.

According to the present invention, selective depletion of macrophages is an approach to selectively deplete immunogenicity of the amniotic and chorionic membranes, allowing the use of both allogeneic membranes for clinical applications. The assay of functional macrophages in a placental product is used here as an assay for immunogenicity testing (e.g. in production or prior to clinical use) based on the facts that: macrophages are the source of immunogenicity in chorionic membranes. Macrophages in placenta-derived membranes respond to bacterial LPS by secretion of high levels of TNF-α; and TNF-α is a critical cytokine involved in immune response and allograft tissue rejection. Therefore, secretion of TNF-α by placenta-derived membranes in response to LPS is used here to characterize tissue immunogenicity and for pre-use screening.

Example 12 Establishment of Allowed LPS-Induced TNF-α Secretion Level by Placental Membranes Data from published reports regarding the level of TNF-α, which is associated with the absence or an insignificant immune response in a variety of experimental systems, are presented in Table 5. These data indicate that a TNF-α level below 100 pg/mL correlates with a low immune response. The ability of amniotic and chorionic membranes to produce TNF-α spontaneously and in response to bacteria or bacterial LPS in vitro has been shown by a number of investigators.

Table 6 summarizes such data. The lowest spontaneous TNF-α secretion by amniotic membrane of about 70 pg/cm$^2$ of the membrane was reported by Fortunato et al. All reports also showed that fresh placental membranes secrete large amounts of TNF-α in response to bacteria or bacterial LPS, which is attributed to the presence of viable functional macrophages.

TABLE 5

TNF-α levels associated with no or an insignificant immune response.

| Description of experimental system | TNF-α levels associated with the absence/reduction of immune response | Comments | References |
|---|---|---|---|
| IL-10-induced inhibition of MLR in vitro. TNF was measured in tissue culture supernatant by ELISA. | Mean 260 pg/mL | | Wang et al., Transplantation, 2002, 74: 772 |
| MLR using skin tissue explants (0.02 cm2 per well) as stimulators in the presence or absence of IL-10 (skin explant assay). Skin tissue destruction was assessed microscopically, and severity was assigned based on histopathological tissue damage. | Mean 100 pg/mL | | |
| Endogeneous TNF production in MLR in the presence or absence of anti-TNF antibodies. TNF levels were assessed using the WEHI-164 cytotoxicity assay. | ~0.04 U/mL for the negative control and MLR in the presence of anti-TNF antibodies, which correlated with no or significant inhibition of lymphocyte proliferation | TNF activity per mg is not provided. | Shalaby et al, J Immunol, 1988, 141: 499 |
| TNF levels in BAL fluid of lung isografts, unmodified allograft, and alveolar macrophages (AM) depleted allograft in rats. | Isograft: below detection; AM-depleted allograft: ~15 pg/mL of BAL (total 75 pg/5 ml of BAL) | Unmodified allograft: ~45 pg/mL (immunogenic) | Sekine et al, J Immunol, 1997, 159: 4084. |
| TNF levels in MLR after 48 hours in the presence or absence of advanced glycation end products (MLR inhibitors). | ~<200 pg/mL TNF correlated with a complete inhibition of MLR | | Ohashi et al, Clin Immunol, 2009, e-pub ahead of print |
| TNF levels in MLR. | <100 pg/mL TNF in MLR with HLA-matched donors (control, no stimulation) | | Toungouz et al, Hum Immunol, 1993, 38: 221 |
| TNF activity in MLR when pieces of cryopreserved skin allografts (~0.2 cm$^2$) were incubated with hPBMCs for 24 hours. Positive control: hPBMC + LPS; negative - hPBMC alone. | Negative control ~20 U of TNF activity; MLR with skin explants - 0-40 U; Positive control - 600 U | Unit of activity was calculated as TNF in ng/mL divided by OD at 570 nm for the same experimental well | Lomas et al, Cell Tissue Bank, 2004, 5: 23. |
| Cytokine time course in MLR, including TNF. | | Optimal TNF after 24 hours - ~150 pg/mL | Jordan & Ritter, J Immunol Meth, 2002, 260: 1 |

TABLE 5-continued

TNF-α levels associated with no or an insignificant immune response.

| Description of experimental system | TNF-α levels associated with the absence/reduction of immune response | Comments | References |
|---|---|---|---|
| MLR using skin tissue explants (0.02 cm$^2$ per well) as stimulators in the presence or absence of anti-TNF antibodies (skin explant assay). Skin tissue destruction was assessed microscopically, and severity was assigned based on histopathological tissue damage. | For no skin destruction: 0.5-1.1 pg/mL for HLA compatible responders, and 2.6-1376 pg/mL for unmatched MLR | Recalculation per 1 cm$^2$ of skin tissue: lowest TNF non-immunogenic level is 100 pg/cm$^2$ | Dickinson et al, Cytokine, 1994, 6: 141 |

TABLE 6

Secretion of TNF in vitro by fresh amniotic and chorionic membranes.

| Description of experimental system | TNF levels secreted by fresh placental membranes in culture | Comments/ recalculations of the lowest TNF levels per cm$^2$ | References |
|---|---|---|---|
| TNF secretion by "fresh" amnion and chorion tissues (1.44 cm$^2$) incubated for 24 hours in the presence or absence of LPS (500 ng/mL). | Chorion: basal 3.3 ± 0.46 ng/cm$^2$, LPS-induced - 150-250 ng/cm$^2$ Amnion: basal 2.5 ± 1.3 ng/cm$^2$, LPS-induced - ~50 ng/cm2 | Lowest TNF level for amnion is 1200 pg/cm$^2$ | Zaga et al., Biol Reprod, 2004, 71: 1296 |
| TNF secretion by "fresh" amnion and chorion tissues (1.8 cm diameter disks: 2.5 cm$^2$) incubated for 24 hours in the presence or absence of E. Coli in 1 mL medium. | Basal ~1-2.5 pg/μg total protein in the medium for both amnion and chorion; E. Coli-induced: amnion - 29.2 (14.5-35.3) pg and chorion - 53.15 (40-94.2) pg per μg total protein | Lowest TNF level for amnion is 800 pg/cm$^2$ | Zaga-Clavellina et al, Reprod Biol Endocrinol, 2007, 5: 46 |
| TNF secretion by "fresh" amnion and chorion tissues (chorion 8-10 mg tissue/mL; amnion 5-7 mg/mL, 0.02-0.04 cm$^2$) incubated for 20 hours in the presence or absence of LPS (5 μg/mL). | Basal: ~2-64 U/mL or 8-10 mg chorion; <1 U/mL for 5-7 mg amnion. LPS-induced: >100 U/10 mg for chorion and ~15-17 U/10 mg for amnion | 1 unit = ~100-200 pg/mL; Lowest TNF level for amnion is <100 pg/mL corresponding to <2500 pg/cm$^2$ | Paradowska et al, Placenta, 1997, 18: 441 |
| TNF secretion by "fresh" amnion (0.57 cm$^2$) in 0.8 mL incubated for 24 hours in the presence or absence of LPS (50 ng/mL). | Amnion: Basal - 40 pg/mL, LPS-induced - 410 pg/mL | Lowest TNF level for fresh amnion is ~70 pg/cm$^2$ | Fortunato et al, Am J Obstet Gynecol, 1996, 174: 1855 |
| TNF secretion by "fresh" amnion and chorion tissues (4 cm$^2$) incubated for 24 hours in the presence or absence of LPS (1-1000 ng/mL) | Basal: Amnion ~7-13 ng/mL/g tissue); Chorion ~18 ng/mL/g tissue LPS-induced (1000 ng/mL): Amnion ~14 ng/mL/g), Chorion ~27 ng/mL/g | Amnion is 5-7 mg corresponds ~0.02-0.04 cm$^2$; 1 g is ~6 cm$^2$; Lowest TNF level for amnion is ~1000 pg/cm$^2$ | Thiex et al, Reprod Biol Endocrinol, 2009, 7: 117 |

Example 13 LPS-Induced TNF-α Secretion and CT Induced MLR Immunogenicity Assay cm×2 cm pieces of placental membranes representing intermediates and final products were placed in tissue culture medium and exposed to bacterial LPS (1 µg/mL) for 20-24 hr. After 24 hours, tissue culture supernatant were collected and tested for the presence of TNF-α using a TNF-α ELISA kit (R&D Systems) according to the manufacturer's protocol. Human hPBMCs (SeraCare) known to contain monocytes responding to LPS by secretion of high levels of TNF-α were used as a positive control in the assay. hPBMCs and placental tissues without LPS were also included as controls in the analysis. In this assay, TNF detected in the culture medium from greater than 70 pg/cm$^2$ (corresponding to 280 pg/mL) for both spontaneous and LPS-induced TNF-α secretion was considered immunogenic.

Figure 9A:
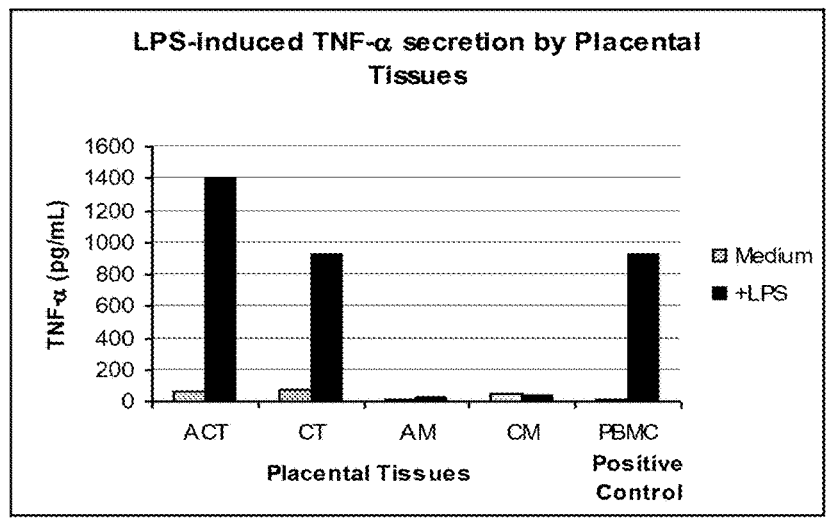
FIG. 9A-B depict LPS stimulated TNF α released from various membrane preparations.
Figure 9B:
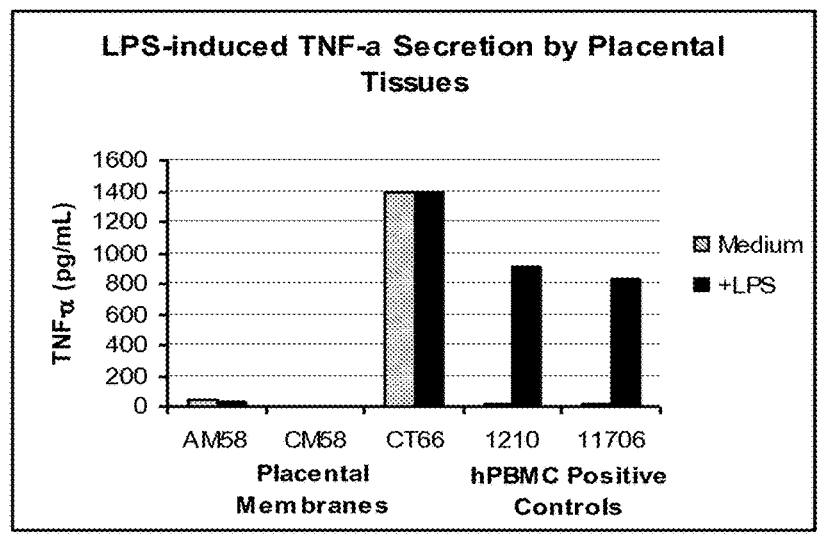

As depicted in FIG. 9A and FIG. 9B, the manufacturing process serially reduces immunogenicity of the placental product. Samples representing different steps of the manufacturing process (Amnion+Chorion+Trophoblast (ACT), Chorion+Trophoblast (CT), Amnion (AM), and Chorion (CM)) were incubated in the presence of LPS for 24 hr, and after that tissue culture supernatants were tested for the TNF-α by ELISA. Tissues cultured in medium without LPS show the basal level of TNF α secretion. PBMCs, which are known to secrete high levels of TNF, were used as a positive control.

The low levels of TNF-α and the absence of the response to LPS by AM and CM indicates the absence of viable functional macrophages that are the major source of immunogenicity for amniotic and chorionic membranes. Results of this assay showed a correlation with the MLR data: tissues that produce high levels of TNF-α in response to LPS are immunogenic in the MLR assay FIG. 9A and FIG. 9B, for TNF-α secretion; FIG. 9, C-MLR).

As depicted in FIG. 9A and FIG. 9B, the manufacturing process serially reduces immunogenicity of the placental product. Samples representing different steps of the manufacturing process (Amnion+Chorion+Trophoblast (ACT), Chorion+Trophoblast (CT), Amnion (AM), and Chorion (CM)) were incubated in the presence of LPS for 24 hr, and after that tissue culture supernatants were tested for the TNF-α by ELISA. Tissues cultured in medium without LPS show the basal level of TNF a secretion. PBMCs, which are known to secrete high levels of TNF, were used as a positive control.

Choriotrophoblast (CT), which secreted high levels of TNF-α (FIG. 9B), was tested in MLR against two different PBMC donors. CT cells were co-cultured with PBMCs for 4 days. IL-2αR was measured in cell lysates as a marker of T-cell activation. Positive control: a mixture of PBMCs derived from 2 different donors.

Figure 9C:
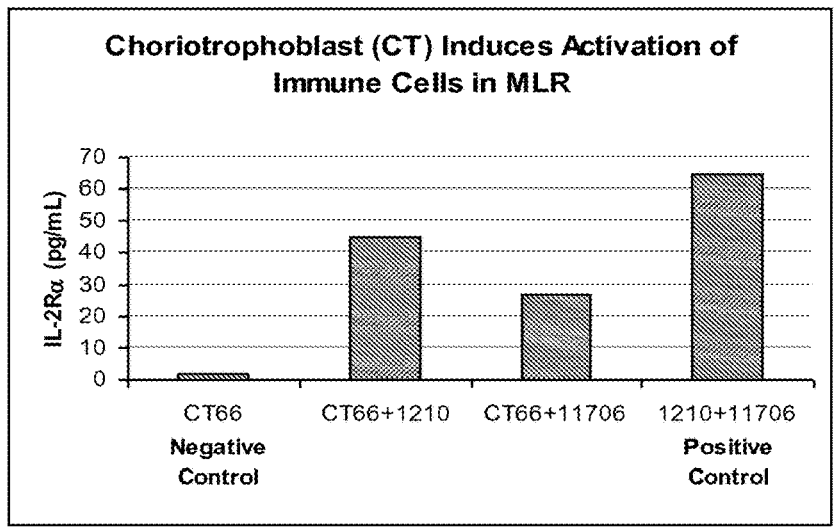
FIG. 9C shows that preparations producing high levels of TNF α are immunogenic as tested in MLR against two different PBMC donors. IL-2αR was measured in cell lysates as a marker of T-cell activation. Positive control; a mixture of PBMCs derived from 2 different donors.

FIG. 9C shows that preparations producing high levels of TNF-α are immunogenic. Choriotrophoblast (CT), which secreted high levels of TNF-α (FIG. 9B), was tested in MLR against two different PBMC donors. CT cells were co-cultured with PBMCs for 4 days. IL-2αR was measured in cell lysates as a marker of T-cell activation. Positive control: a mixture of PBMCs derived from 2 different donors.

Example 14 Analysis of Placental Cells by FACS

Knowing the cellular composition of amnion and chorionic membranes is important for developing a thorough understanding of potential functional roles in wound healing and immunogenicity. Previous reports demonstrated that both amnion and chorion contains multiple cell types. Purified amnion has two major cellular layers: epithelial cells and stromal. In addition to epithelial cells and fibroblasts, stromal cells were identified in the amnion and chorion. Although there are no fetal blood vessels within either the amniotic or chorionic membranes, both membranes comprise resident fetal macrophages. The close proximity to maternal blood circulation and decidua provide a potential source of immunogenic cells (maternal leukocytes and trophoblast cells) and therefore are a potential source of immunogenicity. To investigate the cellular composition of the amnion and chorion, FACS analysis was performed.

Example 14.1 FACS Procedure: Single Cell Suspension Preparation

Purified amnion and chorionic membranes were used for cellular phenotypic analysis via FACS. Cells from amnion and chorion were isolated using 280 U/mL collagenase type II (Worthington, Cat No. 4202). Tissues were treated with enzyme for 60-90 min at 37° C.±2° C., and the resulting cell suspension was filtered through a 100 µm filter to remove tissue debris. Single cell suspensions were then centrifuged using a Beckman TJ-6 at 2000 rpm for 10 min and washed twice with DPBS. Supernatant was discarded after each wash, and cells were resuspended in 2 mL of FACS staining buffer (DPBS+0.09% NaN$_3$+1% FBS).

Example 14.2 Immunolabeling Cells for Specific Cellular Markers

Once the single cell suspension was prepared according to Example 10, a minimum of 1×10$^5$ cells in 100 µL of FACS staining buffer was treated with antibodies labeled with fluorescent dye. Table 7 provides descriptions of the antibodies and the amounts used. For cell surface markers, cells were incubated for 30 min at room temperature in the dark with antibodies followed by washing twice with FACS staining buffer by centrifugation at 1300 rpm for 5 min using a Beckman TJ-6 centrifuge. Cells were then resuspended in 400 µL of FACS staining buffer and analyzed using a BD FACSCalibur flow cytometer. To assess cell viability, 10 µL of 7-AAD regent (BD, Cat No. 559925) was added just after the initial FACS analysis and analyzed again. For intracellular staining, cells were permeabilized and labeled following the manufacturer's recommendations (BD Cytofix/Cytoperm, Cat No. 554714) and analyzed using a BD FACSCalibur flow cytometer.

TABLE 7

Description of reagents used for placental cell characterization by FACS.

| Cell marker antibody and label type | Cat No. | Volume of antibody solution used | Cell marker type | Cell marker specificity |
|---|---|---|---|---|
| IgG1 isotype-PE | BD 559320 | 5 µL | Cell surface | Isotype control |
| CD105-PE | Caltag MHCD10504 | 20 µL | Cell surface | MSC marker |
| CD166-PE | BD 559263 | 80 µL | Cell surface | MSC marker |
| CD45-PE | BD 555483 | 10 µL | Cell surface | Hematopoetic cell marker |

TABLE 7-continued

Description of reagents used for placental cell characterization by FACS.

| Cell marker antibody and label type | Cat No. | Volume of antibody solution used | Cell marker type | Cell marker specificity |
|---|---|---|---|---|
| IgG2a isotype-PE | BD 555574 | 2 μL | Cell surface | Isotype control |
| CD14-PE | BD 555398 | 20 μL | Cell surface | Monocyte marker |
| HLA-DR-PE | BD 556644 | 20 μL | Cell surface | HLA class II specific for antigen-presenting cells |
| IgG1 isotype-FITC | BD555748 | 5 μL | Cell surface | Isotype control |
| CD86-FITC | BD 557343 | 20 μL | Cell surface | Immune co-stimulatory marker |
| CD40-FITC | BD 556624 | 20 μL | Cell surface | Immune co-stimulatory marker |
| IgG1 isotype-unlabeled | Dako X0931 | 10 μL | Intracellular | Isotype control |
| Cytokeratin 7-unlabeled | Dako M7018 | 2 μL | Intracellular | Trophoblast marker |
| Rabbit anti-mouse FITC | Dako F0261 | 5 μL | Intracellular | Secondary antibody |

TABLE 8

Characterization of the cellular composition of placental membranes based on selective CD markers.

| | Marker | Amnion (% range) | Chorion (% range) |
|---|---|---|---|
| MSC Markers | CD105 | 72.1-88.2 | 6.4-78.5 |
| | CD166 | 17.3-58.0 | 4.8-51.5 |
| Hematopoietic Cell Markers | CD14 | 6.93-10.5 | 0.9-6.1 |
| | CD45 | 4.4-9.9 | 4.6-14.7 |
| Immune co-stimulatory markers | HLA-DR | 0-5.6 | 0-14.7 |
| | CD86 | 24.3-49.6 | 4.9-22.5 |
| | CD40 | 7.0-68.7 | 2-5.8 |
| Trophoblast marker | Cytokeratin-7 | 1.36-4.66 | 2.71-23.07 |

TABLE 9

FACS analysis of cultured cells (passage 0) from placenta lot D16.

| Cell Surface Marker | Amnion (%) | Chorion (%) |
|---|---|---|
| CD45 | 2.18 | 0.53 |
| CD166 | 92.77 | 82.62 |
| CD105 | 83.02 | 86.73 |
| CD49a | 92.28 | 92.26 |
| CD73 | 89.57 | 94.57 |
| CD41a | −0.03 | −0.05 |
| CD34 | −0.23 | −0.25 |
| HLA-DR | −0.23 | −0.19 |
| CD19 | −0.19 | −0.22 |
| CD14 | −0.25 | −0.27 |
| CD90 | 99.12 | 98.00 |

Example 15 Phenotypic Analysis of Placental Cells

FACS analysis of single cell suspensions of both amnion and chorion membranes demonstrates that both membranes contain cells expressing markers specific for mesenchymal stem cells (refer to Table 8), implicating the presence of MSCs. In addition, several immunogenic markers, which are more likely expressed on CD14+ placental macrophages, were detected. The % ranges for different markers are wide. It can be explained by: 1) high variability in cell number between placenta donors; and 2) technical issues, which include the presence of high and variable cellular and tissue debris in the cellular suspension. Although debris can be gated out, debris particles that are comparable with cells by size will affect the accuracy of the calculated % for each tested marker. In addition, Table 9 provides a FACS analysis of cells isolated from the amniotic and chorionic membranes that were cultured in 10% FBS in DMEM at 37° C.±2° C. until confluency (passage 0 cells).

These data demonstrated that cells derived from amniotic and chorionic membranes retained a phenotype similar to MSCs after culturing. In conclusion, the presence of stromal cells in placental tissues was confirmed by FACS analysis.

As certain methods of manufacture are taught herein to retain amniotic membrane cells, these data indicate that the present methods can produce placental products that comprise a amniotic membrane containing MSC-like cells that express CD105, CD166, C90, and/or CD73 (also referred to herein as AMSCs or MSCs).

Example 16 Adherence of Cells Derived from Placental Products

Therapeutic cells, in optional embodiment of the present invention, are adherent, express specific cellular markers such as CD105 and lack expression of other markers such as CD45, and demonstrate the ability to differentiate into adipocytes, osteoblasts, and The expression of specific cellular markers has already been described in Example 15. To determine if the cells within the placental product derived from the chorionic membrane can adhere to plastic and differentiate into one of the lineages, cells were isolated from the placental product derived from the amnion as described in this invention and cultured at 37° C.±2° C. and expanded.

Figure 10A:
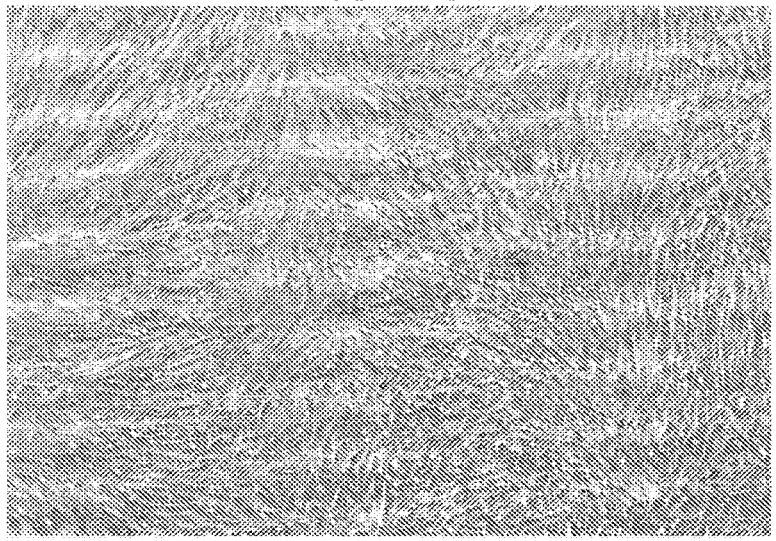
FIG. 10A-C shows images of cultured cells isolated from various membrane preparations.
Figure 10B:
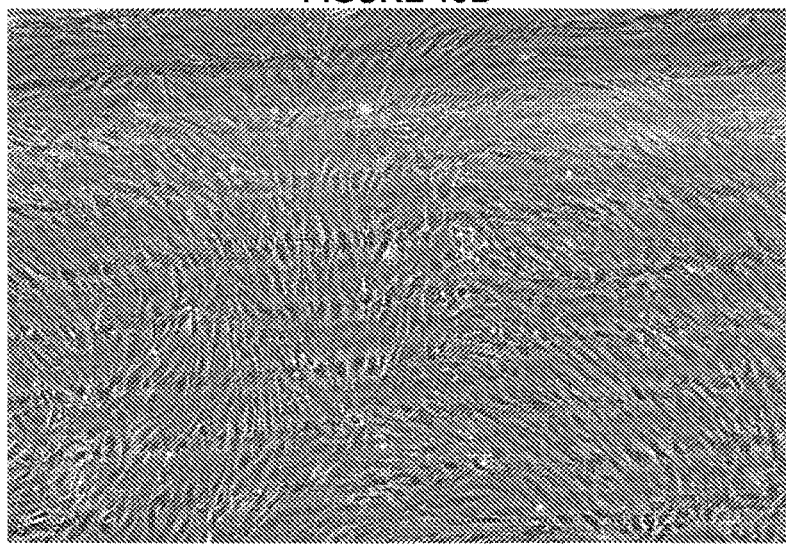
Figure 10C:
Figure 11:
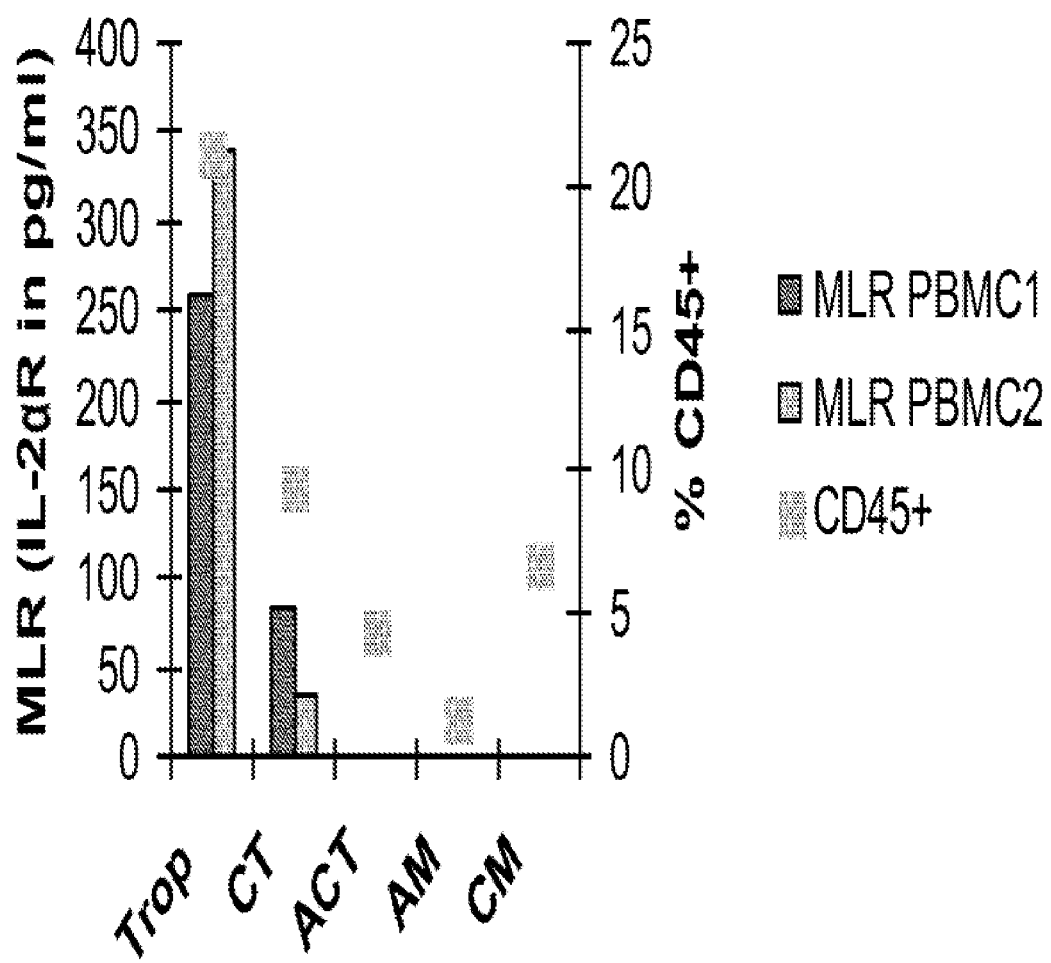
FIG. 11 depicts a correlation between IL-2sR release in an MLR assay of various membrane preparations and the number of CD45+ cells.

FIG. 10 shows representative images of cells isolated and cultured from amniotic (FIG. 10.A) and chorionic (FIG. 10.B) membranes demonstrating plastic adherence, which is a key feature of MSCs. As a comparison, a representative image of MSCs isolated and expanded from human bone marrow aspirate is also provided (FIG. 10.C). Together, these data show that cells derived from amniotic and chorionic membranes retain a phenotype similar to MSCs after culturing as demonstrated by the cellular markers present in addition to the ability of the cells to adhere to plastic. In conclusion, the presence of MSCs in placental tissues was confirmed by FACS analysis and tissue culture Example 17 Live CD45+ FACS Analysis As CD45 is a general marker for hematopoietic cells and therefore a marker for the presence immunogenic cells, the presence of CD45+ cells may correlate well with how immunogenic a tissue may be. An initial study indeed showed a correlation between amount of immunogenicity as measured via an in vitro MLR assay of placental tissue at various stages within the manufacturing process (as described previously), and the amount of CD45+ cells was determined via FACS analysis. As FIG. 11 demonstrates, membranes that trigger the expression of high levels of IL-2sR on hPBMC responders in MLR also contained a high percentage of CD45+ cells, indicating that immunogenicity of placental membranes can be correlated with the number of CD45+ cells. Further studies revealed, however, that quantifying CD45+ cells via FACS alone showed high variability that did not allow for the establishment of a safety threshold for CD45+ cells in placental membranes. Accordingly, the inventors evaluated whether or not viability of CD45+ cells is correlated with immunogenicity.

Figure 12:
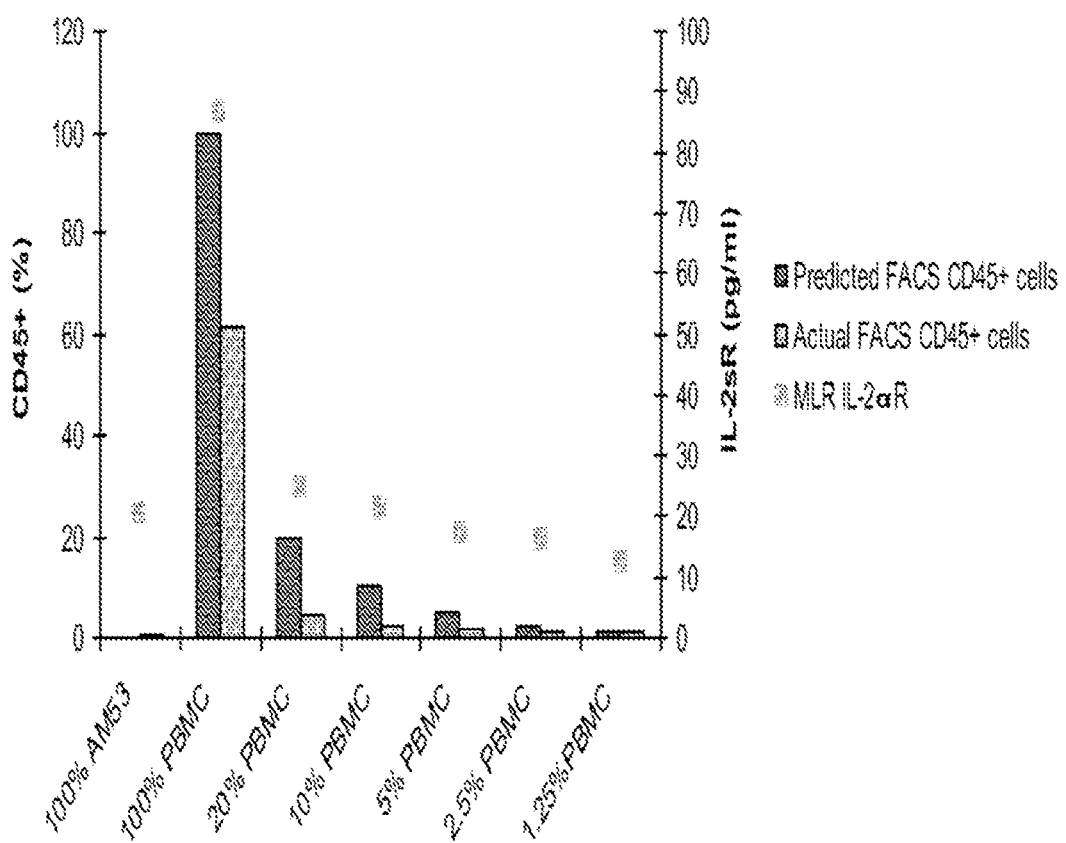
FIG. 12 depicts the IL-2sR release in an MLR assay of amniotic membrane preparations and the number of CD45+ cells.

To eliminate some of the variability in CD45+ measurements via FACS, viability of CD45+ cells was assessed, as dead CD45+ cells do not contribute to immunogenicity. To ensure an accurate assessment of live CD45+ cells, a pilot experiment was conducted in which a single cell suspension of amnion membrane was spiked in with a known concentration of live CD45+ cells (hPBMCs) ranging from a theoretical 1.25% to 20% (0.75-12%—actual % of the spiked cells) of the total cell concentration in suspension. Cells were stained with CD45-PE antibody at determined concentrations (refer to Table 10), incubated with 7-AAD cell viability test reagent, and analyzed using a BD FACSCalibur. Table 10 demonstrates that recovery of known amounts of CD45+ cells was not correct (4th column in the table). For example, although 12% of PBMCs was spiked into a single-cell suspension of amnion membrane, only 4.26% of CD45+ cells were recovered according to FACS analysis (>60% difference from the actual spike). To correlate with immunogenicity, MLR was also performed in parallel. Briefly, single cell suspensions of amniotic membrane spiked with various amounts of live hPBMCs were co-cultured with another donor of PBMCs in the MLR. FIG. 12 depicts a correlation between the amount of CD45+ cells present in amnion-derived cell suspensions and immunogenicity in MLR in vitro. Table 10 and FIG. 12 show that the suspensions spiked with higher amounts of live CD45+ cells resulted in higher immunogenicity as measured by IL-2sR expression on the hPBMC responder donor.

TABLE 10

% CD45+ recovery experiments.

| Sample Description (in % of cell types in the mixture) | % CD45+ cells (detected by FACS) | Actual spike (%, based on 60% CD45+ cells in this hPBMC batch) | % Difference from actual spike | Cell suspension immunogenicity (tested in MLR and expressed as IL-2R in pg/mL) |
|---|---|---|---|---|
| 100% amnion | 0.65 | N/A | N/A | 20.23 |
| 0% PBMC | N/A | N/A | N/A | 15.6 (negative control) |
| 100% PBMC | 61.51 | N/A | N/A | 86.31 (positive control) |
| 20% PBMC + 80% Amnion | 4.26 | 12 | 64.5% | 24.38 |
| 10% PBMC + 90% Amnion | 2.24 | 6 | 62.7% | 21.17 |
| 5% PBMC + 95% Amnion | 1.7 | 3 | 43.3% | 16.75 |
| 2.5% PBMC + 97.5% Amnion | 1.36 | 1.5 | Not calculated* | 15.9 |
| 1.25% PBMC + 98.75% Amnion | 1.06 | 0.75 | Not calculated* | 12.27 |

Notes:
N/A—not applicable;
*Not calculated—values are close to the method detection limits Example 18 Protein Array Analyses The protein profiles of amniotic and chorionic membranes were investigated using a SearchLight Multiplex chemiluminescent array. The presence of proteins in tissue membrane extracts and secreted by tissues in culture medium was investigated. For comparison, two commercially available products containing living cells, Apligraf and Dermagraft, were assayed.

Example 18.1. Dermagraft

Dermagraft membrane was thawed and washed according to the manufacturer's instructions. Dermagraft membrane was cut into 7.5 cm² pieces. For tissue lysates, one 7.5 cm² piece of membrane was snap frozen in liquid nitrogen followed by pulverization using a mortar and pestle. Crushed tissue was transferred to a 1.5 mL microcentrifuge tube and 500 µL of Lysis buffer (Cell Signaling Technologies, Cat No. 9803) with protease inhibitor (Roche, Cat No. 11836153001) was added and incubated on ice for 30 min with frequent vortexing. The sample was then centrifuged at 16000 g for 10 min. The supernatant was collected and sent for protein array analysis by Aushon Biosystems. For tissue culture, one 7.5 cm² piece of membrane was plated onto a well of a 12-well dish and 2 mL of DMEM+1% HSA+ antibiotic/antimycotic were added and incubated at 37° C.±2° C. for 3, 7, or 14 days. After incubation, tissue and culture media were transferred to a 15 mL conical tube and centrifuged at 2000 rpm for 5 min. Culture supernatant was collected and sent for protein array analysis by Aushon Biosystems.

Example 18.2 Apligraf

Apligraf membrane was cut into 7.3 cm² pieces. For tissue lysates, one 7.3 cm² piece of membrane was snap frozen in liquid nitrogen followed by pulverization using a mortar and pestle. Crushed tissue was transferred to a 1.5 mL microcentrifuge tube and 500 µL of Lysis buffer (Cell Signaling Technologies, Cat No. 9803) with protease inhibitor (Roche, Cat No. 11836153001) was added and incubated on ice for 30 min with frequent vortexing. The sample was then centrifuged at 16000 g for 10 min. The supernatant was collected and sent for protein array analysis by Aushon Biosystems. For tissue culture, one 7.3 $cm^2$ piece of membrane was plated onto a well of a 12-well dish and 2 mL of DMEM+1% HSA+ antibiotic/antimycotic were added and incubated at 37° C.±2° C. for 3, 7, or 14 days. After incubation, tissue and culture media were transferred to a 15 mL conical tube and centrifuged at 2000 rpm for 5 min. Culture supernatant was collected and sent for protein array analysis by Aushon Biosystems.

Example 18.3 Amniotic and Chorionic Membranes

Amniotic and chorionic membranes were isolated and packaged at −80° C.±5° C. according to the manufacturing protocols disclosed herein in Example 3. Packaged membranes were then thawed in a 37° C.±2° C. water bath and washed 3 times with DPBS. Membranes were cut into 8 $cm^2$ pieces. For tissue lysates, one 8 $cm^2$ piece of membrane was snap frozen in liquid nitrogen followed by pulverization using a mortar and pestle. Crushed tissue was transferred to a 1.5 mL microcentrifuge tube and 500 µL of Lysis buffer (Cell Signaling Technologies, Cat No. 9803) with protease inhibitor (Roche, Cat No. 11836153001) was added and incubated on ice for 30 min with frequent vortexing. Tissue lysate was then centrifuged at 16000 g for 10 min. The supernatant was collected and sent for protein array analysis by Aushon Biosystems. For tissue culture, one 8 $cm^2$ piece of membrane was plated onto a well of a 12-well dish and 2 mL of DMEM+1% HSA+ antibiotic/antimycotic were added and incubated at 37° C.±2° C. for 3, 7, or 14 days. After incubation, tissue and culture media were transferred to a 15 mL conical tube and centrifuged at 2000 rpm for 5 min. Culture supernatant was collected and sent for protein array analysis by Aushon Biosystems.

Initial testing consisted of an analysis of 36 proteins that are important for wound healing. The list of identified proteins is described in Table 11.

TABLE 11

List of selected proteins for analysis.

| Protein Group Based on Functionality | | Comments |
| --- | --- | --- |
| Metalloproteases | Matrix Metalloproteinase 1 (MMP1), MMP2, 3, 7, 8, 9, 10, 13 | Matrix and growth factor degradation; facilitate cell migration. |
| MMP Inhibitors | Tissue Inhibitors of MMPs (TIMP1 and 2) | Have angiogenic activity; can be placed in the "angiogenic factors" group. |
| Angiogenic Factors | Angiotensin-2 (Ang-2); basic Fibroblast Growth Factor basic (bFGF); heparin-bound Epidermal Growth Factor (HB-EGF); EGF; FGF-7 (also known as Keratinocyte Growth Factor-KGF); Platelet derived Growth Factors (PDGF) AA, AB, and BB; Vascular Endothelial Growth Factor (VEGF), VEGF-C and VEGF-D; Neutrophil gelatinase-associated lipocalin (NGAL); Hepatocyte Growth Factor (HGF); Placenta Growth Factor (PlGF); Pigment Epithelium Derived Factor (PEGF); Thrombopoetin (TPO) | Majority of these factors also have growth and migration stimulatory activities and can be placed in a group of growth factors. |
| Protease Inhibitor/Protein Carrier | Alpha-2-macroglobulin | Inhibit protease activity; regulate growth factor activity. |
| Growth Factors | See "angiogenic factors" + Transforming Growth Factor alpha (TGF-a) | See "angiogenic factors." |
| Cytokines | Adiponectin (Acrp-30) | Affect keratinocyte functions. |
| | Granulocyte Colony-Stimulating Factor (G-CSF) | Protection from infections. |
| | Interleukin1 Receptor Antagonist (IL-1RA) | Regulate activity of inflammatory cytokine IL-1. |
| | Leukemia Inhibitory Factor (LIF) | Support angiogenic growth factors. |
| Chemokines | SDF-1beta | Attracts endothelial and other stem cells from circulation to wound site. |
| Regulators of IGF | Insulin-like growth factor binding protein (IGFBP1, 2, 3) | Regulate IGF activity. |

Example 18. Protein Expression in Present Placental Products

Figure 13A:
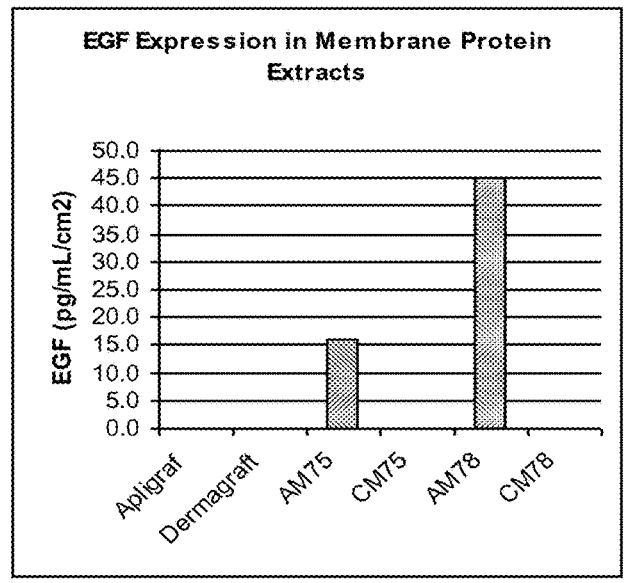
FIG. 13A-C depict expression of EGF (FIG. 13A), IGFBP1 (FIG. 13B), and Adiponectin (FIG. 13C) in amniotic and/or chorionic membranes.
Figure 13B:
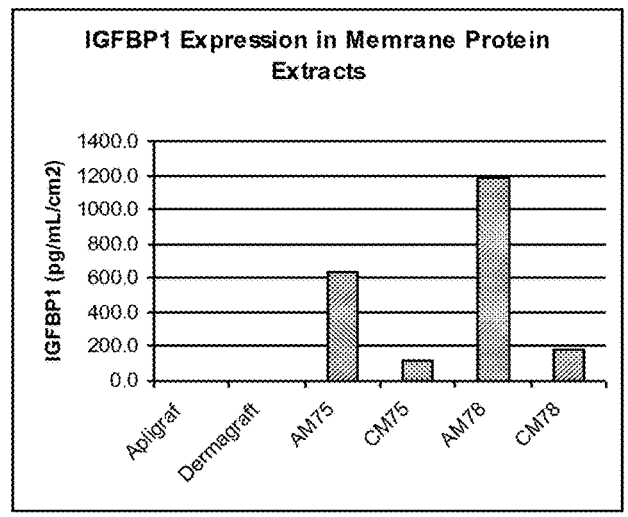
Figure 13C:
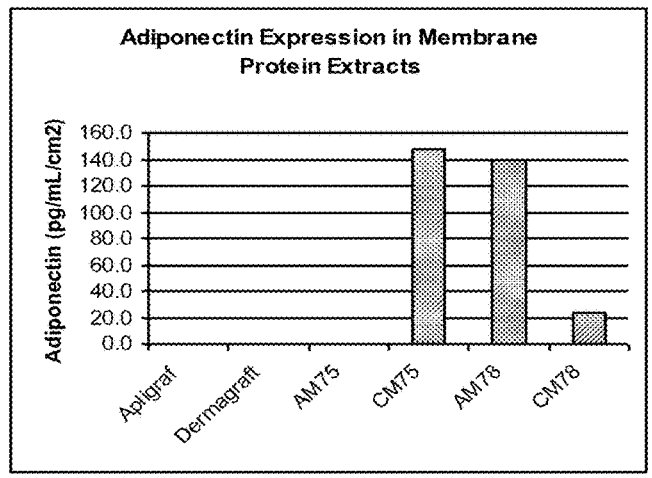

Preliminary protein array data analyses showed that the majority of selected testing factors (refer to Table 11) were expressed in amniotic membrane, chorionic membrane, Apligraf, and Dermagraft. Three proteins were identified as unique for the amniotic membrane and/or the chorionic membrane which are undetectable in Apligraf and Dermagraft. These proteins are EGF, IGFBP1, and Adiponectin. All three proteins are important for wound healing. FIG. 13 depicts expression of EGF (A), IGFBP1 (B), and Adiponectin (C) in amniotic or chorionic membranes. AM75 and AM 78 are placental products of the present invention (e.g. cryopreserved), CM75 and CM78 are cryopreserved chorionic membrane products. These proteins are believed by the inventors to facilitate the therapeutic efficacy of the present placental products for wound healing.

These data indicate that the present methods can produce placental products that comprise an amniotic membrane containing EGF, IGFBP1, and/or adiponectin.

Example 19 Wound Healing Proteins are Secreted for a Minimum of 14 Days

Placental products of the present invention demonstrate a durable effect, desirable for wound healing treatments. The extracellular matrix and presence of viable cells within the amniotic membrane described in this invention allow for a cocktail of proteins that are known to be important for wound healing to be present for at least 14 days. Amniotic membranes were thawed and plated onto tissue culture wells and incubated at 37° C.±2° C. for 3, 7, and 14 days. At each time point, a sample of the culture supernatant was collected and measured through protein array analysis as described in Example 18. Table 12 illustrates the level of various secreted factors in tissue culture supernatants from two donors of amniotic membranes at 3, 7 and 14 days as measured through protein array analysis.

TABLE 12

Levels of proteins secreted in amnion tissue culture supernatants at different time points (pg/ml).

|  | Day 3 | Day 7 | Day 14 |
| --- | --- | --- | --- |
| hACRP30 | 548.03 | 766.73 | 371.56 |
| hAlpha2Macroglobulin | 69687.55 | 31764.00 | 48477.62 |
| hANG2 | 0.00 | 9.28 | 1.65 |
| hEGF | 3.06 | 2.51 | 2.32 |
| hbFGF | 40.80 | 85.46 | 269.97 |
| hFibronectin | 1932101.25 | 3506662.00 | 6019286.50 |
| hHBEGF | 41.78 | 80.50 | 78.09 |
| hHGF | 5358.09 | 9327.67 | 18081.16 |
| hIGFBP1 | 2654.57 | 6396.11 | 4666.88 |
| hIGFBP2 | 4379.76 | 23797.46 | 21784.21 |
| hIGFBP3 | 36030.52 | 107041.71 | 13350.99 |
| hIL1ra | 116593.20 | 675.09 | 4927.52 |
| hKGF | 7.29 | 13.86 | 36.59 |
| hMMP1 | 323249.53 | 1727765.60 | 15272931.52 |
| hMMP10 | 14804.44 | 20557.91 | 16194.56 |
| hMMP13 | 92.92 | 408.17 | 399.01 |
| hMMP2 | 38420.90 | 322500.72 | 3283119.13 |
| hMMP3 | 66413.54 | 283513.74 | 3598175.53 |
| hMMP7 | 128.51 | 147.65 | 4005.14 |
| hMMP8 | 463.32 | 2109.21 | 2331.47 |
| hMMP9 | 6139.53 | 25810.38 | 60483.67 |
| hNGAL | 15754.19 | 70419.63 | 721923.09 |
| hPDGFAA | 18.02 | 58.69 | 16.31 |
| hPDGFAB | 16.58 | 58.41 | 28.30 |
| hPDGFBB | 1.94 | 21.67 | 5.84 |

TABLE 12-continued

Levels of proteins secreted in amnion tissue culture supernatants at different time points (pg/ml).

|  | Day 3 | Day 7 | Day 14 |
| --- | --- | --- | --- |
| hPEDF | 6793.74 | 21645.90 | 169990.84 |
| hSDF1b | 0.00 | 24.09 | 37.12 |
| hTGFa | 15.05 | 14.89 | 205.90 |
| hTGFb1 | 334.07 | 341.53 | 680.33 |
| hTGFb2 | 119.59 | 207.79 | 731.96 |
| hTIMP1 | 197743.23 | 437492.21 | 247661.65 |
| hTIMP2 | 4724.25 | 19970.76 | 189810.51 |
| hTSP1 | 0.00 | 0.00 | 1274.62 |
| hTSP2 | 13820.61 | 59695.21 | 991366.59 |
| hVEGF | 44.98 | 57.45 | 7.40 |
| hVEGFC | 548.03 | 766.73 | 371.56 |

Example 20 Interferon 2α (IFN-2α) and Transforming Growth Factor-β3 (TGF-β3)

Placental products described in this invention have been analyzed for the presence of IFN-2α and TGF-β3. Briefly, after thawing, the membranes were homogenized and centrifuged at 16,000 g to collect the resulting supernatants. Supernatants were analyzed on a commercially available ELISA kit from MabTech (IFN-2α) and R&D Systems (TGF-63). FIG. 14 shows significant expression of IFN-2α (A) and TGF-63 (B) in placental product homogenates.

Without being bound by theory, interferon-2α and TGF-63 may aid in the prevention of scar and contracture formation. IFN-2α may serve a role to decrease collagen and fibronectin synthesis and fibroblast-mediated wound contracture.

Example 21 Tissue Reparative Proteins in Amniotic Membranes

Placental product homogenates were analyzed for the presence of proteins that are important in tissue repair.

Figure 15A:
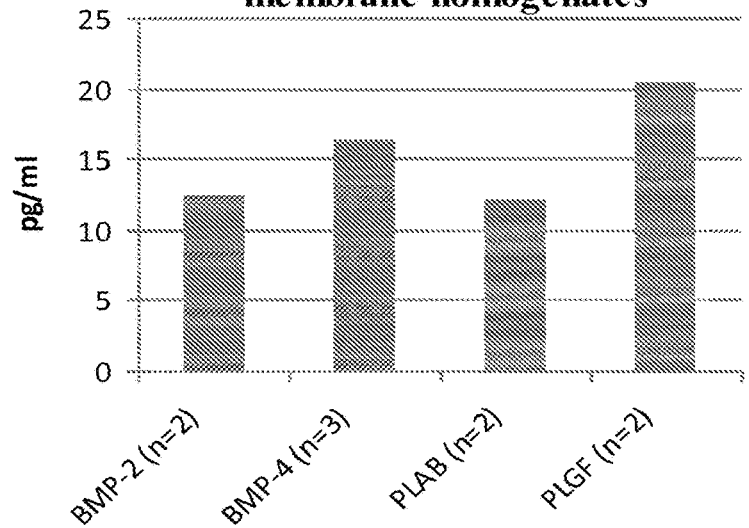
FIG. 15 A-B depict expression of BMP-2, BMP-4, PLAB, PIGF (FIG. 15A), and IGF-1 (FIG. 15B) in amniotic membrane homogenates.
Figure 15B:
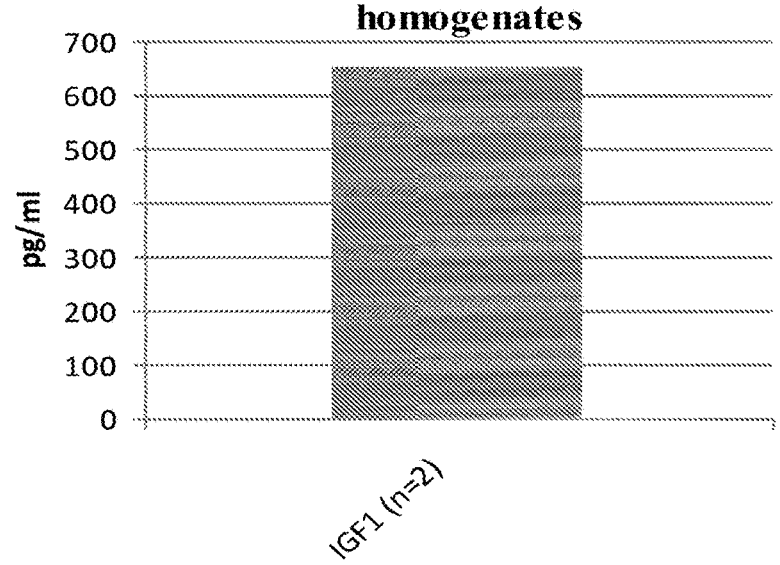

Placental product described in this invention have been analyzed for the presence of tissue reparative proteins. Briefly, the thawed products were incubated in DMEM+ 10% FBS for 72 hrs. The membranes were then homogenized in a bead homogenizer with the culture media. The homogenates were centrifuged, and the supernatants were analyzed on commercially available ELISA kits from R&D Systems. FIG. 15 shows significant expression of BMP-2, BMP-4, PLAB, PIGF, and IGF-1 in several donors of amniotic membranes.

Without being bound by theory, the inventors believe that efficacy of the present placental products for wound repair are due, in part, to the role of BMPs, IGF-1, and PIGF in the development and homeostasis of various tissues by regulating key cellular processes. BMP-2 and BMP-4 may stimulate differentiation of MSCs to osteoblasts in addition to promote cell growth; placental BMP or PLAB is a novel member of the BMP family that is suggested to mediate embryonic development. Insulin-like growth factor 1 (IGF-1) may promotes proliferation and differentiation of osteoprogenitor cells. Placental derived growth factor (PIGF) may acts as a mitogen for osteoblasts.

Example 22 MMPs and TIMPs

Both MMPs and TIMPs are among the factors that are important for wound healing. However, expression of these proteins must be highly regulated and coordinated. Excess of MMPs versus TIMPS is a marker of poor chronic wound healing. We investigated expression of MMPs and TIMPs and its ratio in amniotic membrane and chorionic membrane and compared it to the expression profile in Apligraf and Dermagraft.

Figure 16:
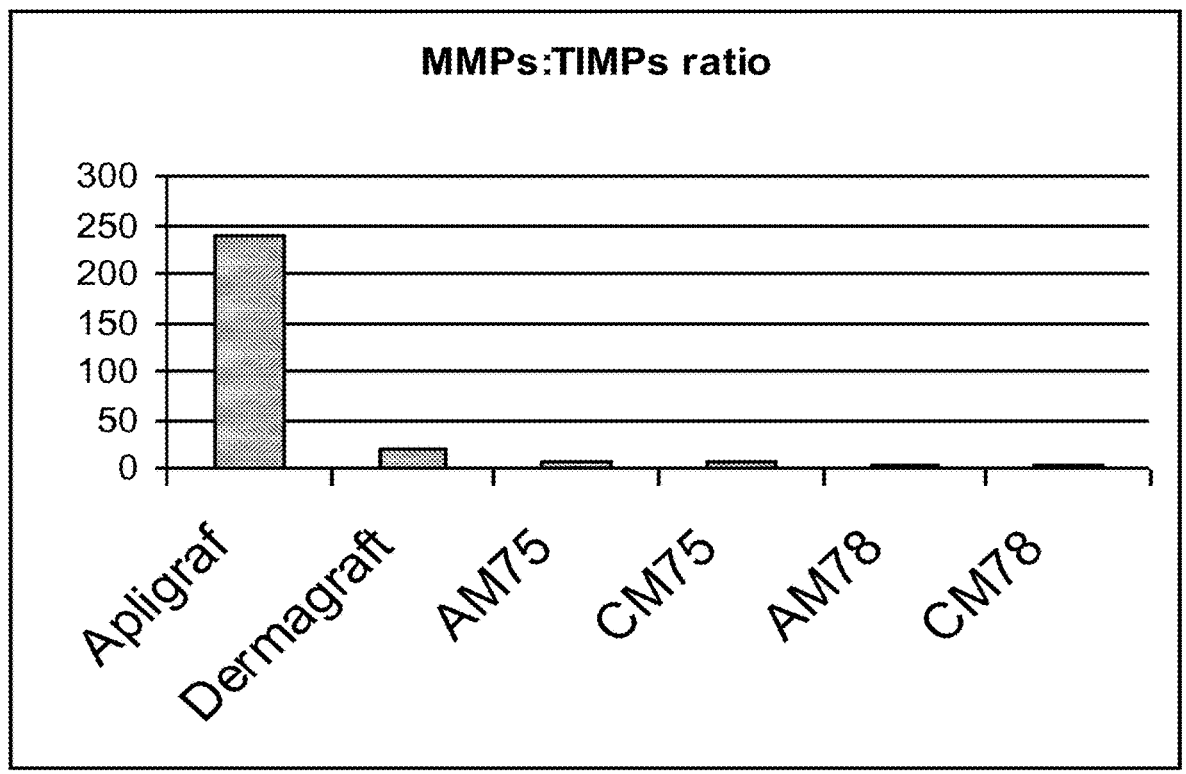
FIG. 16 depicts the ratio of MMPs to TIMPs in various membrane products.

Results showed that all membranes express MMPs and TIMPs; however, the ratio in the thawed placental products and chorionic membranes is significantly lower. Therefore, these membranes will be more beneficial for wound healing (FIG. 16).

Accumulated data indicate that the MMP to TIMP ratio is higher in cases of non-healing wounds. For example, the ratio between MMP-9 and TIMP1 is approximately 7-10 to one for good healing and 18-20 or higher for poor healing. Analysis of the ratio between MMPs and TIMPs secreted by placental tissues, Apligraf, and Dermagraft showed that the amniotic and chorionic membrane products contain MMPs and TIMPs at an approximate ratio of 7, which is favorable for wound healing. In contrast, Dermagraft had a ratio >20, and Apligraf had a ratio >200.

These data indicate that the present methods can produce placental products that comprise an amniotic membrane containing MMP-9 and TIMP1 at a ratio of about 7-10 to one.

Example 23 α2-Macroglobulin

α2-macroglobulin is known as a plasma protein that inactivates proteinases from all 4 mechanistic classes, serine proteinases, cysteine proteinases, aspartic proteinases, and metalloproteinases. Another important function of this protein is to serve as a reservoir for cytokines and growth factors, examples of which include TGF, PDGF, and FGF. In the chronic wounds like diabetic ulcers or venous ulcers, the presence of high amount of proteases leads to rapid degradation of growth factors and delays in wound healing. Thus, the presence of α2-macroglobulin in products designed for chronic wound healing will be beneficial. Results of the protein array analysis showed that amniotic and chorionic membranes contain α2-macroglobulin (Table 13). Although these preliminary data show high variability between donors, the importance of this protein in wound healing prompted the additional evaluation of α2-macroglobulin in placental tissues using a single analyte ELISA instead of protein array, which is a useful tool to evaluate the presence of multiple proteins in one sample for profiling.

These data indicate that the present methods can produce placental products that comprise an amniotic membrane containing α2-macroglobulin.

TABLE 13

Expression of α2-macroglobulin in placental tissue protein extracts.

| Sample | α 2-macroglobulin (pg/mL/cm$^2$) |
|---|---|
| AM75 | 7 |
| CM75 | 790 |
| AM78 | 53042 |
| CM78 | 1014 |

Example 24 Establishment of EGF as a Marker for Amniotic Tissue Potency

EGF is among the factors that are important for wound healing (Schultz et al., 1991, Komarcevic, 2000, and Hong et al., 2006). The absence or decreased amount of EGF is one characteristic of chronic wounds (Harding et al., 2002). Evaluation of proteins derived from amniotic membrane samples prepared according to the developed manufacturing process disclosed by the present application reveal that EGF is one of the major factors secreted in higher quantities by these tissues. The importance of EGF for wound healing together with high levels of EGF detected in the presently disclosed amniotic membranes support selection of EGF as a potency marker for evaluation of membrane products manufactured for clinical use pursuant to the present disclosure. A commercially available ELISA kit from R&D Systems was selected for evaluation of its suitability to measure EGF secreted by amniotic membranes. ELISA qualification meets the standards established by the FDA and ICH guidances for bioanalytical assay validation (Validation of Analytical Procedures: Text and Methodology Q2(R1), 1994; ICH Harmonized Tripartite Guideline and Guidance for Industry Bioanalytical Method Validation, 2001). Amniotic membranes evaluated for expression of EGF by this method confirmed protein array data and further demonstrated that EGF was a unique factor expressed at clinically significant levels in these tissues.

Example 25 Amniotic Tissue Expression of EGF

Protein array analysis provided initial evidence that EGF was uniquely expressed in amniotic membranes but not in chorionic membranes (Table 14). The levels of EGF measured in amniotic membranes were of clinical significance.

TABLE 14

Protein array data showing range of expression of EGF in amniotic and chorionic membranes from multiple donors.

| | Amnion (pg/ml) | Chorion (pg/ml) |
|---|---|---|
| EGF | 127.3-361.4 | 0-0.8 |

These data indicate that the present methods can produce placental products that comprise a amniotic membrane containing EGF, optionally in substantial amounts.

Homogenate of Placental Products

Placental products were thawed until no remaining frozen cryomedia was present. Membranes were then removed from bags and cut into 4 cm×2 cm pieces while still adhered to nitrocellulose. Each piece of tissue was then removed from the nitrocellulose and washed twice with PBS. Each tissue was then snap frozen in a homogenization tube using liquid nitrogen. Subsequently, one pre-cooled 5 mm steel bead was added to each tube; samples were then homogenized using a Qiagen Tissue Lyser according to the manufacturer's recommendations in 500 μL homogenization media. Tissue homogenates were stored at −80° C.±5° C. until analyzed by ELISA for EGF expression.

ELISA Procedure and Validation

Samples were analyzed for the expression of EGF using the Quantikine Human EGF ELISA Kit (R&D Systems) according to the manufacturer's recommendations. Several parameters were tested to establish the test criteria and to show the suitability of this ELISA kit to measure EGF in placental tissue samples. Assay performance was assessed by analyzing linearity, range, lower and upper limits of quantitation (LLOQ and ULOQ), precision, accuracy, and robustness. Experimental data (Table 14) showed that the quantitation range of this assay was 3.9-250 pg/mL EGF. The intra- and inter-assay CVs ranged from 1.22 to 5.80% and 2.73 to 7.53%, respectively. Additionally, sample recovery analysis demonstrated accuracy within 20%. Furthermore, this assay showed dilutional linearity and specificity. Ruggedness was also demonstrated by assay insensitivity to variations introduced by different analysts.

TABLE 15

Established ELISA parameters for measuring EGF in placenta homogenates.

| | |
|---|---|
| Calibration Standard Range | 3.9-250 pg/mL |
| Assay Quantitation Range | 7.8-250 pg/mL |
| LLOQ | 7.8 pg/mL |
| LOD | 2.18 pg/mL |
| ULOQ | 250 pg/mL |

EGF Expression in Amniotic Membranes

Figure 17:
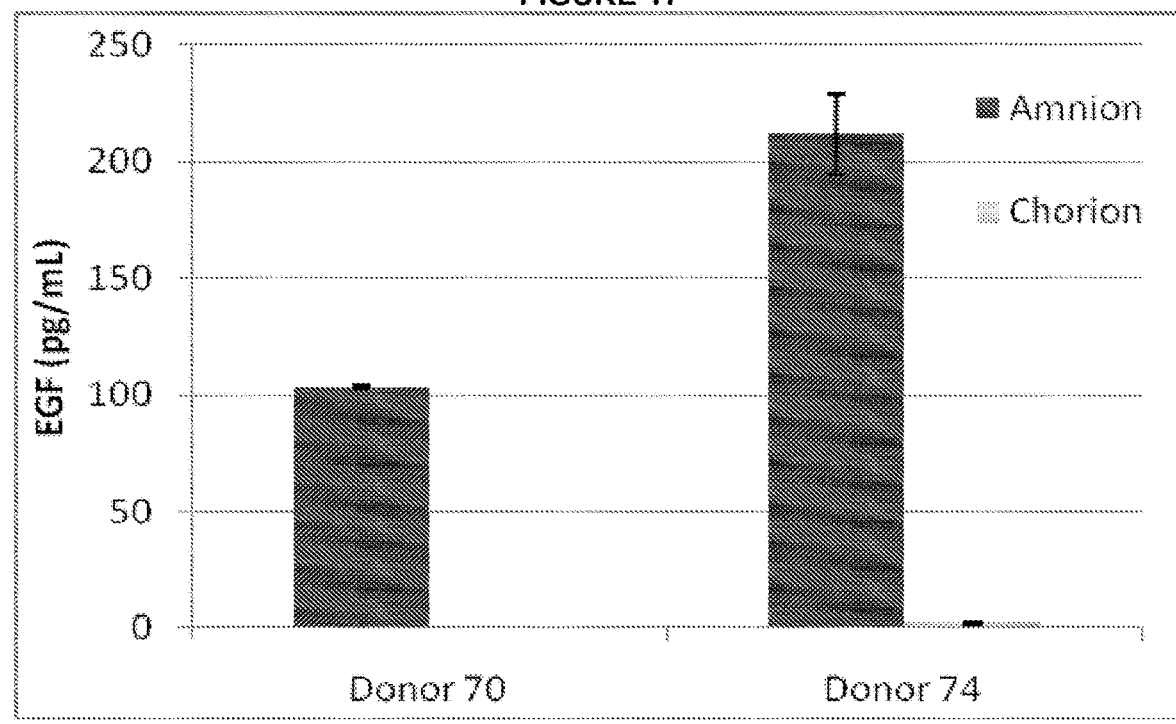
FIG. 17 depicts expression of EGF in chorion and amnion membranes measured by ELISA in two separate placenta donors.

Measurement of EGF in amniotic preparations has proven to be both reliable and reproducible. Measurement of EGF in multiple donors showed that this method of quantification was a valuable means of evaluating potency in tissue prepared pursuant to the present disclosure for use in a clinical setting. FIG. 17 shows representative expression of EGF in a thawed placental product and chorionic membrane prepared and analyzed by the methods described above. Results have been reproduced in multiple tissue preparations.

These data indicate that the present methods can produce placental products that comprise an amniotic membrane containing EGF.

Example 26 Placental Tissues Enhance Cell Migration and Wound Healing

The process of wound healing is highly complex and involves a series of structured events controlled by growth factors (Goldman, 2004). These events include increased vascularization, infiltration by inflammatory immune cells, and increases in cell proliferation. The beginning stages of wound healing revolve around the ability of individual cells to polarize towards the wound and migrate into the wounded area in order to close the wound area and rebuild the surrounding tissue. Upon proper stimulation, several different types of cells including epithelial, endothelial, mesenchymal, and fibroblastic cells are implicated in the wound healing process (Pastar et al, 2008 and Bannasch et al., 2000). Specifically, they proliferate and migrate into the wound area to promote healing. Therefore, experiments were conducted to determine if factors secreted from amniotic and chorionic membranes produced pursuant to the present disclosure promote cell migration and wound field closure. To accomplish this, a commercially available wound healing assay (Cell Biolabs) and a highly accepted human microvascular endothelial cell line (HMVEC, Lonza Inc.) were utilized. Results indicated that cell migration was enhanced by treatment with conditioned media from the placental membranes.

In Vitro Cell Migration Assay

Human microvascular endothelial cells (HMVECs) were grown under normal cell culture conditions in defined complete media (Lonza Inc.). To assess migration and wound field closure, a commercially available wound healing assay was used (Cell Biolab).

Figure 18:
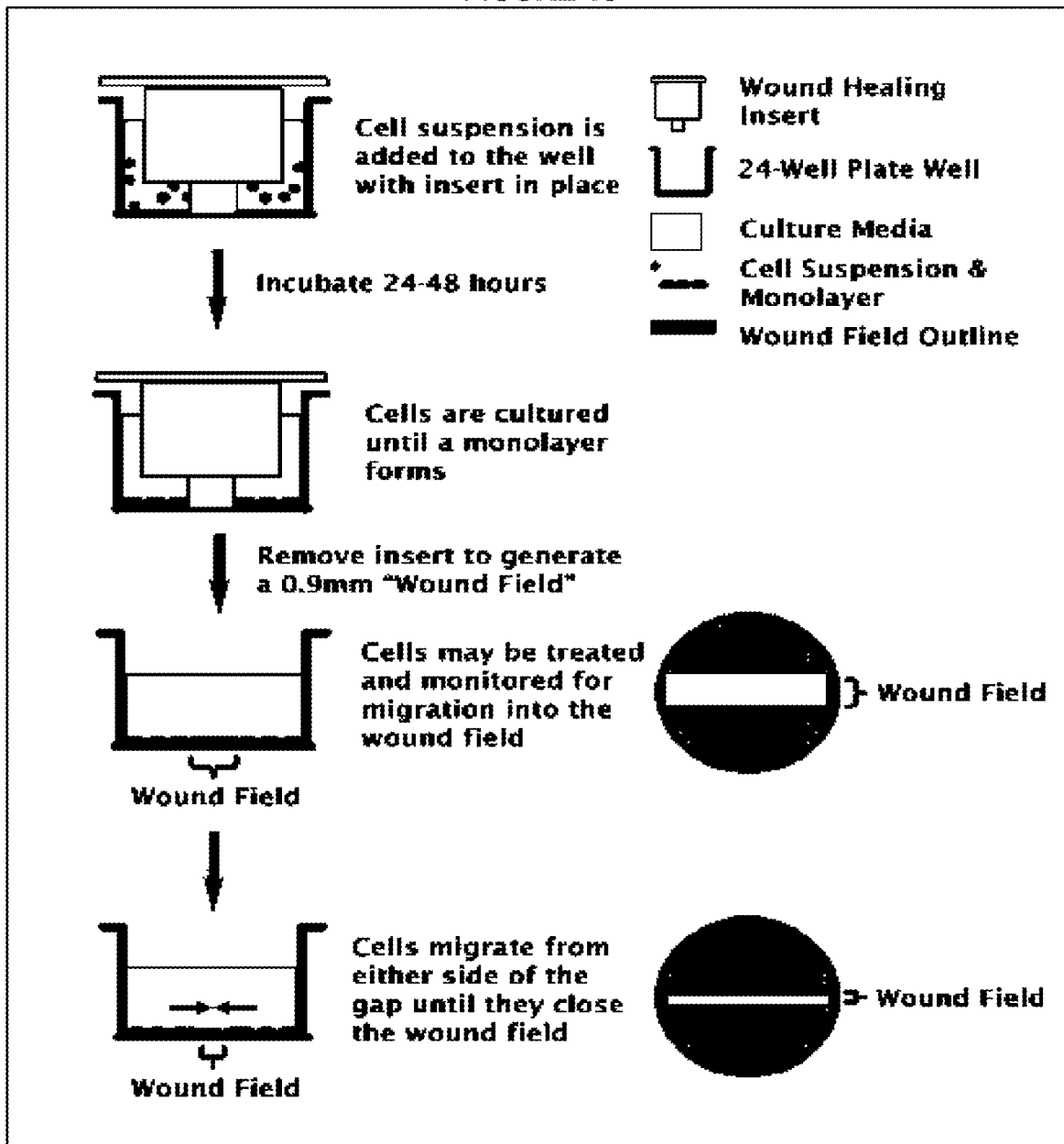
FIG. 18 depicts the Cell Biolabs 24-well Cytoselect wound healing assay.

FIG. 18 depicts the Cell Biolabs 24-well Cytoselect wound healing assay. (Figure reproduced from Cell Biolabs).

Cells were collected via trypsinization, pelleted, and counted before being resuspended in complete media at a density of $2 \times 10^5$ cells/mL. 250 μL ($5 \times 10^4$ cells) of cell suspension was then pipetted into each side of a well containing a wound healing insert (Cytoselect 24-well Wound Healing Assay Plate, Cell Biolabs). The cells were grown for 24 hours in complete media. After 24 hours, the wound inserts were removed. At the same time, complete media was removed and replaced with experimental media. Complete media and basal media were used as positive and negative controls, respectively. To generate experimental media, placental membranes were incubated for 3 days in DMEM with 1% human serum albumin (HSA) in a tissue culture incubator. The resulting tissue and media were then placed in eppendorf tubes and spun at high speed in a microcentrifuge. The supernatants were collected and stored at $-80°$ C.$\pm 2°$ C. until use. For migration and wound healing studies, conditioned media from placental membranes was diluted 1:20 in basal media before being added to experimental wells. After 18 hours, the media was removed, and the cells were fixed for 20 min in 4% paraformaldehyde and stained with crystal violet. The wound field in each well was then photographed. Wound healing was determined by the amount of wound field still visible at the end of the experiment when compared to control pictures taken before conditioned media was added to the wells.

Placental Membrane Conditioned Media Supports Cell Migration and Wound Field Closure Conditioned media from amniotic and chorionic membranes was used to assess the potential for these membranes to promote cell migration and wound field closure. Conditioned media from placental amniotic, chorionic, and a combination of amniotic/chorionic membranes supported migration of cells into the experimental wound field.

Figure 19:
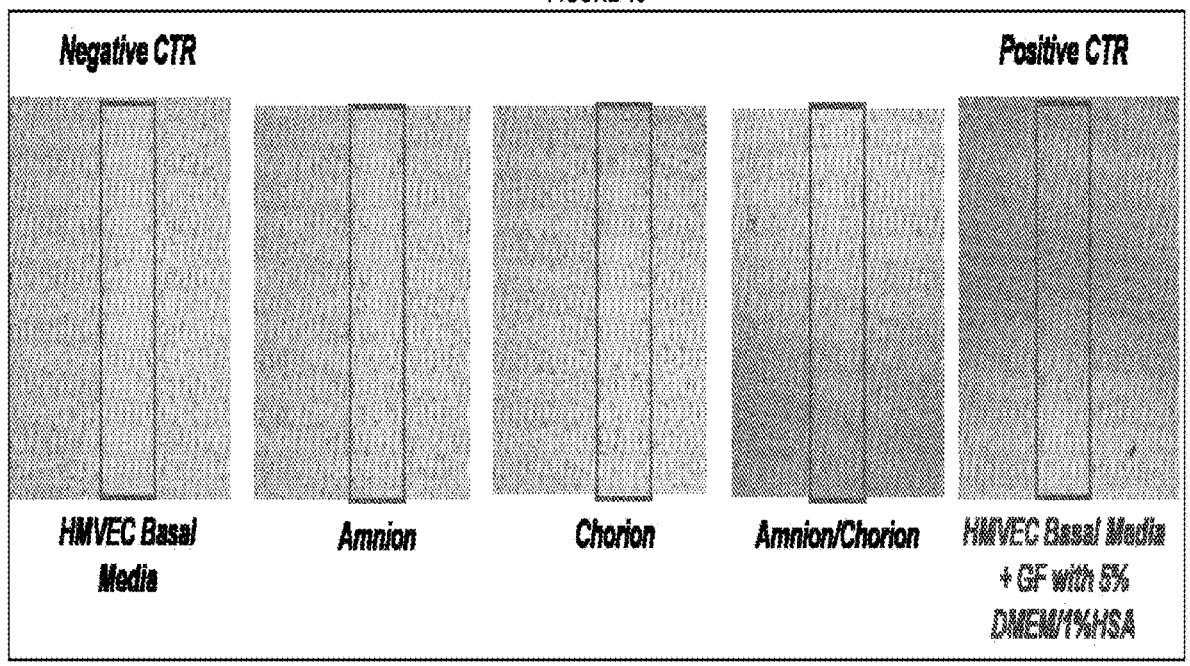
FIG. 19 depicts representative images of HMVECs treated with 5% conditioned media from amniotic, chorionic, or a combination of amniotic/chorionic preparations.
Figure 20A:
FIG. 20A-E depict the remarkable efficacy of placental products for treating diabetic foot ulcers in patient 1.
Figure 20B:
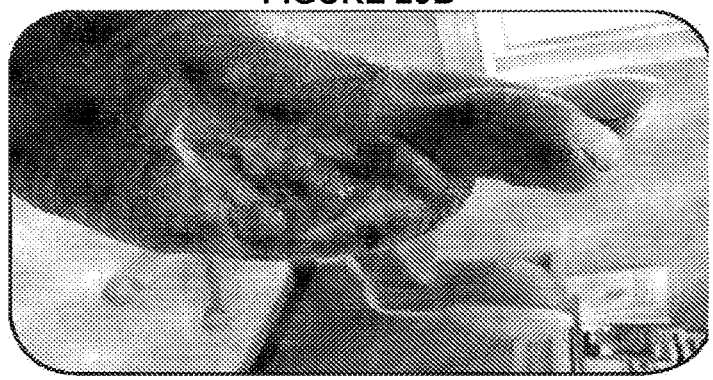
Figure 20C:
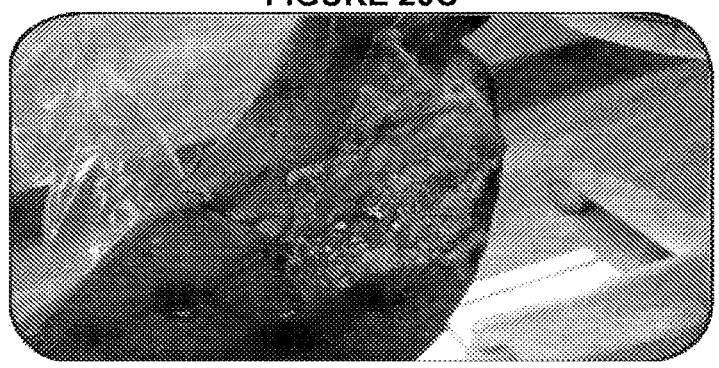
Figure 20D:
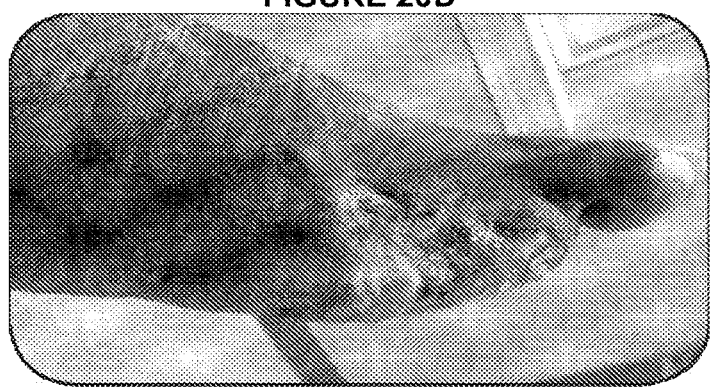
Figure 20E:
Figure 21A:
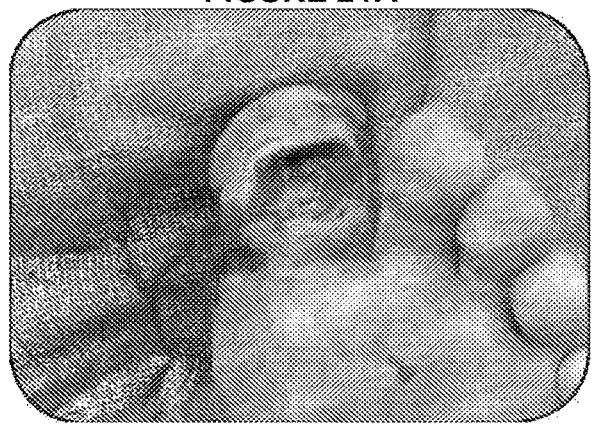
FIG. 21A-E depict the remarkable efficacy of placental products for treating diabetic foot ulcers in patient 2.
Figure 21B:
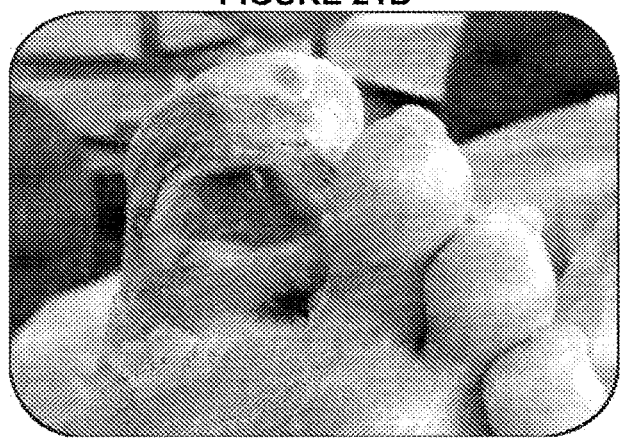
Figure 21C:
Figure 21D:
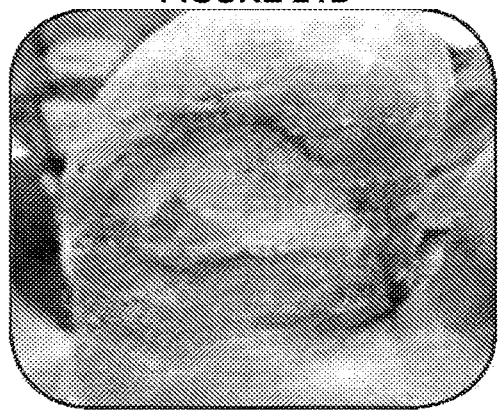
Figure 21E:

FIG. 19 depicts representative images of cells treated with 5% conditioned media from amniotic, chorionic, or a combination of amniotic/chorionic tissue as well as positive and negative controls. Wound field is 0.9 mm in width.

The ability of factors from placental membranes produced pursuant to the present disclosure to promote HMVEC migration indicated that these tissues have the ability to enhance wound healing. Additionally, based on the insight of the inventors, it has been surprisingly discovered that these tissues also enhance revascularization since the HMVEC cell line is derived from vascular endothelial cells.

These data demonstrate that the methods of manufacture according to the present invention produce placental products with unexpectedly superior levels of factors that promote wound healing.

Example 27 Biochemical Profile of the Supernatants from Examplary Placental Tissue Products Table 16 depicts the biochemical profile of the supernatants of examplary placental products of the invention (results adjusted per $cm^2$ after subtraction of the negative background).

TABLE 16

Factors in Placental Tissue Product (pg/cm$^2$).

| | Units | Apligraf | Dermagraft | AM75 | CM75 | AM78 | CM78 |
|---|---|---|---|---|---|---|---|
| hMMP1 | pg/ml/cm$^2$ | 1964945.37 | 14818.20 | 2821.85 | 3531.81 | 117326.89 | 95.46 |
| hMMP7 | pg/ml/cm$^2$ | 911.54 | 0.00 | 0.00 | 0.00 | 3.96 | 0.00 |
| hMMP10 | pg/ml/cm$^2$ | 0.00 | 0.00 | 113.94 | 0.00 | 0.00 | 0.00 |
| hMMP13 | pg/ml/cm$^2$ | 21.61 | 0.00 | 0.00 | 0.00 | 0.71 | 0.00 |
| hMMP3 | pg/ml/cm$^2$ | 208281.70 | 180721.52 | 170.26 | 161.52 | 8325.17 | 0.00 |
| hMMP9 | pg/ml/cm$^2$ | 8872.28 | 19321.39 | 214.78 | 1455.11 | 630.56 | 57.59 |
| hMMP2 | pg/ml/cm$^2$ | 153341.77 | 19712.21 | 287.14 | 37.93 | 3823.38 | 24.44 |
| hMMP8 | pg/ml/cm$^2$ | 36.92 | 12.19 | 0.00 | 0.00 | 0.00 | 0.00 |
| hTIMP1 | pg/ml/cm$^2$ | 2487.18 | 10909.84 | 569.23 | 883.05 | 28743.48 | 97.94 |
| hTIMP2 | pg/ml/cm$^2$ | 7285.53 | 1796.56 | 89.29 | 13.72 | 424.06 | 4.83 |
| MMP/TIMP | | 239.26 | 19.72 | 6.81 | 6.26 | 4.50 | 2.62 |

Example 28 Biochemical Profile of the Lysates from Examplary Placental Tissue Products Table 17 depicts the biochemical profile of the lysates of examplary placental tissue products of the invention (results adjusted per cm$^2$ after subtraction of the negative background).

TABLE 17

| | AM75 lysate pg/ml | AM78 lysate pg/ml | CM75 lysate pg/ml | CM78 lysate pg/ml |
|---|---|---|---|---|
| hACRP30 | 50.8 | 1154.6 | 1213.7 | 225.3 |
| hAlpha2-Macroglobulin | 1910.6 | 426191.6 | 8174.4 | 9968.6 |
| hEGF | 127.3 | 361.4 | 0.0 | 0.8 |
| hbFGF | 119.1 | 821.5 | 375.0 | 351.3 |
| hGCSF | 0.7 | 3.2 | 1.2 | 0.7 |
| hHBEGF | 127.5 | 168.0 | 15.4 | 84.5 |
| hHGF | 3943.7 | 15060.0 | 29979.6 | 50392.8 |
| hIGFBP1 | 5065.0 | 9456.6 | 934.0 | 1443.6 |
| hIGFBP2 | 12460.8 | 5569.7 | 135.9 | 134.6 |
| hIGFBP3 | 50115.7 | 41551.4 | 4571.5 | 11970.2 |
| hIL1ra | 3881.0 | 32296.9 | 5168.2 | 525.5 |
| hKGF | 1.4 | 8.8 | 3.1 | 1.5 |
| hLIF | 0.0 | 4.2 | 0.0 | 0.0 |
| hMMP1 | 9144.1 | 20641.2 | 2882.9 | 6582.3 |
| hMMP10 | 0.0 | 15.5 | 79.3 | 87.5 |
| hMMP2 | 2067.3 | 4061.9 | 949.5 | 748.8 |
| hMMP3 | 0.0 | 36.2 | 0.0 | 0.0 |
| hMMP7 | 5.1 | 11.4 | 4.5 | 9.1 |
| hMMP8 | 0.0 | 0.0 | 0.0 | 0.0 |
| hMMP9 | 92.2 | 2878.1 | 2676.2 | 1259.3 |
| hNGAL | 6900.1 | 6175.9 | 938.5 | 229.7 |
| hPDGFAA | 0.0 | 12.5 | 39.8 | 35.2 |
| hPDGFAB | 11.2 | 31.3 | 14.4 | 14.0 |
| hPDGFbb | 4.6 | 13.4 | 4.0 | 1.3 |
| hPEDF | 0.0 | 652.6 | 0.0 | 0.0 |
| hTIMP1 | 7958.1 | 35955.6 | 50712.3 | 17419.9 |
| hTIMP2 | 3821.8 | 7443.2 | 640.7 | 780.0 |
| hVEGF | 3.3 | 11.8 | 125.2 | 8.4 |
| hVEGFC | 46.5 | 150.0 | 123.5 | 51.7 |
| hVEGFD | 25.7 | 31.0 | 15.0 | 20.4 |

Example 29 Use of Placental Products for Treating Diabetic Foot Ulcers

Purpose: Despite bioengineered skin substitutes that contain human fibroblasts or a combination of human fibroblasts and keratinocytes, published rates of chronic wound healing remain low, with approximately half of all wounds recalcitrant to even these newer therapies. Morbidity and mortality from diabetic foot ulceration are substantial as the 5 year mortality rate following a lower extremity amputation is between 39% and 68%. (Page J. J of Foot & Ankle Surgery 2002; 41(4):251-259; Isumi Y., et al. Diabetes Res and Clin Practice 2009; 83:126-131).

A instant membrane product, which provides necessary angiogenic and anti-inflammatory growth factors was introduced in an effort to improve outcomes of patients with chronic skin ulceration at-risk for amputation.

Objective: Patients with chronic diabetic foot ulceration, unresponsive to available therapy and at-risk for amputation were considered for treatment. All wounds were aggressively debrided prior to graft application. Patients were evaluated regularly and application of a membrane product of the present invention was at the discretion of the treating physician. Offloading was encouraged in both patients.

INTRODUCTION

According to the United States Food and Drug Administration (FDA), a chronic, cutaneous ulcer is defined as a wound that has failed to proceed through an orderly and timely series of events to produce a durable structural, functional and cosmetic closure(2). The most common chronic wounds include pressure ulcers and leg ulcers. The triad of peripheral neuropathy, deformity, and minor trauma has emerged as the most frequent causes of insult that lead to foot ulcerations. In terms of healing rates, an appropriate benchmark for a chronic wound is a decrease of 10% to 15% in size every week, or 50% decrease in size over a one-month period. A three-year retrospective cohort study performed by Ramsey et al. of 8,905 patients in a large health maintenance organization who have diabetes reported a 5.8% cumulative incidence of ulceration. At the time of diagnosis, 15% of these patients developed osteomyelitis and 16% required partial amputation of a lower limb.

Approximately 80% to 85% of lower extremity amputations are preceded by foot ulcerations. Morbidity and mortality from diabetic foot ulceration are substantial as the 5 year mortality rate following a lower extremity amputation is between 39% and 68%. (2). These mortality rates are higher than the five-year mortality rates for breast cancer, colon cancer, and prostate cancer.

Despite all of the advances in bioengineered tissue for the treatment of chronic diabetic ulcerations, there are an abundance of patients whose ulcerations are resistant to therapy, and result in a chronic wound. Because of healing rates that only approach 50% with these newer therapies, the use of stem cells in regenerative medicine has been of particular interest recently. The ultimate aim is to promote restoration of functional skin. A preliminary study was performed by Fiami et al. in which they isolated mesenchymal stem cells from umbilical cord blood and inoculated them onto a piece of de-epithelialized dermis. The results of this preliminary study showed that peripheral stem cells are capable of surviving and expressing neoangiogenesis. In addition to showing promise for tissue repair, mesenchymal stem cells exhibit low immunogenicity and can be transplanted universally without having to undergo compatibility testing between the donor and recipient.

In this study, clinical evidence of remarkable healing using an instant membrane product for the treatment of two chronic wounds that amputation was considered. The fundamentals of wound management are still the cornerstone of comprehensive wound care in any treatment protocol including adequate debridement, offloading, maintaining a moist environment, and adequate perfusion and infection control.

Materials

An instant membrane product was made as taught herein, comprising an allograft derived from the amnion comprising a bilayer of native epithelial cells on a basement membrane and a stoma layer consisting of neonatal fibroblasts, extracellular matrix (ECM) and mesenchymal stem cells (MSC).

Limb Salvage: Case One

History and Physical Examination

A 70 year old male presented to the emergency department with bulla formation on the dorsolateral aspect of his right foot between the fourth and fifth digits, edema and pain, and a small lesion lateral to the fifth digit. The patient reported a history of minor trauma to the area two weeks prior to presentation. The patient had a history of type II diabetes mellitus, hypertension, heart failure, chronic obstructive pulmonary disease, and chronic kidney disease treated with hemodialysis three times a week. The patient had a surgical history of an aorta-venous graft replacement. He denied any history of alcohol, tobacco or drug use. Physical exam revealed no active purulent drainage or malodor, and no tenderness on palpation. The vascular exam revealed non-palpable pulses in the dorsalis pedis and posterior tibial arteries. Doppler exam revealed a monophasic dorsalis pedis pulse with a biphasic posterior tibial artery pulse. The fifth digit had gangrenous changes and was cold on palpation. There were ischemic changes of the fourth digit. Radiographic evaluation revealed scattered air densities indicative of soft tissue gas in the fourth interspace as well as the tip of the fifth digit.

Preoperative Management

The patient was started on intravenous antibiotics of vancomycin and piperacillin and tazobactam at appropriate renal dosing.

Operative Management

The patient was taken to the operating room where an incision and drainage of the fourth interspace was performed, and a partial fifth ray amputation to the level of the metatarsal head was performed without complication. The wound was left open and packed with sterile gauze moistened with sterile normal saline, and covered with a sterile compressive dressing. Intraoperative findings revealed liquefactive necrosis of surrounding tissues with purulence and malodor. The patient underwent 2 subsequent surgical debridements, with the second resulting in further removal of the fourth and fifth metatarsal shafts. In a third surgery further debridement of necrotic soft tissue and amputation of the fourth digit was performed. On May 20, 2010 treatment with an instant membrane product was initiated. Prior to the graft placement the patient had undergone successful recanalization of the popliteal artery and the peroneal artery without significant residual stenosis.

Postoperative Course

The patient followed up with his podiatric surgeon within 2 days of being discharged from the hospital. Upon initial exam, there were no clinical signs of infection, and the proximal dorsal incision appeared coapted. The third digit was dusky and cool in appearance. Radiographs were taken which showed no evidence of soft tissue gas or acute osteomyelitis. A dry sterile dressing was applied. The patient received applications of the instant membrane product at 6 additional visits in an outpatient office. Prior to each application the wound was evaluated for abscess, cellulitis, drainage, hematoma formation, and infection. At each visit, the wound decreased in size and appeared more granular in nature as compared to previous visits. At the time of the third application the wound had decreased in size 50%.

At 19 weeks the wound was considered closed, and the patient was instructed to remain weight bearing on the affected limb with the use of a surgical shoe only.

Photographs of the remarkable wound healing mediated by a placental product of the present invention as shown in FIG. 20. Panel A: First application of an instant membrane product; B: 8 weeks post first an instant membrane product application; C: 10½ weeks post first an instant membrane product application; D: 12 weeks post first an instant membrane product application; E: 19 weeks post first an instant membrane product application.

Limb Salvage: Case Two

History and Physical Examination

A 44-year old male presented to an outpatient office with a large ulceration on the plantar aspect of his left hallux, secondary to a previous trauma a few weeks prior to the visit. The patient had a history of diabetes mellitus for the past five years complicated by peripheral neuropathy, hypertension, dyslipidemia, and osteomyelitis. Past surgical history included abdominal aortic aneurysm repair and circumcision. On physical exam the ulceration measured 4.0 cm×2.0 cm×1.5 cm, probing to the distal phalanx with exposed tendon. There was no ascending cellulitis or lymphangitis, and no increased temperature gradient. Capillary fill time, hair growth, and tissue turgor were all normal. There were palpable pulses in the dorsalis pedis and the posterior tibial artery. Radiographic exam was negative for soft tissue gas. Magnetic resonance imaging revealed osteomyelitis in the distal aspect of the proximal phalanx and the distal phalanx of the great toe with a small soft tissue abscess in the region of the dorsal soft tissue adjacent to the distal phalanx.

Preoperative Management

The patient was started on intravenous antibiotics. He was taken to the operating room for excisional debridement of all nonviable tissue and application of the instant membrane product.

Operative Management

The ulceration was debrided to healthy tissue with utilization of both sharp dissection and Versajet™, leaving the head of the proximal phalanx exposed plantarly. The instant membrane product was then placed over the wound bed and exposed bone. The patient tolerated the procedure without complication. The patient was discharged from the hospital the day after surgery on a five week course of intravenous antibiotic therapy.

Postoperative Course

The patient was instructed to remain strictly non-weight bearing to the affected limb, and returned for follow-up on post-operative day 6. The dressing was clean, dry and intact. There were no post-operative complications such as abscess, cellulitis, discomfort, or drainage and no clinical signs of infection. The patient received a total of 7 stem cell graft applications over the course of the next 8 weeks. At each visit the wound was inspected for clinical signs of infection. Evaluation at each visit revealed marked development in granulation tissue to the wound base and significant decrease in size. Eight weeks after the initial application of the allograft tissue the wound was closed.

Photographs of the remarkable wound healing mediated by a placental product of the present invention as shown in FIG. 21. Panel A: Osteomyelitis, tendon exposed, probed to bone. First stem cell graft was applied after surgical debridement; B: Status post 1 application of stem cell graft, wound is granular in nature and no signs of infection; C: 3 weeks post surgical intervention; 2 applications on the instant membrane product, the wound is considerably smaller in circumference and depth; D: 6 weeks post surgical intervention the wound is almost closed; E: 8 weeks and 7 applications of the instant membrane product, the wound is closed.

CONCLUSION

Despite the tremendous progress in skin tissue engineering in the past few decades, current therapy has limited efficacy in the treatment of chronic diabetic ulceration. As shown in this case report of two patients, the use of advanced therapies containing stem cells may prove useful to ultimately heal these patients in lieu of amputation, reduce mortality rates, and at the same time be a cost effective alternative to standard treatments currently on the market. Both patients highlighted in this case report received 7 applications of a membrane product of the present invention. Complete healing occurred in both patients. There were no reported complications associated with treatment; the instant membrane product was safe and effective in an initial evaluation of two patients with diabetic foot ulceration at-risk for amputation. These results indicate that patients with recalcitrant, chronic wounds should be considered for this novel therapy.

The invention claimed is:

1. A method of generating an immunocompatible amniotic membrane, the method comprising:
    (a) isolating an amniotic membrane from a placenta;
    (b) refrigerating the amniotic membrane in a cryopreservation medium at 2° C. to 8° C. for at least 30 minutes to deplete one or more types of immunogenic maternal cells; and
    (c) cryopreserving the amniotic membrane in a cryopreservation medium at a freezing temperature, thereby generating the immunocompatible amniotic membrane, wherein the immunocompatible amniotic membrane comprises at least 70% viable therapeutic cells, wherein the viable therapeutic cells are native to the amniotic membrane, wherein the viable therapeutic cells comprise two or more cell types selected from mesenchymal stem cells (MSCs), fibroblasts, and epithelial cells, and wherein the immunocompatible amniotic membrane produces a non-immunogenic response in a mixed lymphocyte reaction assay.

2. The method of claim 1, wherein the immunogenic maternal cells are maternal leukocytes, maternal dendritic cells, maternal decidual cells, or a combination thereof.

3. The method of claim 1, wherein the freezing temperature is between −85° C. and −75° C.

4. The method of claim 1, wherein the cryopreservation medium comprises a cell-permeating cryopreservative.

5. The method of claim 4, wherein the cell-permeating cryopreservative comprises dimethylsulfoxide (DMSO).

6. The method of claim 1, wherein refrigerating the amniotic membrane in a cryopreservation medium selectively kills or inactivates functional CD14+ macrophage cells.

7. The method of claim 1, wherein the amniotic membrane is treated with an anti-TNF-α antibody.

8. The method of claim 1, wherein the amniotic membrane is treated with IL-10.

9. The method of claim 1, wherein the immunocompatible amniotic membrane generates less than about 50 pg/ml of IL-2αR.

10. The method of claim 1, wherein the immunocompatible amniotic membrane generates less than about 20 pg/ml of IL-2αR.

11. The method of claim 1, wherein the immunocompatible amniotic membrane produces a level of TNF-α release after LPS stimulation that is less than 420 pg/ml.

12. The method of claim 1, wherein the immunocompatible amniotic membrane produces a level of TNF-α release after LPS stimulation that is less than 200 pg/ml.

13. The method of claim 1, wherein the viable therapeutic cells further comprise stromal cells present at about 2,000 to about 15,000 cells per cm$^2$ of the immunocompatible amniotic membrane.

14. The method of claim 1, wherein the viable therapeutic cells comprise MSCs, wherein at least 40% of the MSCs are viable after a freeze-thaw cycle.

* * * * *